US011590110B2

(12) United States Patent
Gramatica et al.

(10) Patent No.: US 11,590,110 B2
(45) Date of Patent: Feb. 28, 2023

(54) COMPOSITIONS AND METHODS FOR REACTIVATING LATENT IMMUNODEFICIENCY VIRUS USING A GSK-3 INHIBITOR

(71) Applicant: The J. David Gladstone Institutes, a testamentary trust established under the Will of J. David Gladstone, San Francisco, CA (US)

(72) Inventors: Andrea Gramatica, San Francisco, CA (US); Warner C. Greene, Hillsborough, CA (US)

(73) Assignee: The J. David Gladstone Institutes, a testamentary trust established under the Will of J. David Gladstone, San Francisco, CA (US)

( * ) Notice: Subject to any disclaimer, the term of this patent is extended or adjusted under 35 U.S.C. 154(b) by 0 days.

(21) Appl. No.: 16/619,047

(22) PCT Filed: Jun. 5, 2018

(86) PCT No.: PCT/US2018/036101
§ 371 (c)(1),
(2) Date: Dec. 3, 2019

(87) PCT Pub. No.: WO2018/226721
PCT Pub. Date: Dec. 13, 2018

(65) Prior Publication Data
US 2020/0085797 A1    Mar. 19, 2020

Related U.S. Application Data

(60) Provisional application No. 62/515,943, filed on Jun. 6, 2017.

(51) Int. Cl.
*A61K 31/433* (2006.01)
*A61K 31/404* (2006.01)
*A61P 31/18* (2006.01)

(52) U.S. Cl.
CPC .......... *A61K 31/433* (2013.01); *A61K 31/404* (2013.01); *A61P 31/18* (2018.01)

(58) Field of Classification Search
CPC .................................................. A61K 31/433
(Continued)

(56) References Cited

U.S. PATENT DOCUMENTS

2001/0006638 A1    7/2001  Allen
2005/0222220 A1*  10/2005  Padilla ..................... A61P 5/00
                                                    514/362

(Continued)

FOREIGN PATENT DOCUMENTS

WO        2018226721        12/2018

OTHER PUBLICATIONS

Dominguez et al. "Evidence for irreversible inhibition of glycogen synthase kinase-3β by Tideglusib," J. Biological Chemistry, 2012, vol. 287, No. 2, pp. 893-904 (Year: 2012).*

(Continued)

*Primary Examiner* — Shengjun Wang
(74) *Attorney, Agent, or Firm* — Schwegman Lundberg & Woessner, P.A.

(57) ABSTRACT

The present disclosure provides compositions and methods for reactivating latent immunodeficiency virus using a glycogen synthase kinase 3α inhibitor, such as a glycogen synthase kinase 3α (GSK-3α) or a glycogen synthase kinase 3β (GSK-3β) inhibitor. In some embodiments, the glycogen synthase kinase 3 inhibitor is a glycogen synthase kinase antagonist, e.g., Tideglusib (4-benzyl-2-(naphthalen-1-yl)-1,2,4-thiadiazolidine-3,5-dione), or a pharmaceutically acceptable salt or derivative thereof. In other embodiments, the glycogen synthase kinase 3 inhibitor is a maleimide-based glycogen synthase kinase 3 inhibitor, e.g., SB-216763

(Continued)

(3-(2,4-Dichlorophenyl)-4-(1-methyl-1H-indol-3-yl)-1H-pyrrole-2,5-dione) or a pharmaceutically acceptable salt or derivative thereof.

5 Claims, 30 Drawing Sheets

(58) Field of Classification Search
USPC .......................................................... 514/361
See application file for complete search history.

(56) References Cited

U.S. PATENT DOCUMENTS

| 2012/0190009 A1 | 7/2012 | Kashanchi et al. |
| 2015/0099012 A1 | 4/2015 | Mahmoudi |

OTHER PUBLICATIONS

Guendel et al. "Novel neuroprotective GSK-3β inhibitor restricts Tat-Mediated HIV-1 replication," Journal of Virology, 2014, vol. 88, No. 2, pp. 1189-1208 (Year: 2014).*
"International Application Serial No. PCT US2018 036101, International Search Report dated Sep. 12, 2018", 3 pgs.
"International Application Serial No. PCT US2018 036101, Written Opinion dated Sep. 12, 2018", 5 pgs.
"PUBCHEM-CID 11405589", (Oct. 26, 2006), 6 pgs.
"PUBCHEM-CID 9956119", (Oct. 25, 2006), 7 pgs.
"International Application Serial No. PCT US2018 036101, International Preliminary Report on Patentability dated Dec. 19, 2019", 7 pgs.

* cited by examiner

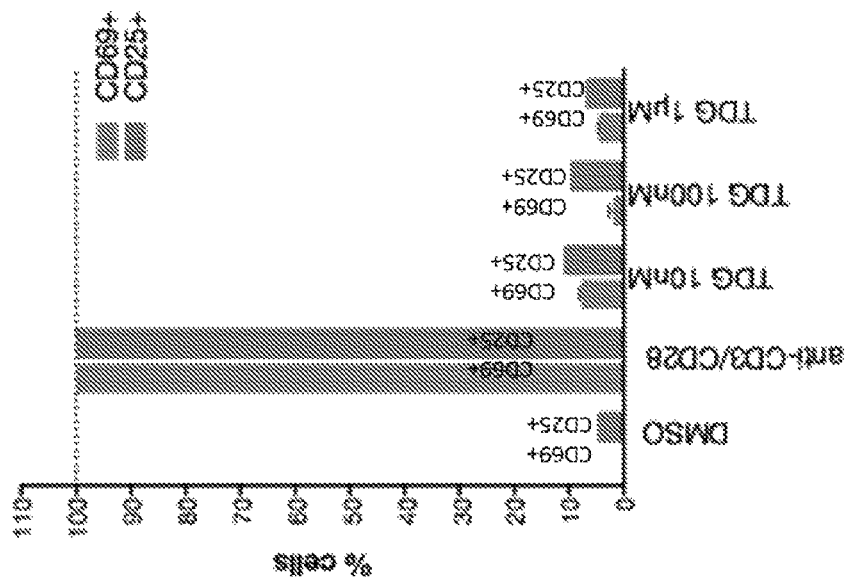
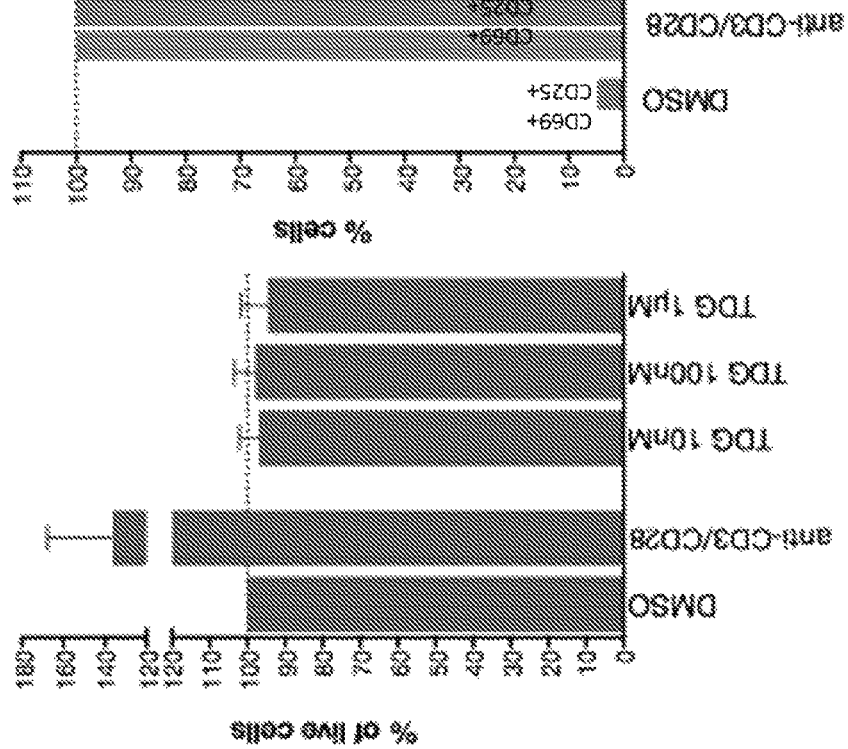
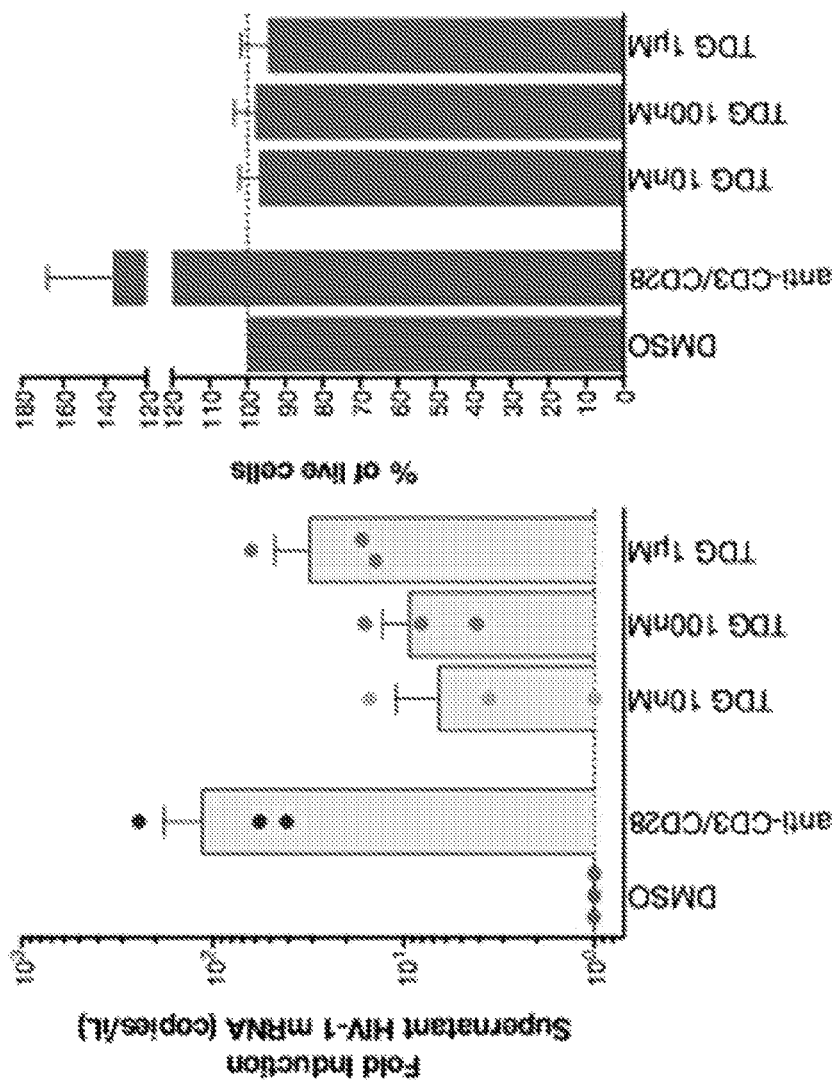

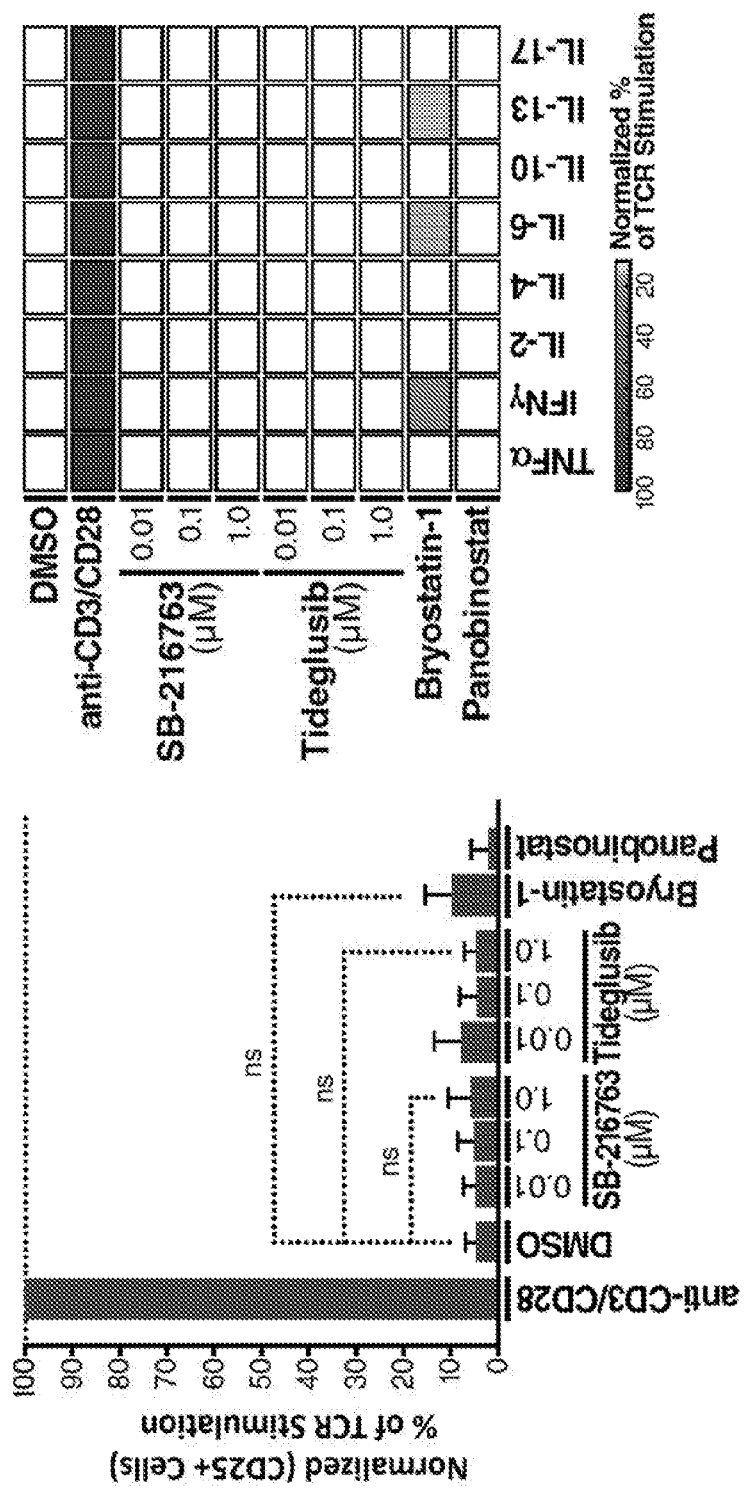

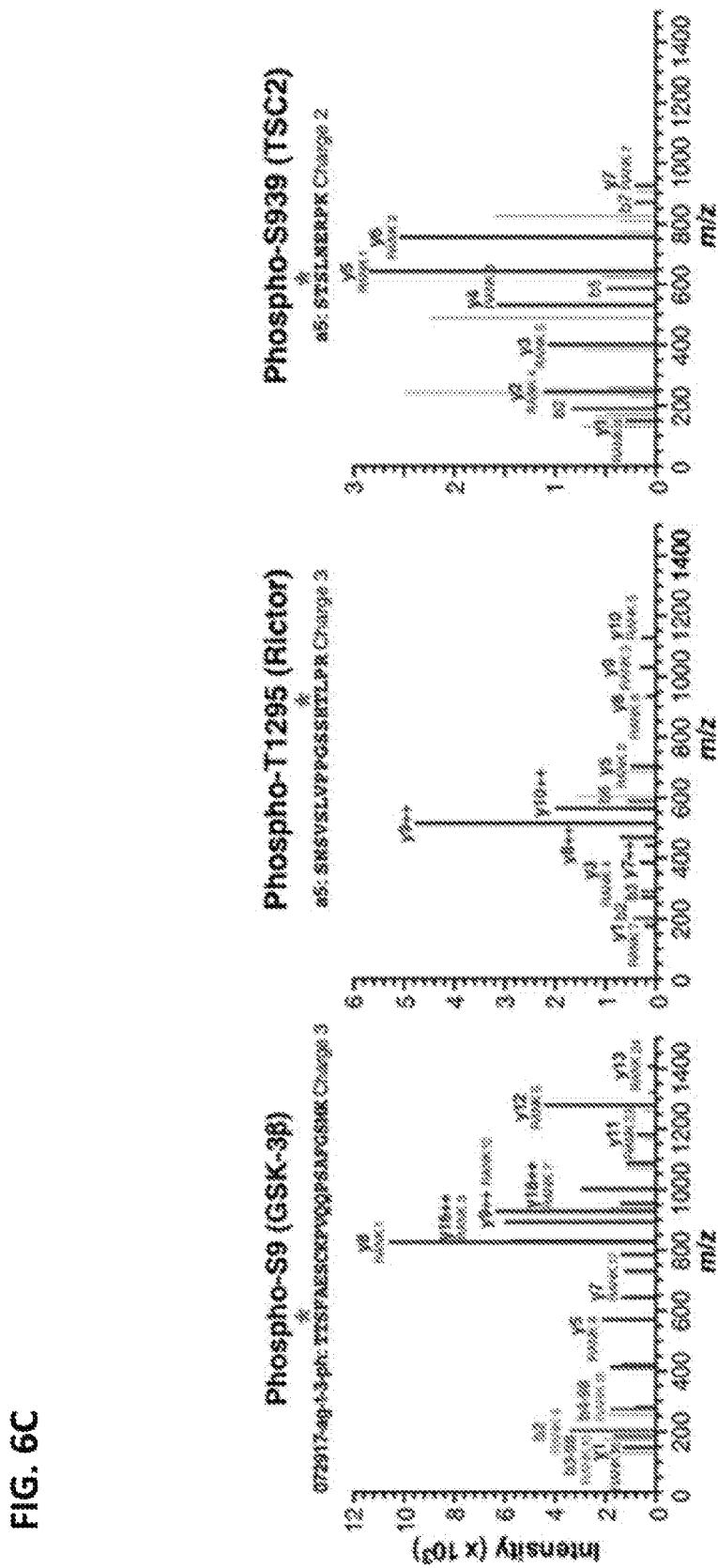

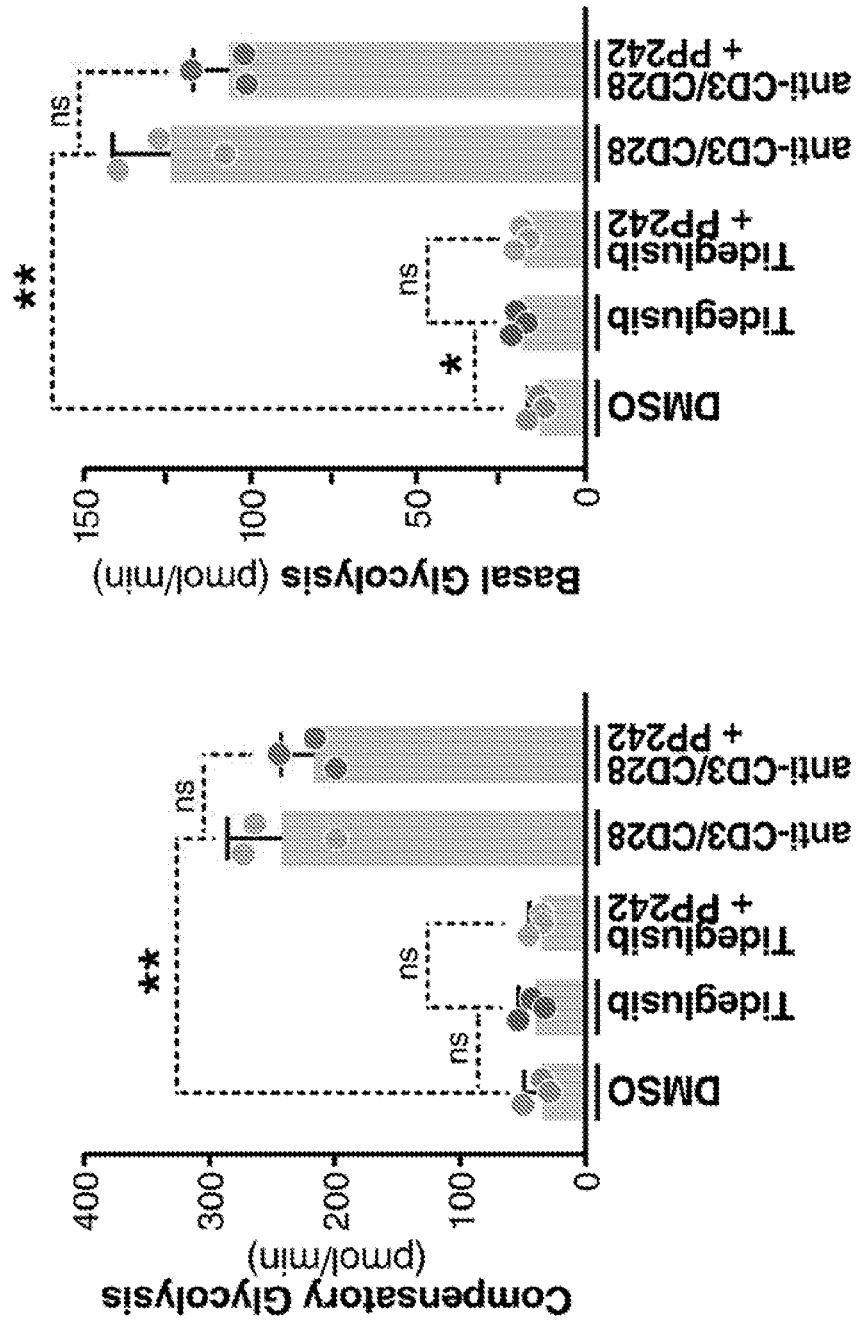

FIG. 14

Amino acid sequence of human glycogen synthase kinase-3 alpha

MSGGGGPSGGG PGGSGRARTS SFAEPGGGGG GGGGGPGGSA SGPGGTGGGK
ASVGAMGGGV GASSSGGGPG GSGGGGSGGP GAGTSFPPPG VKLGRDSGKV
TTVVATLGQG PERSQEVAYT DIKVIGNGSF GVVYQARLAE TRELVAIKKV
LQDKRFKNRE LQIMRKLDHC NIVRLRYFFY SSGEKKDELY LNLVLEYVPE
TVYRVARHFT KAKLTIPILY VKVYMYQLFR SLAYIHSQGV CHRDIKPQNL
LVDPDTAVLK LCDFGSAKQL VRGEPNVSYI CSRYYRAPEL IFGATDYTSS
IDVWSAGCVL AELLLGQPIF PGDSGVDQLV EIIKVLGTPT REQIREMNPN
YTEFKFPQIK AHPWTKVFKS RTPPEAIALC SSLLEYTPSS RLSPLEACAH
SFFDELRCLG TQLPNNRPLP PLFNFSAGEL SIQPSLNAIL IPPHLRSPAG
TTTLTPSSQA LTETPTSSDW QSTDATPTLT NSS (SEQ ID NO://)

FIG. 15

Amino acid sequence of human glycogen synthase kinase-3 beta

MSGRPRTTSF AESCKPVQQP SAFGSMKVSR DKDGSKVTTV VATPGQGPDR
PQEVSYTDTK VIGNGSFGVV YQAKLCDSGE LVAIKKVLQD KRFKNRELQI
MRKLDHCNIV RLRYFFYSSG EKKDEVYLNL VLDYVPETVY RVARHYSRAK
QTLPVIYVKL YMYQLFRSLA YIHSFGICHR DIKPQNLLLD PDTAVLKLCD
FGSAKQLVRG EPNVSYICSR YYRAPELIFG ATDYTSSIDV WSAGCVLAEL
LLGQPIFPGD SGVDQLVEII KVLGTPTREQ IREMNPNYTE FKFPQIKAHP
WTKVFRPRTP PEAIALCSRL LEYTPTARLT PLEACAHSFF DELRDPNVKL
PNGRDTPALF NFTTQELSSN PPLATILIPP HARIQAAAST PTNATAASDA
NTGDRGQTNN AASASASNST (SEQ ID NO://)

COMPOSITIONS AND METHODS FOR REACTIVATING LATENT IMMUNODEFICIENCY VIRUS USING A GSK-3 INHIBITOR

This application claims the benefit of U.S. Provisional Patent Application No. 62/515,943, filed Jun. 6, 2017, which application is incorporated herein by reference in its entirety.

INTRODUCTION

HIV latency is established early during acute infection and is primarily found within memory CD4+ T cell subsets. This reservoir, although almost transcriptionally silent, is fully capable of generating infectious virus when the host cell is reactivated by antigen or cytokine stimulation or when antiretroviral therapy is interrupted. The latent HIV reservoir is principally found in lymphoid tissues where 98% of the CD4+ T cells reside. Although Highly Active Antiretroviral Therapy (HAART) is capable of suppressing viral replication, it fails to eradicate latent reservoirs.

Efforts to purge latent HIV have initially focused on reactivating latent proviruses with cytokines or T cell receptor activating agents. However, these strategies often result in severe side effects and generally have low efficacy. The so-called "Shock and Kill" strategy, instead, involves reactivation of transcriptionally silent proviruses through administration of latency reversal agents (LRAs), which are chemical compounds able to induce HIV transcription without fully activating the cells of the immune system. However, LRAs used so far in clinical and pre-clinical studies have largely been inadequately active, associated with cellular toxicity, and/or associated with broad CD4+ T cell activation. For example, HDAC inhibitors have been found to compromise cytotoxic T-lymphocytes (CTL) and natural killer (NK) cell activity (Jones et al. *PLoS Pathog.* 2014 Aug. 14; 10(8):e1004287. doi: 10.1371/journal.ppat.1004287. eCollection 2014 August; Garrido et al. *Front Immunol.* 2016 Sep. 21; 7:356. eCollection 2016). In addition, protein kinase C (PKC) activators, which have been used as LRAs, can inhibit CTL activity (Schrezenmeier et al. *Immunology.* 1986 November; 59(3): 359-363) and induce broad CD4+ T cell activation (Martinez-Bonet et al. *Scientific Reports* 5, Article number: 16445 (2015) doi: 10.1038/srep16445). Accordingly, despite recent advances in the use of LRAs, there remains a need in the art for safe and potent LRAs which demonstrate efficient reactivation of latent HIV in the absence of cellular toxicity and broad T cell activation. Ideal LRAs should also display high tissue permeability, and not interfere with the cytolytic effector function of CTLs and NK cells.

SUMMARY

The present disclosure provides compositions and methods for reactivating latent immunodeficiency virus using a glycogen synthase kinase 3 inhibitor, such as a glycogen synthase kinase 3α (GSK-3α) or a glycogen synthase kinase 3β (GSK-3β) inhibitor. In some embodiments, the glycogen synthase kinase 3 inhibitor is a glycogen synthase kinase antagonist, e.g., Tideglusib (4-benzyl-2-(naphthalen-1-yl)-1,2,4-thiadiazolidine-3,5-dione), or a pharmaceutically acceptable salt or derivative thereof. In other embodiments, the glycogen synthase kinase 3 inhibitor is a maleimide-based glycogen synthase kinase 3 inhibitor, e.g., SB-216763 (3-(2,4-Dichlorophenyl)-4-(1-methyl-1H-indol-3-yl)-1H-pyrrole-2,5-dione) or a pharmaceutically acceptable salt or derivative thereof.

BRIEF DESCRIPTION OF THE DRAWINGS

FIGS. 3A-3C depict the treatment of CD4+ T cells from HIV-positive individuals (3 donors) on suppressive ART. Treatment with Tideglusib induces potent HIV-1 latency reversion without reducing cell viability and without inducing broad T cell activation. FIG. 3A depicts fold induction of HIV-1 mRNA in the supernatant of purified CD4+ T cells treated with αCD3/CD28 beads (positive control), 0.01% DMSO (negative control) or Tideglusib at the indicated concentrations following 48 hours of culture. Quantification of virus release in the culture supernatant was evaluated with ddPCR and presented as fold induction relative to the untreated control (DMSO-treated sample). FIG. 3B depicts an evaluation of CD4+ T cell viability with Cell Titer Blue assay. Substantially all of the cells remained viable after treatment with Tideglusib. FIG. 3C depicts the percentage of CD4 T cells expressing activation markers (i.e., CD69 and CD25) upon treatment with Tideglusib, relative to αCD3/CD28-treated samples (set to 100%).

FIG. 4A depicts a schematic representation of the workflow followed for the analysis of latency reversion in blood and GALT cultures measured as HIV-1 virion levels (i.e. HIV-1 mRNA copies/μl).

FIG. 4B depicts results for blood CD4+ T cells treated for 48 hours with single LRAs or anti-CD3/CD28 coated beads. FIG. 4C depicts GALT samples treated for 24 hours with 1 μM tideglusib or anti-CD3/CD28 coated beads. FIG. 4D depicts blood CD4+ T cells treated for 48 hours with 1 μM tideglusib, anti-CD3/CD28 coated beads, or a combination of tideglusib with PP242 or IKK V. All data are presented as fold induction relative to the untreated control. Treatments were done at the following concentrations/volumes: DMSO control=0.001% v/v final volume; anti-CD3/CD28 coated beads=125 μl (25 μl per 1×10$^6$ cells); Bryostatin-1=10 nM; Panobinostat=50 nM; PP242=250 nM; IKK V=25 nM.

FIGS. 5A-5D demonstrate that treatment with SB-216763 or tideglusib does not reduce viability of CD4+ T cells and does not induce T cell activation or cytokine production. The blood CD4+ T cell cultures used to study latency reversion in FIGS. 4A-4D were analyzed for viability (FIG. 5A), surface expression of activation markers (FIGS. 5B, 5C) and release of cytokines in the culture supernatant (FIG. 5D). Data shown in FIG. 5A are the mean effect of 6 representative donors (independently treated), presented as percentage of untreated control (DMSO=100%); Data shown in FIGS. 5B and 5C are the mean effect of 6 representative donors (independently treated), presented as percentage of total activation, as obtained with treatment with anti-CD3/

CD28 coated beads; Data shown in FIG. 5D are the mean effect of 12 representative donors (independently treated) presented as both percentage of total activation with anti-CD3/CD28 coated beads (anti-CD3/CD28=100) and untreated control (DMSO=1). Statistical significance was calculated using a ratio paired t test compared with each untreated (DMSO) controls (*P<0.05; P<0.005; *P<0.0005; ****P<0.00005). Error bars represent standard error of the mean.

Figure 5A:
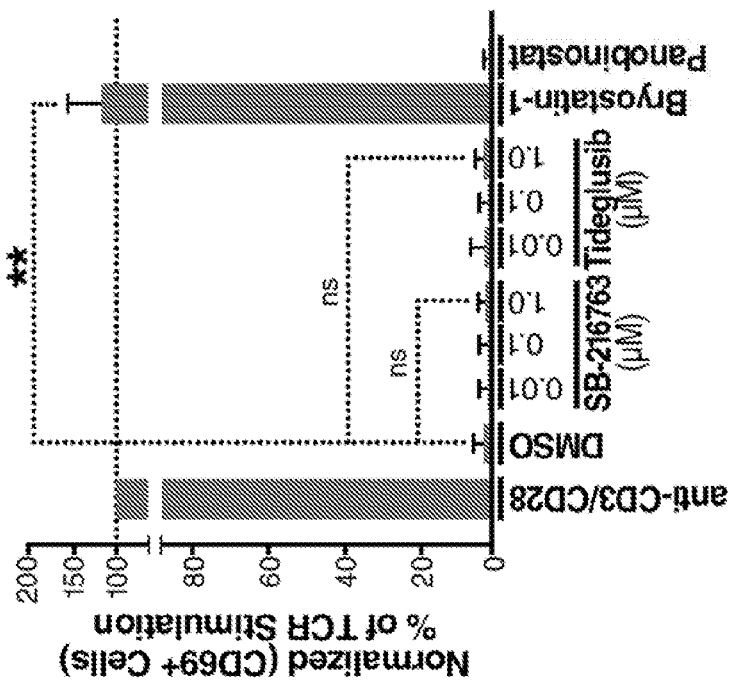
Figure 5B:
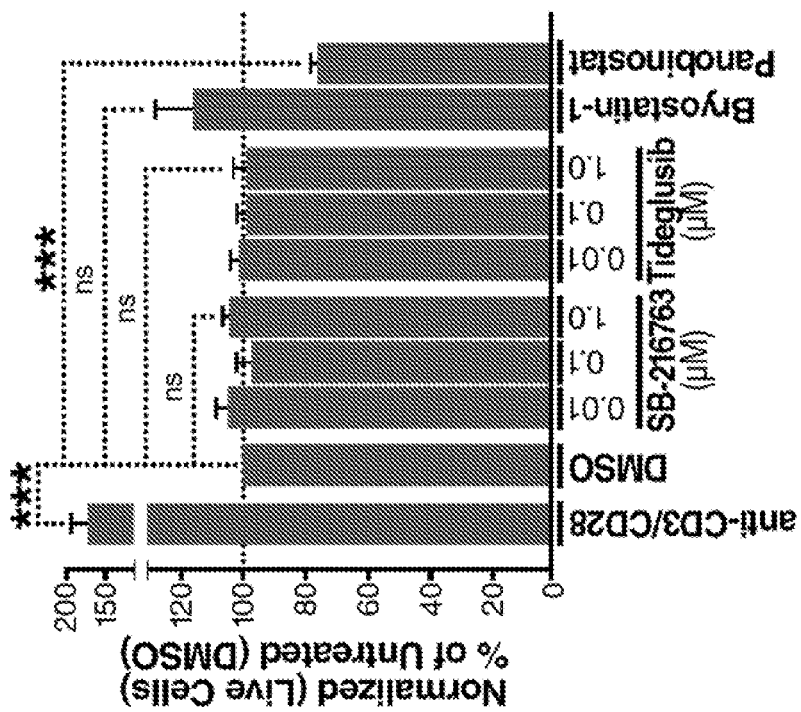

FIG. 5A depicts normalized percentage of live CD4+ T cells shown as comparison to untreated control. FIGS. 5B and 5C depict Result of LRA stimulation on surface expression of CD69 (5B) and CD25 (5C) activation markers. Lymphocytes were gated on single cells>live>CD3+ and CD69+ or CD25+. FIG. 5D depicts after virus purification, culture supernatants of treated CD4+ T cells were tested for cytokine release using a pro-inflammatory panel including TNFα, IFN-γ, IL-2, IL-4, IL-6, IL-10, IL-13, IL-17.

Figure 6A:
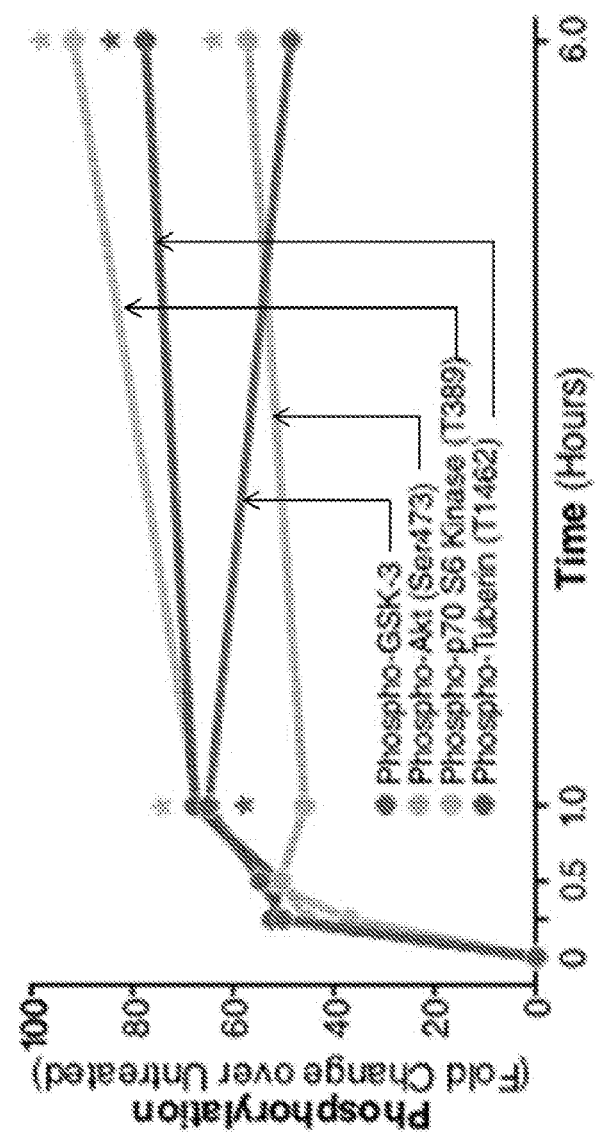
Figure 6B:
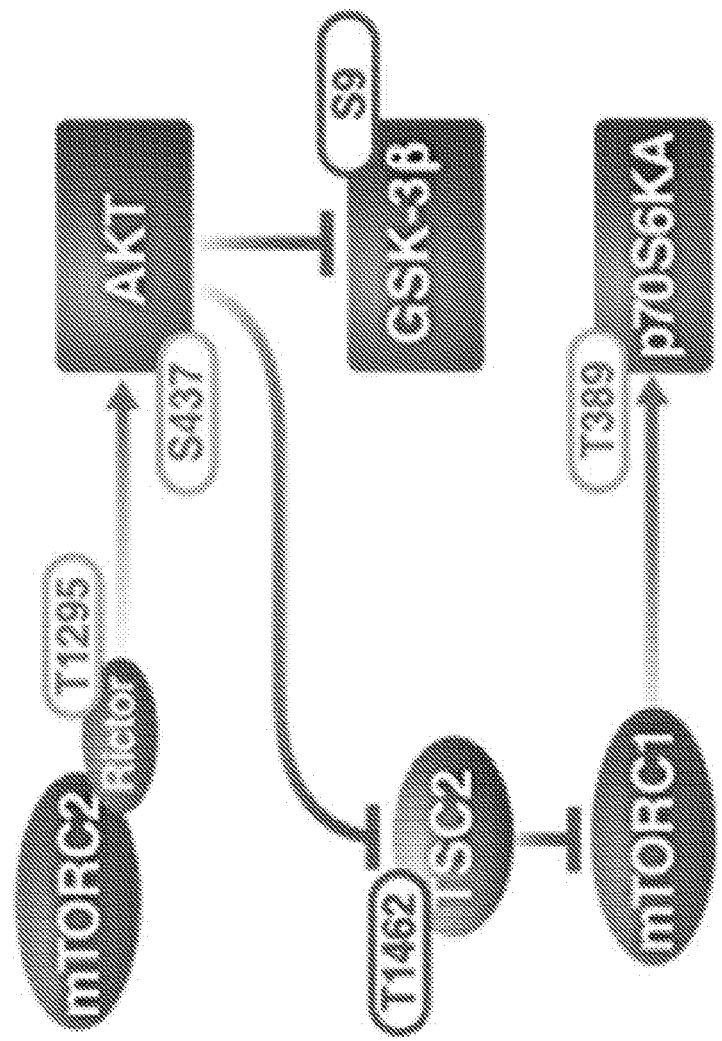

FIGS. 6A-6C demonstrate that Tideglusib activates the AKT/mTOR pathway as reported by Nanostring and phosphoproteomics analysis of CD4+ T cells from infected individuals on ART. Tideglusib specifically influences activation status of specific proteins of the AKT/mTOR pathway. FIG. 6A depicts nanoString analysis of CD4+ T cells treated with 1 μM tideglusib for up to 6 h. The differential expression of Phospho-GSK3β (color), Phospho-Akt (color), Phospho-p70 S6 Kinase (color) and Phospho-Tuberin (color) is represented as linear fold change normalized to the untreated control. Stars denote points with unadjusted p-value≤0.05. Each data point comprises 5 biological replicates, n=5. FIG. 6B depicts a schematic representation of the phosphorylation sites detected by nanoString and phosphoproteomics on the respective protein/protein complexes. FIG. 6C depicts MS/MS spectra identifying GSK-3β S9 (TTS*FAESCKPVQQPSAFGSMK), TSC2 S939 (STS*LNERPK) and Rictor T1295 (SNSVSLVPPGSSHT*LPR) phosphorylation annotated by the Skyline spectrum builder. B and y fragment ions are indicated in purple and blue, respectively. Fragment ion charge states are 1+ unless indicated otherwise.

Figure 7A:
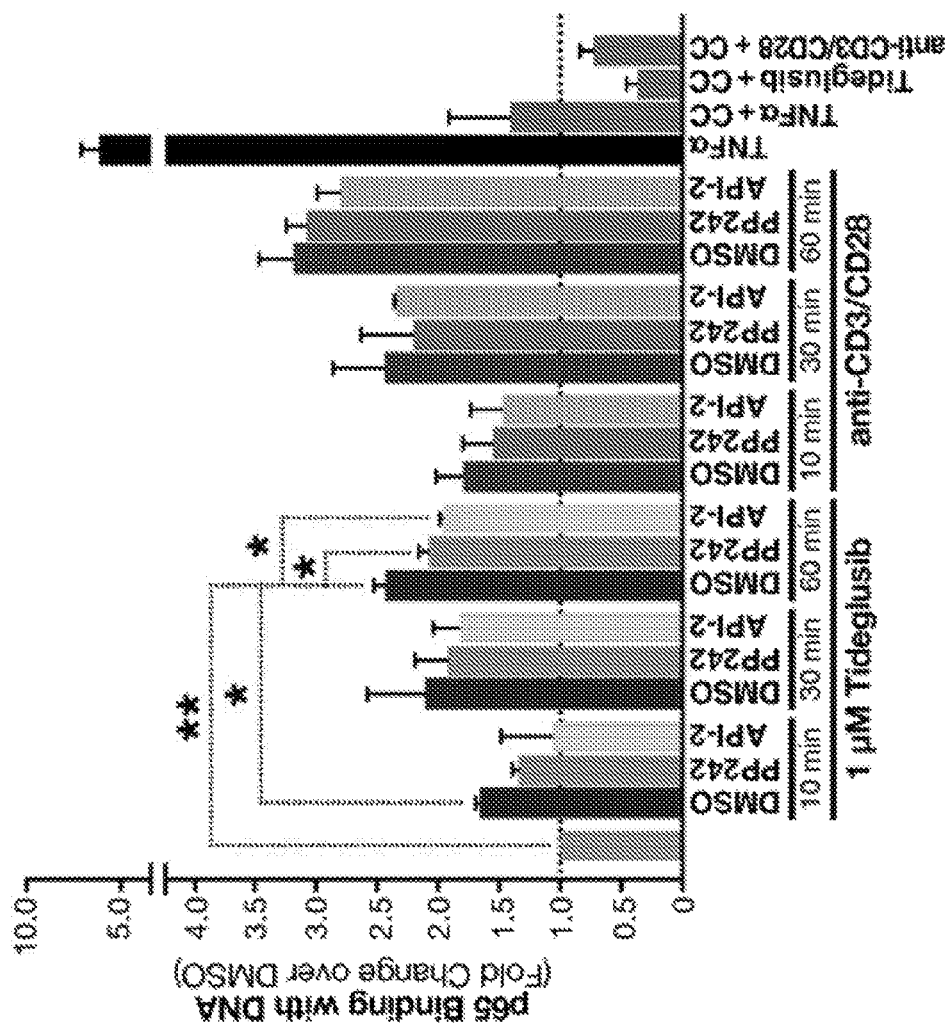
Figure 7B:
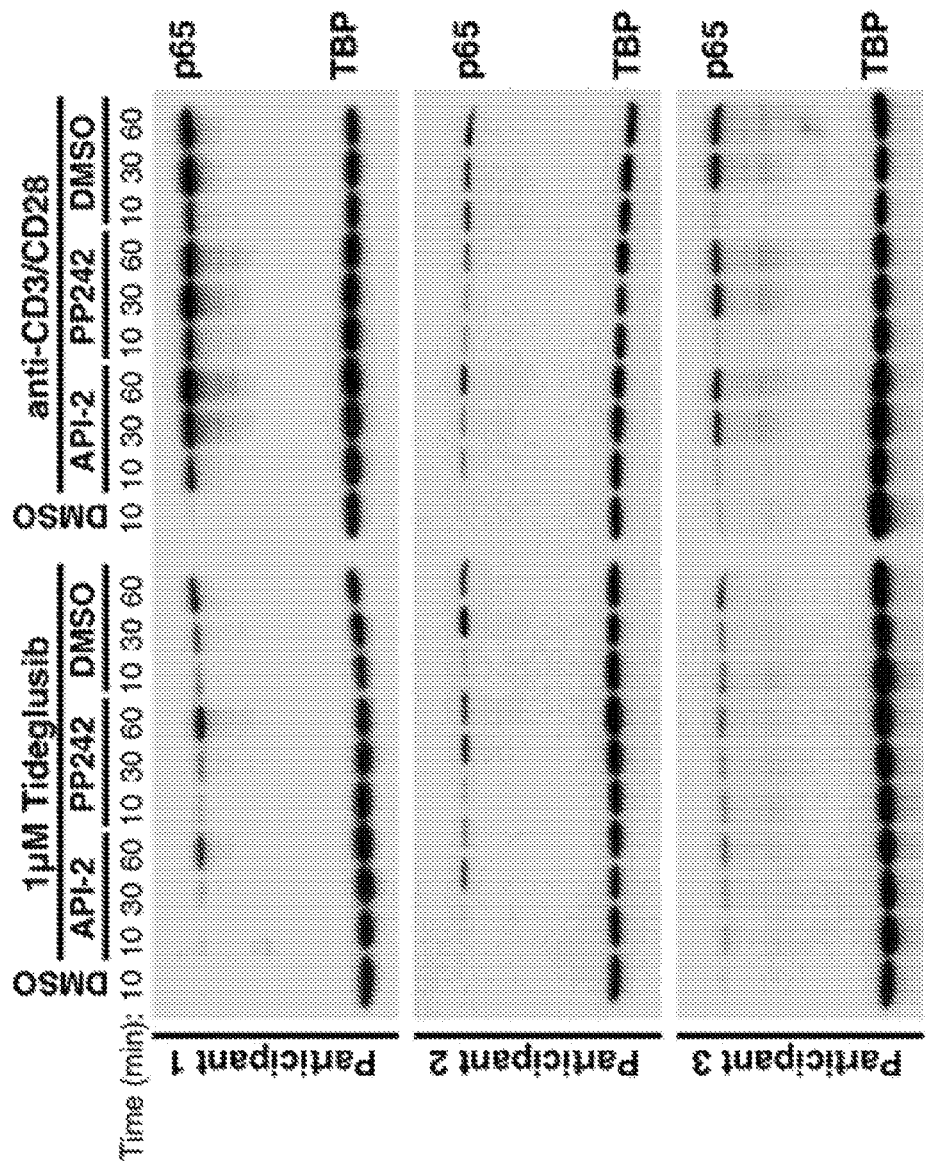

FIGS. 7A-7B demonstrate that AKT and mTOR modulates tideglusib-mediated NF-kB activation in CD4+ T cells. CD4+ T cells extracted from three HIV-negative participants were treated as indicated with either 1 μM tideglusib, anti-CD3/CD28 coated beads alone or in the presence of 250 nM PP242, 250 nM API-2, or left untreated (DMSO control). FIG. 7A depicts a nuclear extract run by western blot with anti-p65 antibodies to measure NF-κB nuclear translocation. FIG. 7B depicts nuclear extracts analyzed with an ELISA to quantify p65 binding with target dsDNA. Nuclear extracts treated with TNFα served as positive control, while TNFα/tideglusib or anti-CD3/CD28+cold probe (cc) served as negative control. Anti-TATA binding protein (TBP) antibodies were used as loading control to ensure equal protein loading for western blot and ELISA. All data is n=3 biological replicates. Data are mean+/−SEM of technical and biological replicates. paired two-tailed Student's t test. *, P<0.05; ** P<0.01.

Figure 8:
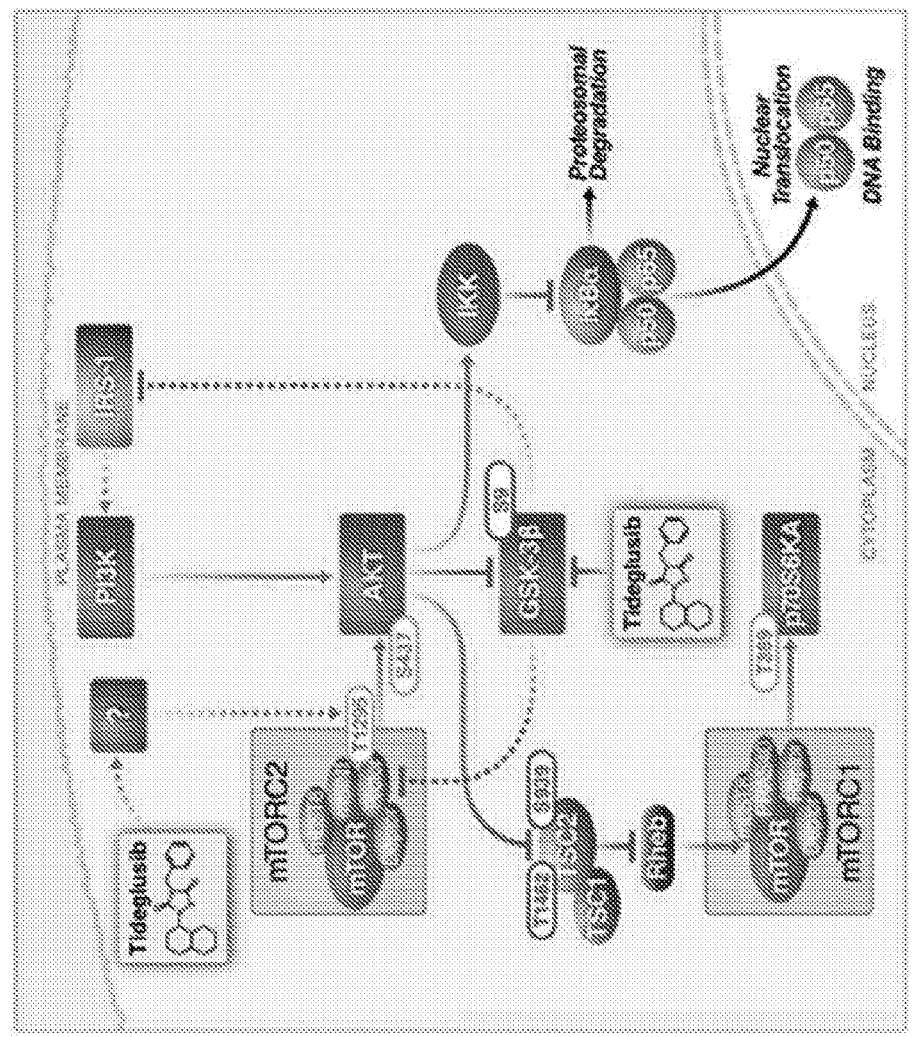

FIG. 8 depicts a schematic of the regulation of AKT, mTOR and NF-κB mediated by tideglusib in CD4+ T cells. All the phosphorylation events reported here were experimentally confirmed by Nanostring analysis or phosphoproteomics. Some of the lines shown here (dotted lines) represent proposed/not confirmed interactions. Green arrows indicate activation; red arrows indicate inhibition. The reported phosphosites represent activating (green) or inhibiting (red) phosphorylation events.

Figure 9A:
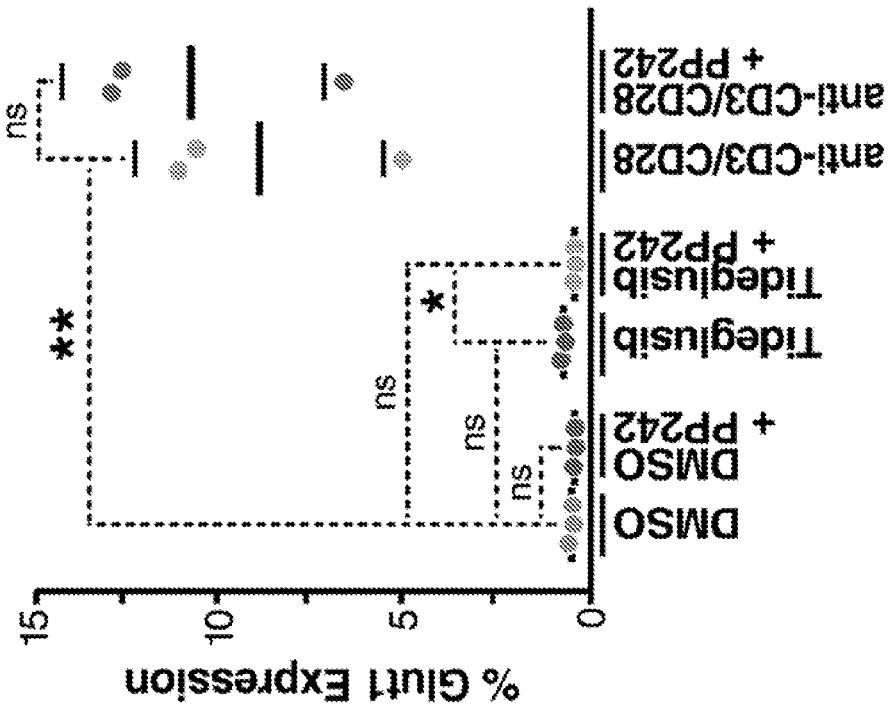
Figure 9B:
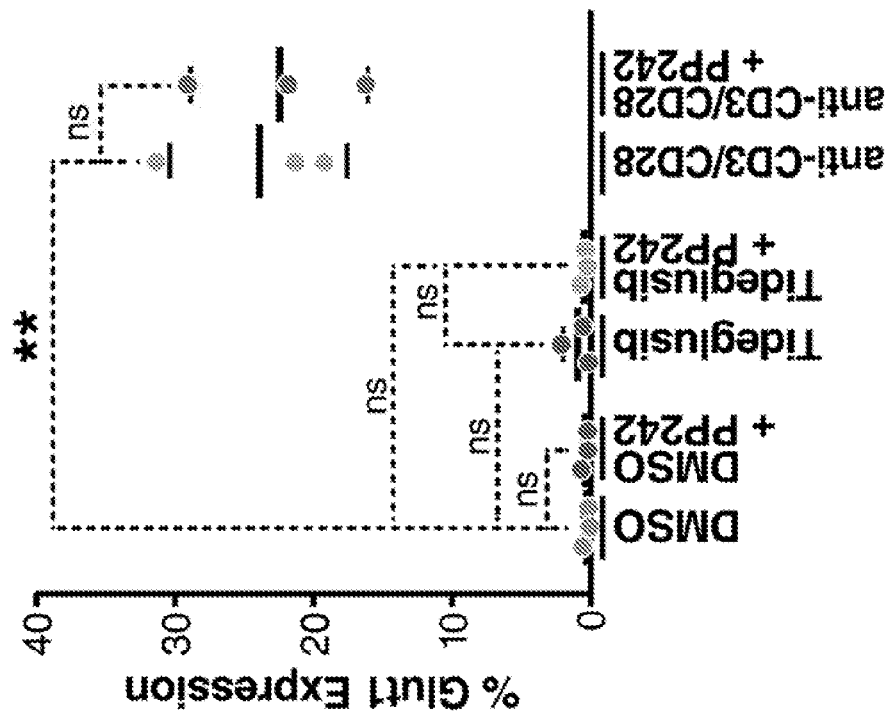
Figure 9C:
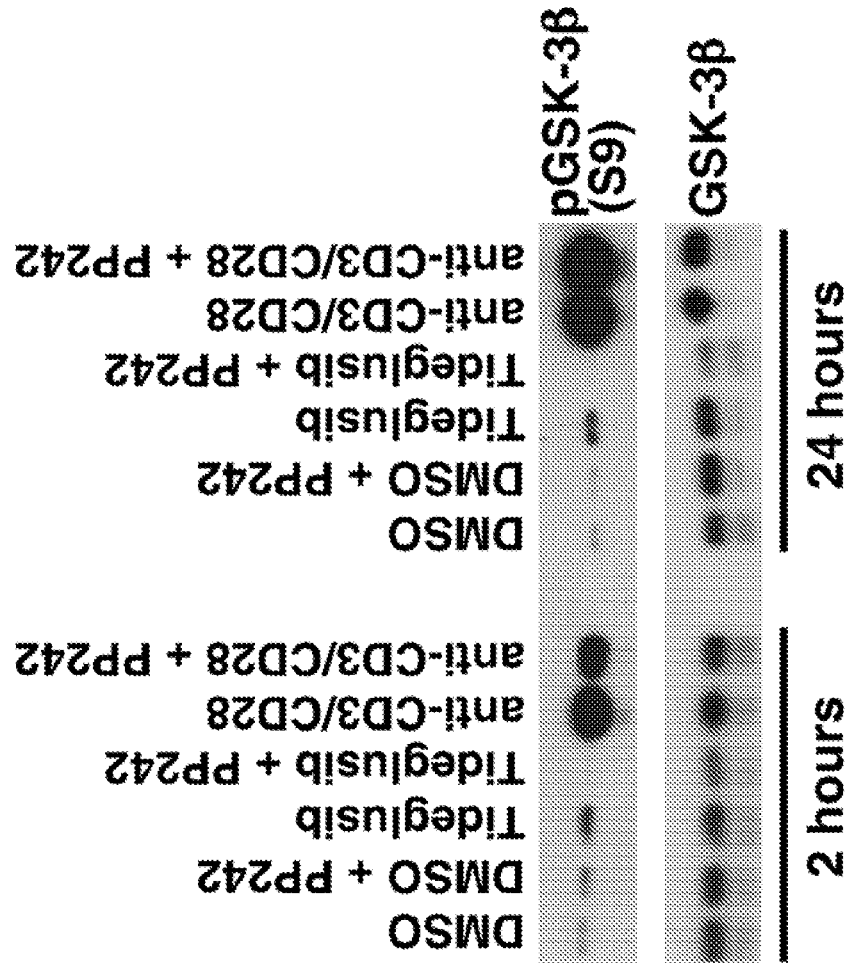
Figure 9D:
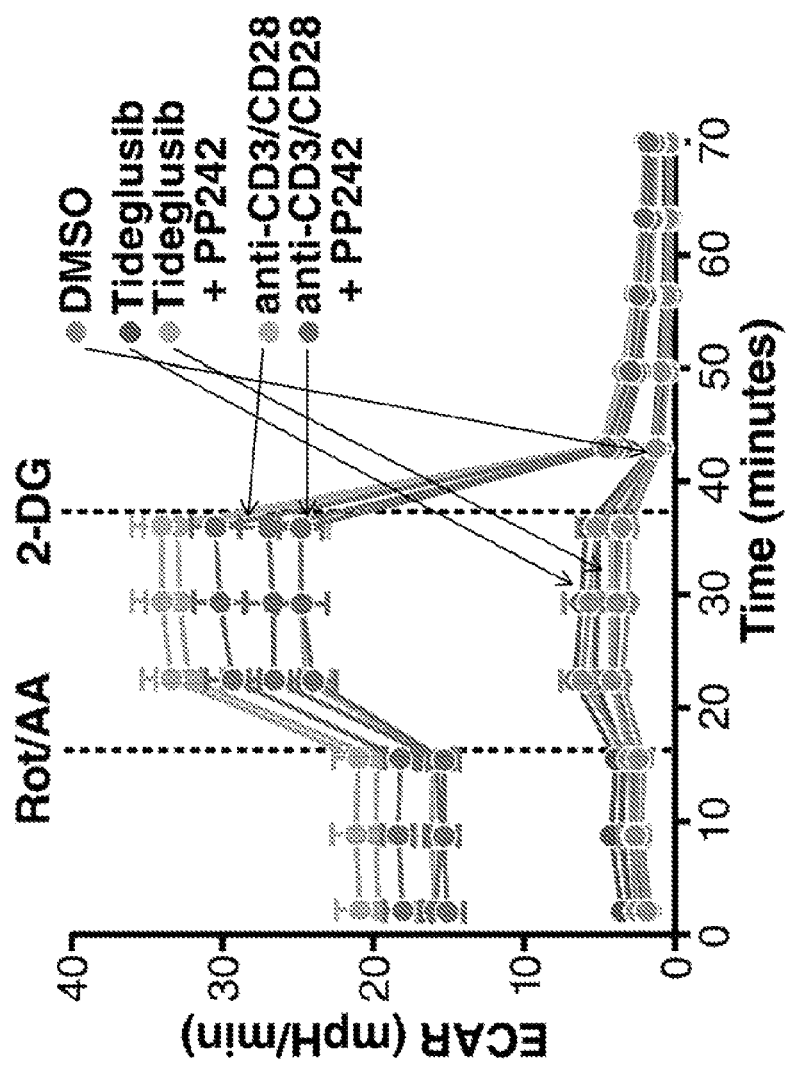
Figure 9G:
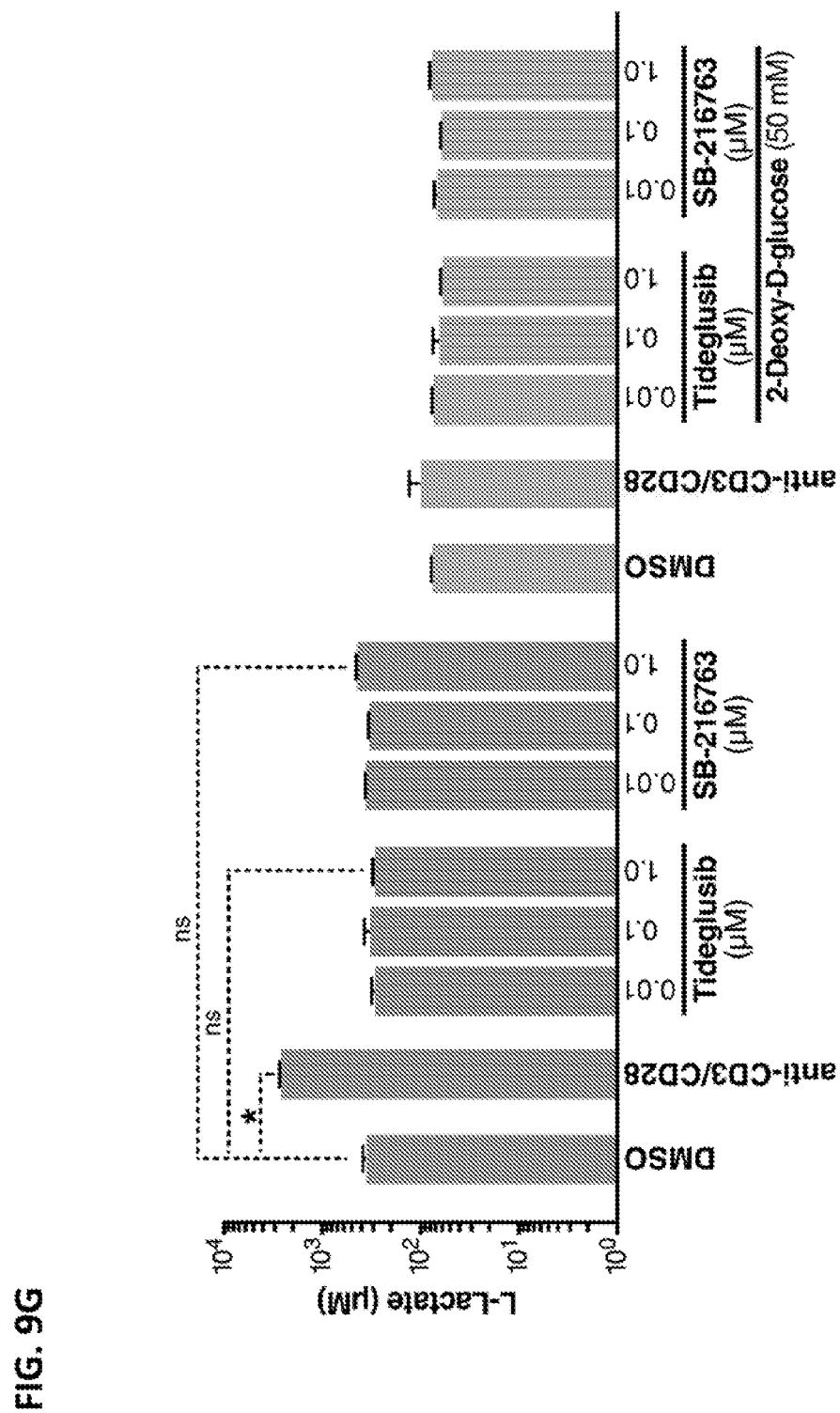

FIGS. 9A-9G demonstrate that the inhibition of GSK-3β does not increase glycolytic metabolism in CD4+ T cell. CD4+ T cells were isolated from blood of HIV-uninfected individuals and treated with indicated inhibitors. FIG. 9A depicts GLUT1 surface expression analyzed by flow cytometry after 1 μM tideglusib treatment for 2 h. FIG. 9B depicts GLUT1 surface expression analyzed by flow cytometry after 1 μM tideglusib treatment for 24 h (n=3 biological replicates). FIG. 9G depicts the quantification of L-Lactate in supernatant from CD4+ T cells 24 hours post treatment with the indicated GSK-3β and glycolysis inhibitors (n=3 biological replicates). FIG. 9D depicts the assessment of glycolytic profile using a standard glycolytic rate test and Seahorse technology measuring OCR (oxygen consumption rate, not shown) and ECAR (extracellular acidification rate) 24 hours after treatment with 1 μM tideglusib (shown is the mean+/−SEM of six technical replicates (n=3 biological replicates). FIG. 9E depicts basal glycolysis as derived from FIG. 9D. FIG. 9F depicts compensatory glycolysis as calculated from FIG. 9D. FIG. 9C depicts cells from FIG. 9D that were probed for phospho-GSK-3β (Serine 9) by western blot after 2 and 24 hours treatment with 1 μM tideglusib. A single representative immunoblot is provided. All data is n=3 biological replicates.

Figure 10B:
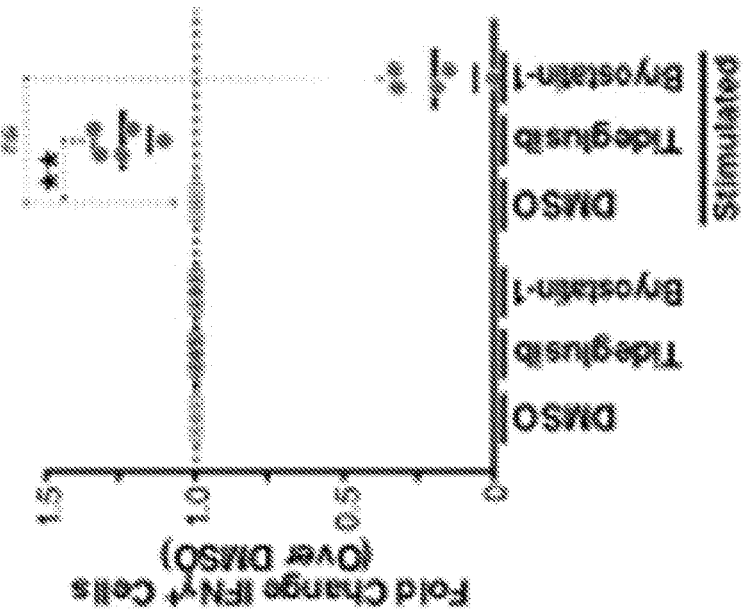
Figure 10A:
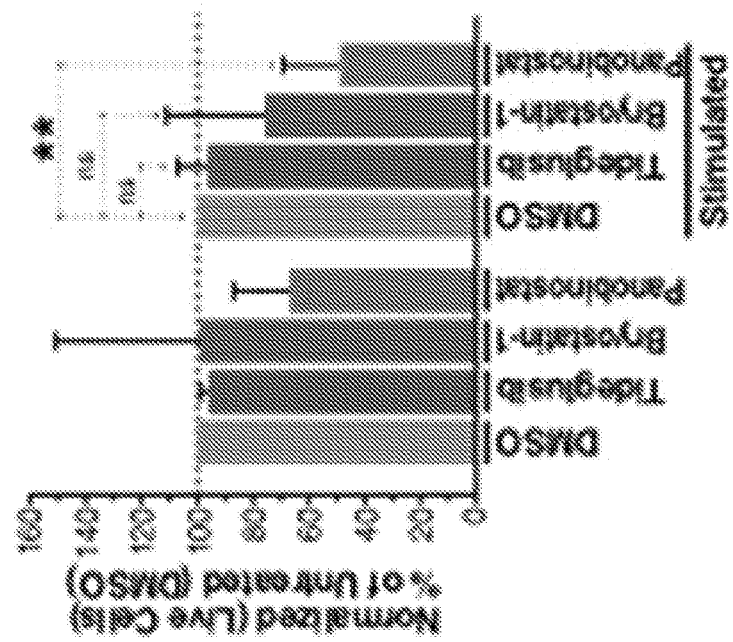
Figure 10C:
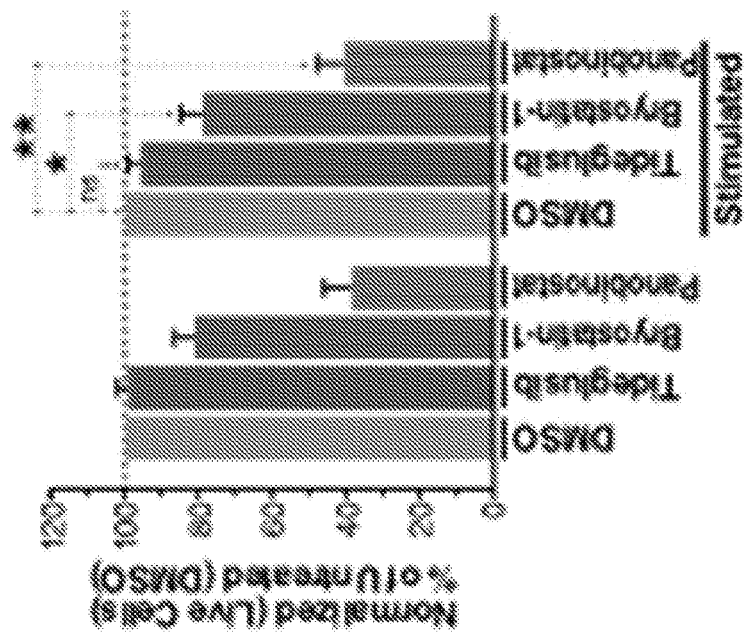
Figure 10D:
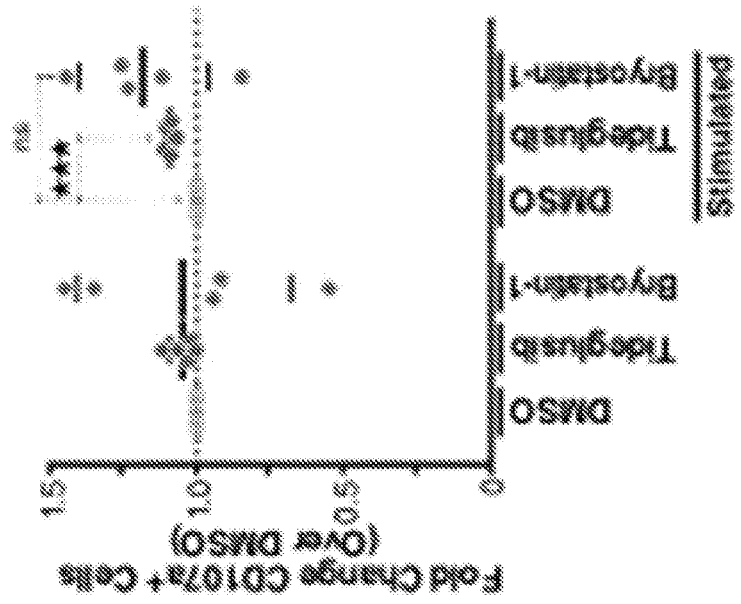
Figures 10E, 10F:
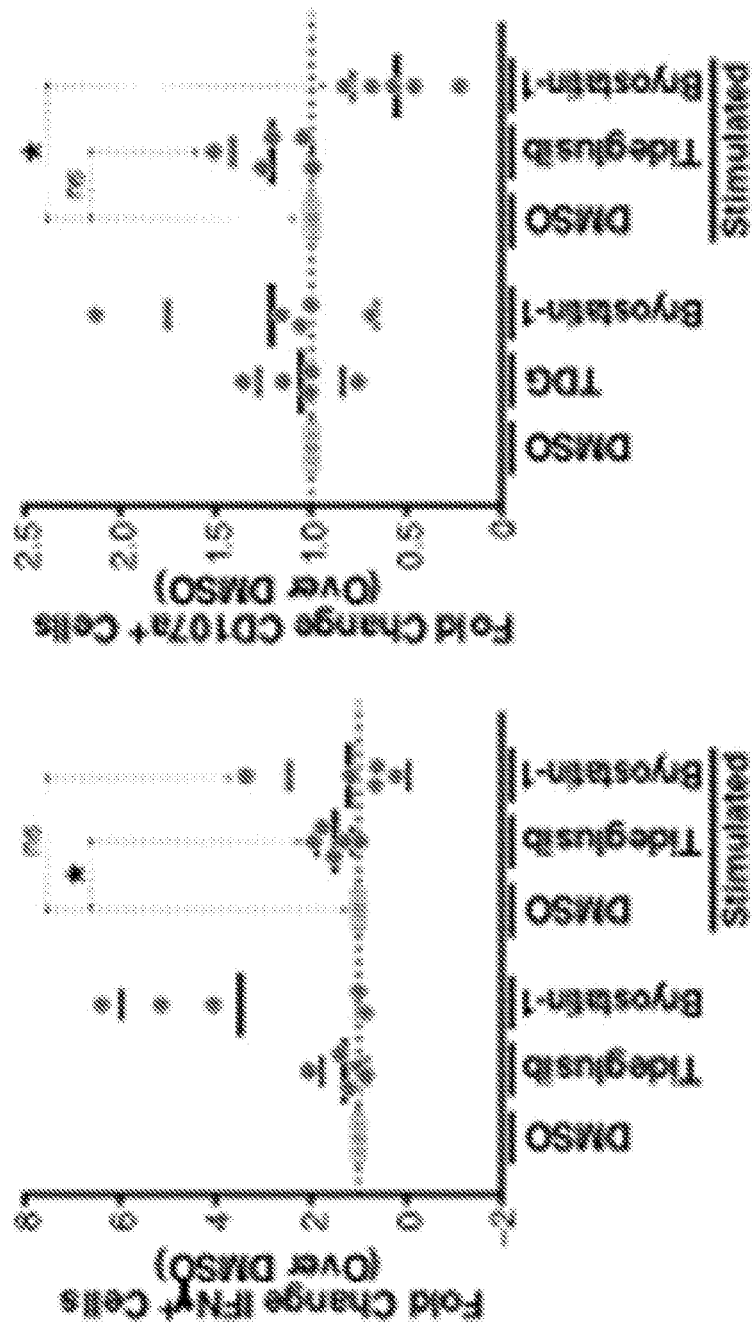
Figure 10G:
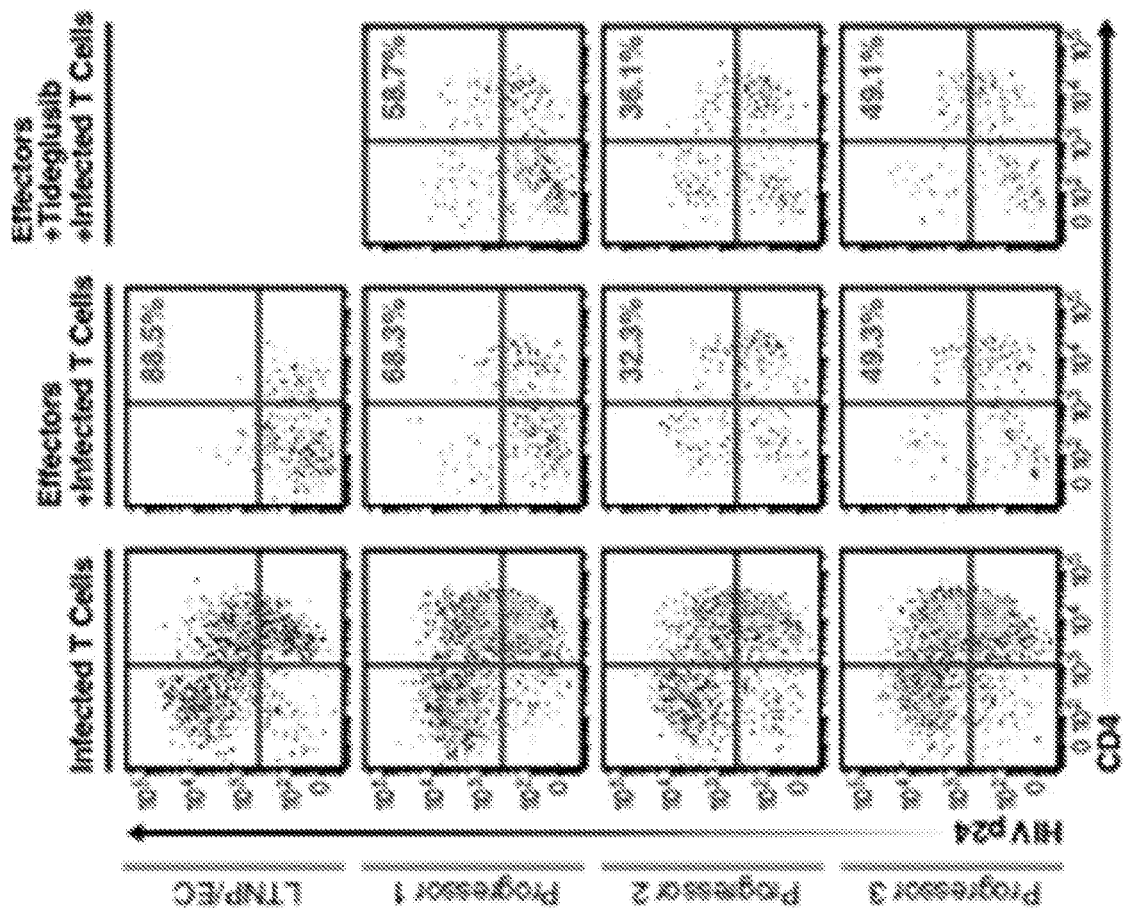
Figure 10H:
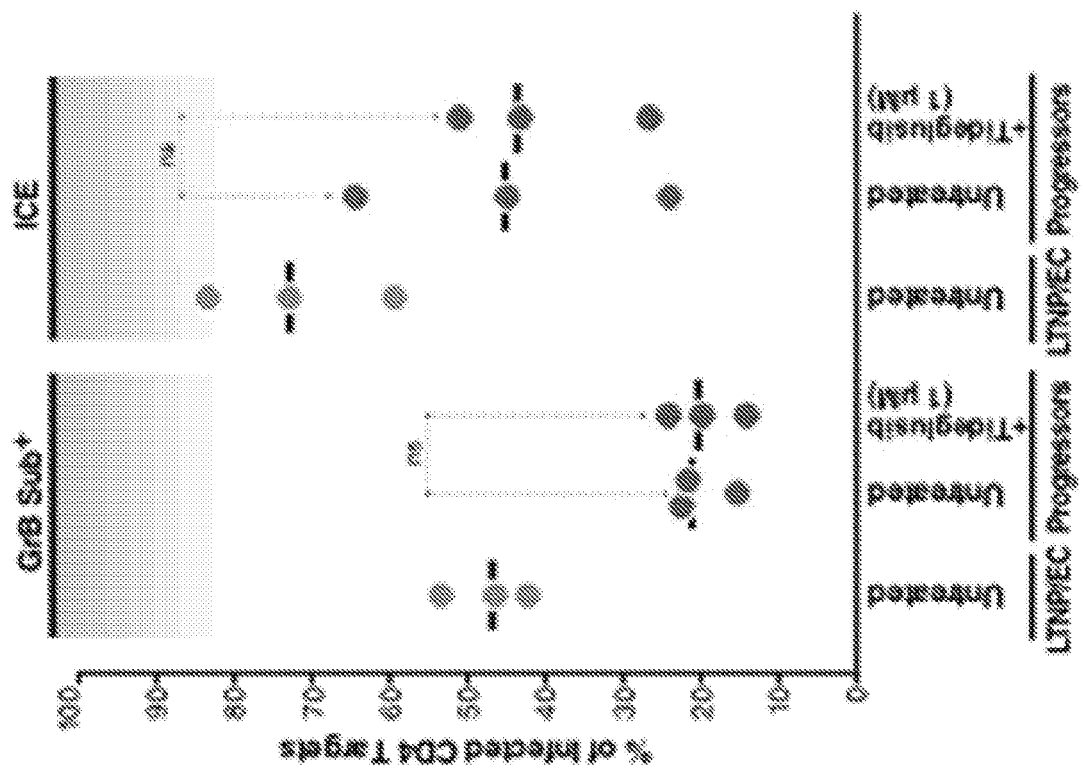

FIGS. 10A-10H demonstrate that treatment with tideglusib does not affect cytotoxic effector functions of CD8+ T, NK cells or CTL from HIV-positive donors on ART. PBMCs isolated from 5 independent HIV-negative donors were cultured in the presence of the indicated LRAs or left untreated (DMSO control) for 48 hours. Treated PBMCs were then either left unstimulated of activated in the presence of PMA/ionomycin (for CD8+ T cells in FIG. 10A, 10B, 10C) or K562 cells (for NK cells in 10D, 10E, 10F). FIG. 10A depicts normalized percentage of live CD8+ T cells shown as comparison to untreated control (DMSO=100%). FIGS. 10B and 10E depict the effect of 48 hours pre-exposure to LRAs on the frequency of CD8 T and NK cells producing IFN-γ. FIGS. 10C and 10F depict the effect of 48 hours pre-exposure to LRAs on the frequency of CD8+ T and NK cells degranulating (CD107a+). FIG. 10G provides representative plots depicting infected CD4+ T-cell elimination (ICE) of gated HIVSF162-infected CD4+ T cells after 1-hour incubation in fresh medium alone (left column) or with negatively-selected CD8+ T cells that had been initially stimulated for 6 days with HIVSF162-infected autologous CD4+ T-cell targets, without (middle column) or with (right column) tideglusib. A representative LTNP/EC (top row) and 3 participants (progressors) are shown. The total percentage of HIV-infected (p24+) cells in each plot was determined as the sum of the percentages of the upper quadrants. ICE values shown in red were calculated as follows: [(% p24 expression of infected targets only minus % p24 expression of infected targets mixed with day 6 cells) divided by % p24 expression of infected targets only] multiplied by 100. FIG. 10H depicts a summary of HIV-specific CD8+ T-cell cytotoxic responses, measured by net GrB substrate fluorescence in infected targets (background fluorescence in cultures of effectors co-incubated with uninfected targets has been subtracted) and ICE for 3 LTNP/EC (red circles) and 3 participants (progressors), which include CD8+ T cells derived from untreated (blue squares) or tideglusib-treated (teal triangles) cultures. Horizontal lines designate median values. Statistical significance was calculated using a ratio paired t test compared with each stimulated/DMSO controls (*P<0.05; P<0.005; *P<0.0005; ****P<0.00005). Error bars represent mean with standard deviation.

Figure 11A:
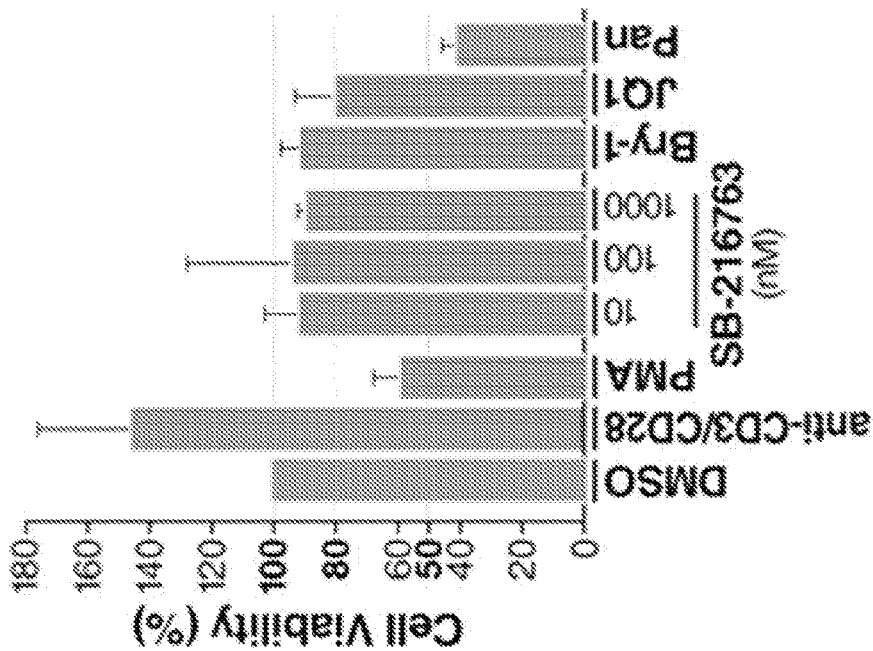
Figure 11B:
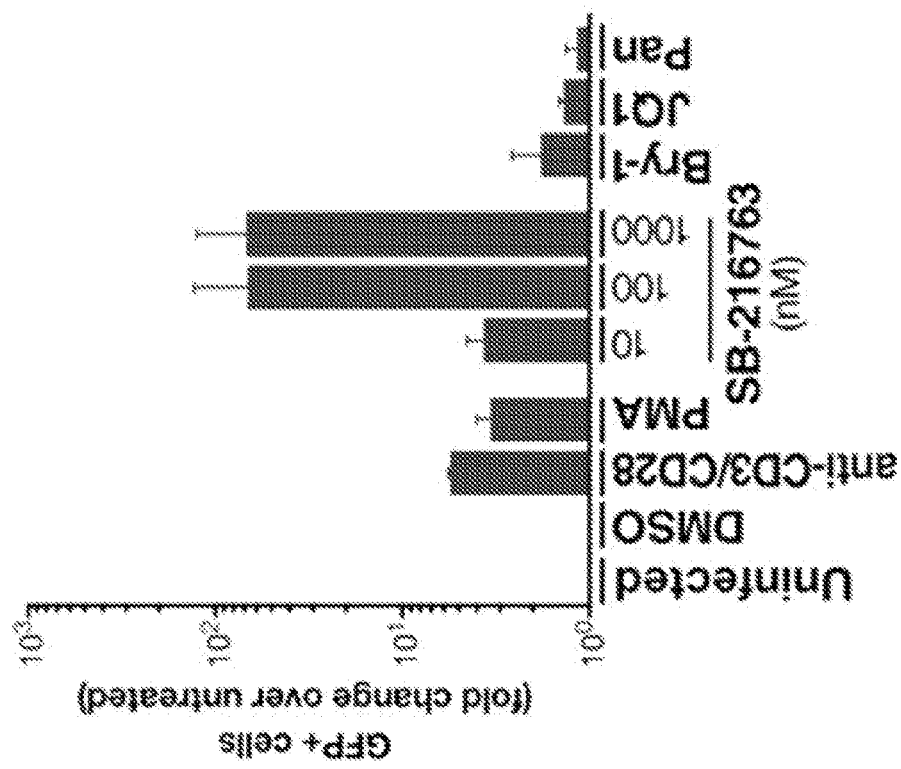

FIGS. 11A-11B depict activation of latent HIV proviruses in lymphoid tissue. FIG. 11A depicts results for primary resting CD4+ T cells isolated from tonsil tissue and spinoculated with HIV-GFP reporter viruses. After culturing for 6 days with saquinavir to prevent viral spread and to allow for death of productively infected cells, the enriched population of latently infected cells was stimulated with various LRAs, including GSK-3i, SB216763 (10-1,000 nM), phorbol 12-myristic13-acetate (PMA, 200 nM), bryostatin-1 (Bry-1, 10 nM), JQ1 (100 nM), or panobinostat (Pan, 50 nM). Cells were harvested 48 hours later and analyzed by flow cytometry. Fold stimulation of GFP expression over unstimulated is shown. FIG. 11B depicts percent cell viability in the same cultures relative to untreated cells (100%), based on Cell-Titer Blue assay. Note lack of cell death at all doses of S13216/63 but clear toxicity with PMA and panobinostat.

Figure 12:
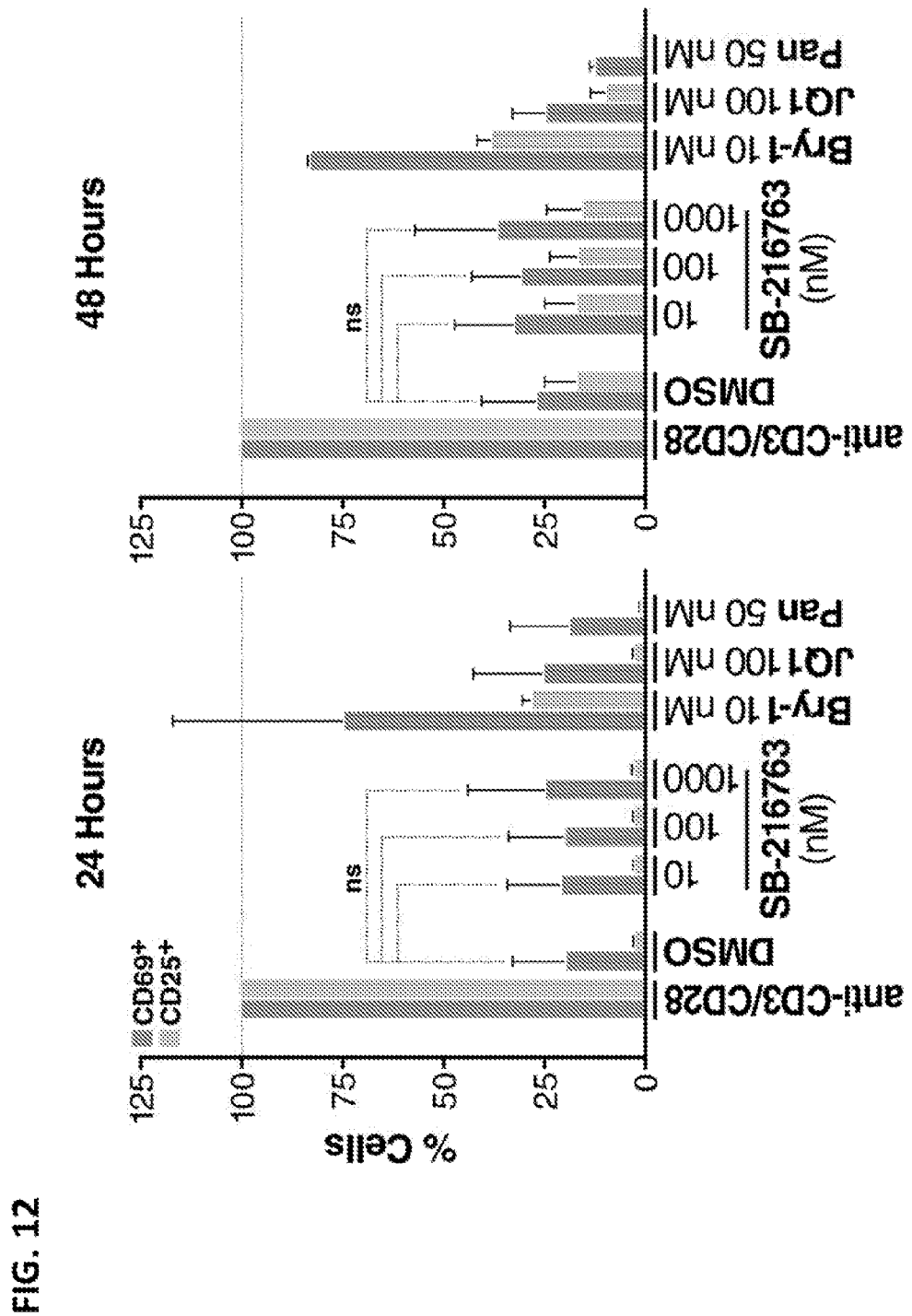

FIG. 12 depicts results for cellular activation by glycogen synthase kinase 3 inhibitor SB216763. SB216763 does not induce overt cellular activation. Cells were treated with the indicated LRAs at same concentrations shown in FIG. 11 for 24 (left panel) or 48 hours (right panel). Subsequently, cells were harvested and stained with anti-CD69 and CD25 cell activation makers, followed by flow cytometric analysis. CD69 (grey bars) and CD25 (yellow bars) expression levels were determined. Values were normalized to results obtained with anti-CD3/anti-CD28 antibodies (100%). Note lack of significant positive staining at 24 or 48 hours at all concentrations SB216763 relative to the 0.01% DMSO control.

Figure 13B:
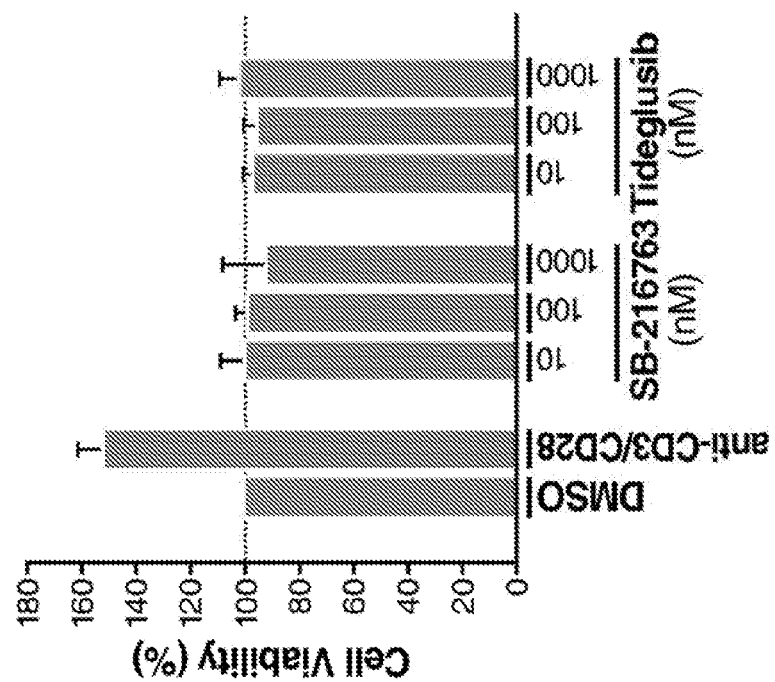
Figure 13A:
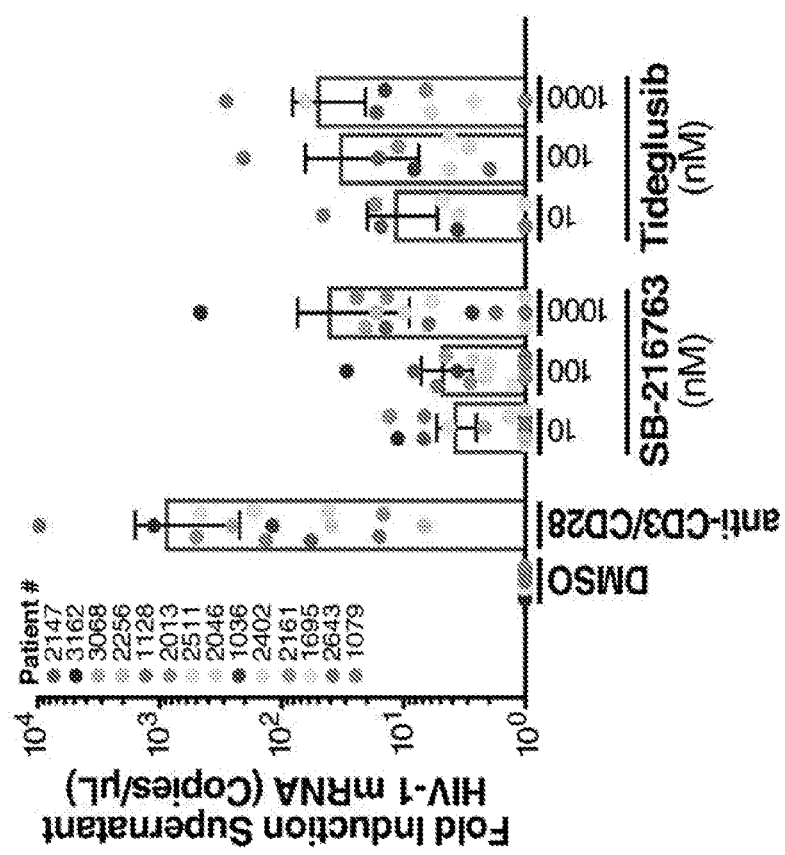
Figure 13C:
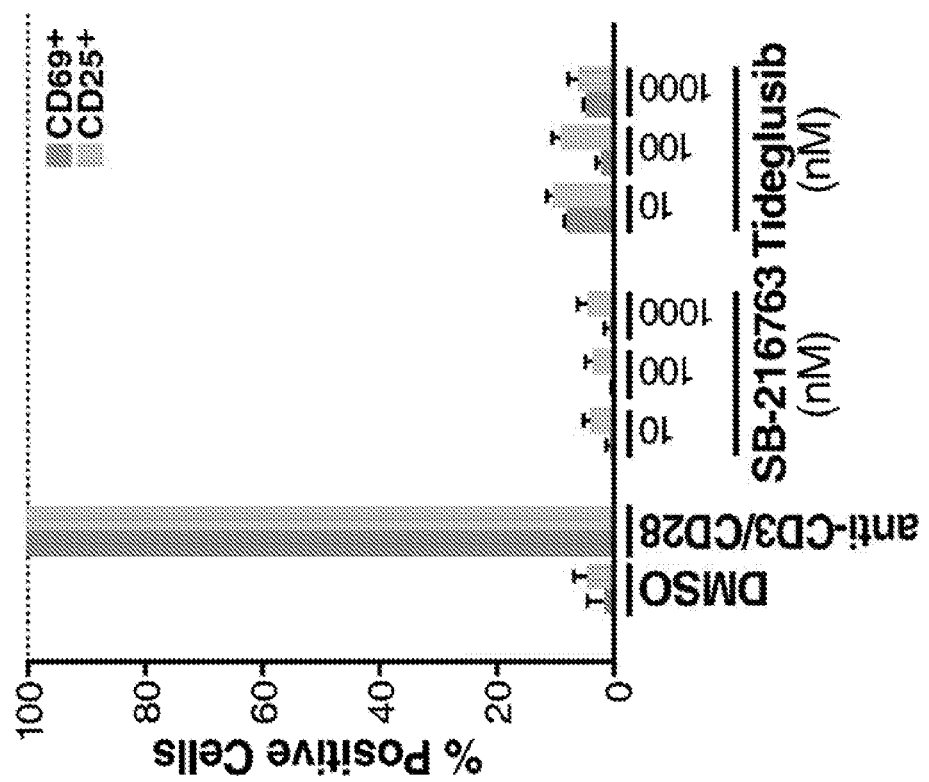

FIGS. 13A-13B depict the reversal of HIV-latency in human cells. Cells from prepared supernatants were harvested for viability testing and flow cytometric analysis. FIG. 13A depicts the Fold induction of virus-associated RNA in the supernatant of purified patient CD4+ T cells over DMSO-treated control (measured using digital droplet PCR. FIG. 13B depicts the viability of patient CD4+ T cells measured 48 h after treatment with Cell-titer blue assay. Results were normalized to the DMSO-treated control (100%). FIG. 13C depicts the patient CD4+ T cells that were harvested after treatment for 48 hours, stained with anti-CD69 or anti-CD25 or control Live (Zombie−), CD4+ T cells (CD3+/CD8−) cells were gated, and % of cells expressing CD69 or CD25 was determined and presented relative to levels in the anti-CD3/anti-CD28-treated samples (100%).

FIG. 14 provides the amino acid sequence of human glycogen synthase kinase-3α (mRNA translation).

FIG. 15 provides the amino acid sequence of human glycogen synthase kinase-3β (mRNA translation).

Definitions

The term "immunodeficiency virus" includes human immunodeficiency virus (HIV), feline immunodeficiency virus, and simian immunodeficiency virus. The term "human immunodeficiency virus" as used herein, refers to human immunodeficiency virus-1 (HIV-1); human immunodeficiency virus-2 (HIV-2); and any of a variety of HIV subtypes and quasispecies.

As used herein, the terms "treatment," "treating," and the like, refer to obtaining a desired pharmacologic and/or physiologic effect. The effect may be therapeutic in terms of a partial or complete cure for a disease and/or adverse effect attributable to the disease. "Treatment," as used herein, covers any treatment of a disease in a mammal, particularly in a human, and includes: (a) inhibiting the disease, i.e., arresting its development; and (b) relieving the disease, i.e., causing regression of the disease.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc.

A "therapeutically effective amount" or "efficacious amount" refers to the amount of a compound that, when administered to a mammal or other subject for treating a disease, is sufficient to effect such treatment for the disease. The "therapeutically effective amount" will vary depending on the compound or the cell, the disease and its severity and the age, weight, etc., of the subject to be treated.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

As used herein, a "pharmaceutical composition" is meant to encompass a composition suitable for administration to a subject, such as a mammal, especially a human. In general a "pharmaceutical composition" is sterile, and is free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intratracheal and the like. In some embodiments the composition is suitable for administration by a transdermal route, using a penetration enhancer other than dimethylsulfoxide (DMSO). In other embodiments, the pharmaceutical compositions are suitable for administration by a route other than transdermal administration. A pharmaceutical composition will in some embodiments include a subject compound and a pharmaceutically acceptable excipient. In some embodiments, a pharmaceutically acceptable excipient is other than DMSO.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and are either pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The term "solvate" as used herein refers to a complex or aggregate formed by one or more molecules of a solute, e.g. a prodrug or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

"Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent.

Definition of Select Chemical Terminology

The nomenclature of certain compounds or substituents are used in their conventional sense, such as described in chemistry literature including but not limited to Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

As used herein, the term "alkyl" by itself or as part of another substituent refers to a saturated branched or straight-chain monovalent hydrocarbon radical derived by the removal of one hydrogen atom from a single carbon atom of a parent alkane. Typical alkyl groups include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms, such as from 1 to 4 carbon atoms.

"Alkanyl" by itself or as part of another substituent refers to a saturated branched, straight-chain or cyclic alkyl radical derived by the removal of one hydrogen atom from a single carbon atom of an alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkylene" refers to a branched or unbranched saturated hydrocarbon chain, usually having from 1 to 40 carbon atoms, more usually 1 to 10 carbon atoms and even more usually 1 to 6 carbon atoms. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of an alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of an alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —$C(O)R^{30}$, where $R^{30}$ is hydrogen, alkyl, cycloalkyl, cycloheteroalkyl, aryl, arylalkyl, heteroalkyl, heteroaryl, heteroarylalkyl as defined herein and substituted versions thereof. Representative examples include, but are not limited to formyl, acetyl, cyclohexylcarbonyl, cyclohexylmethylcarbonyl, benzoyl, benzylcarbonyl, piperonyl, succinyl, and malonyl, and the like.

The term "aminoacyl" refers to the group —$C(O)NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Alkoxy" by itself or as part of another substituent refers to a radical —$OR^{31}$ where $R^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical —$C(O)OR^{31}$ where $R^{31}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of an aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group comprises from 6 to 20 carbon atoms. In certain embodiments, an aryl group comprises from 6 to 12 carbon atoms. Examples of an aryl group are phenyl and naphthyl.

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In certain embodiments, an arylalkyl group is $(C_7-C_{30})$ arylalkyl, e.g., the alkanyl, alkenyl or alkynyl moiety of the arylalkyl group is $(C_1-C_{10})$ and the aryl moiety is $(C_6-C_{20})$. In certain embodiments, an arylalkyl group is $(C_7-C_{20})$ arylalkyl, e.g., the alkanyl, alkenyl or alkynyl moiety of the arylalkyl group is $(C_1-C_8)$ and the aryl moiety is $(C_6-C_{12})$.

"Arylaryl" by itself or as part of another substituent, refers to a monovalent hydrocarbon group derived by the removal of one hydrogen atom from a single carbon atom of a ring system in which two or more identical or non-identical aromatic ring systems are joined directly together by a single bond, where the number of such direct ring junctions is one less than the number of aromatic ring systems involved. Typical arylaryl groups include, but are not limited to, biphenyl, triphenyl, phenyl-napthyl, binaphthyl, biphenylnapthyl, and the like. When the number of carbon atoms in an arylaryl group are specified, the numbers refer to the carbon atoms comprising each aromatic ring. For example, $(C_5-C_{14})$ arylaryl is an arylaryl group in which each aromatic ring comprises from 5 to 14 carbons, e.g., biphenyl, triphenyl, binaphthyl, phenylnapthyl, etc. In certain embodiments, each aromatic ring system of an arylaryl group is independently a $(C_5-C_{14})$ aromatic. In certain embodiments, each aromatic ring system of an arylaryl group is independently a $(C_5-C_{10})$ aromatic. In certain embodiments, each aromatic ring system is identical, e.g., biphenyl, triphenyl, binaphthyl, trinaphthyl, etc.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. In certain embodiments, the cycloalkyl group is $(C_3-C_{10})$ cycloalkyl. In certain embodiments, the cycloalkyl group is $(C_3-C_7)$ cycloalkyl.

"Cycloheteroalkyl" or "heterocyclyl" by itself or as part of another substituent, refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —S—S—, —O—S—, —NR$^{37}$R$^{38}$—, =N—N=, —N=N—, —N=N—NR$^{39}$R$^{40}$, —PR$^{41}$—, —P(O)$_2$—, —POR$^{42}$—, —O—P(O)$_2$—, —S—O—, —S—(O)—, —SO$_2$—, —SnR$^{43}$R$^{44}$— and the like, where R$^{37}$, R$^{38}$, R$^{39}$, R$^{40}$, R$^{41}$, R$^{42}$, R$^{43}$ and R$^{44}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl and/or heterorylalkynyl is used. In certain embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In certain embodiments, the heteroarylalkyl group is 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Aromatic Ring System" by itself or as part of another substituent, refers to an unsaturated cyclic or polycyclic ring system having a conjugated π electron system. Specifically included within the definition of "aromatic ring system" are fused ring systems in which one or more of the rings are aromatic and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Heteroaromatic Ring System" by itself or as part of another substituent, refers to an aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Substituted" refers to a group in which one or more hydrogen atoms are independently replaced with the same or different substituent(s). Typical substituents include, but are not limited to, alkylenedioxy (such as methylenedioxy), -M, $-R^{60}$, $-O^-$, $=O$, $-OR^{60}$, $-SR^{60}$, $-S^-$, $=S$, $-NR^{60}R^{61}$, $=NR^{60}$, $-CF_3$, $-CN$, $-OCN$, $-SCN$, $-NO$, $-NO_2$, $=N_2$, $-N_3$, $-S(O)_2O-$, $-S(O)_2OH$, $-S(O)_2R^{60}$, $-OS(O)_2O-$, $-OS(O)_2R^{60}$, $-P(O)(O^-)_2$, $-P(O)(OR^{60})(O^-)$, $-OP(O)(OR^{60})(OR^{61})$, $-C(O)R^{60}$, $-C(S)R^{60}$, $-C(O)OR^{60}$, $-C(O)NR^{60}R^{61}$, $-C(O)O^-$, $-C(S)OR^{60}$, $-NR^{62}C(O)NR^{60}R^{61}$, $-R^{62}C(S)NR^{60}R^{61}$, $-R^{62}C(R^{63})NR^{60}R^{61}$ and $-C(NR^{62})NR^{60}R^{61}$ where M is halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. In certain embodiments, substituents include -M, $-R^{60}$, $=O$, $-OR^{60}$, $-SR^{60}$, $-S^-$, $=S$, $-NR^{60}R^{61}$, $=NR^{60}$, $-CF_3$, $-CN$, $-OCN$, $-SCN$, $-NO$, $-NO_2$, $=N_2$, $-N_3$, $-S(O)_2R^{60}$, $-OS(O)_2O^-$, $-OS(O)_2R^{60}$, $-P(O)(O^-)_2$, $-P(O)(OR^{60})(O')$, $-OP(O)(OR^{60})(OR^{61})$, $-C(O)R^{60}$, $-C(S)R^{60}$, $-C(O)$ $OR^{60}$, $-C(O)NR^{60}R^{61}$, $-C(O)O^-$, $-NR^{62}C(O)NR^{60}R^{61}$. In certain embodiments, substituents include -M, $-R^{60}$, $=O$, $-OR^{60}$, $-SR^{60}$, $-NR^{60}R^{61}$, $-CF_3$, $-CN$, $-NO_2$, $-S(O)_2R^{60}$, $-P(O)(OR^{60})(O^-)$, $-OP(O)(OR^{60})(OR^{61})$, $-C(O)R^{60}$, $-C(O)OR^{60}$, $-C(O)NR^{60}R^{61}$, $-C(O)O^-$. In certain embodiments, substituents include -M, $-R^{60}$, $=O$, $-OR^{60}$, $-SR^{60}$, $NR^{60}R^{61}$, $-CF_3$, $-CN$, $-NO_2$, $-S(O)_2R^{60}$, $-OP(O)(O R^{60})(OR^{61})$, $-C(O)R^{60}$, $-C(O)OR^{60}$, $-C(O)O-$, where $R^{60}$, $R^{61}$ and $R^{62}$ are as defined above. For example, a substituted group may bear a methylenedioxy substituent or one, two, or three substituents selected from a halogen atom, a (1-4C)alkyl group and a (1-4C)alkoxy group.

The compounds described herein can contain one or more chiral centers and/or double bonds and therefore, can exist as stereoisomers, such as double-bond isomers (i.e., geometric isomers), enantiomers or diastereomers. Accordingly, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^2H$, $^3H$, $^{11}C$, $^{13}C$, $^{14}C$, $^{15}N$, $^{18}O$, $^{17}O$, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited. To the extent the disclosure or definition of any publication incorporated by reference herein conflicts with that of the present disclosure, the present disclosure shall control.

It must be noted that as used herein and in the appended claims, the singular forms "a," "an," and "the" include plural referents unless the context clearly dictates otherwise. Thus, for example, reference to "a GSK 3β antagonist" includes a plurality of such antagonist compounds and reference to "the HIV-infected cell" includes reference to one or more HIV-infected cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication. Further, the dates of publication provided may be different from the actual publication dates which may need to be independently confirmed.

DETAILED DESCRIPTION

The present disclosure provides methods of reactivating latent HIV integrated into the genome of an HIV-infected cell. The present disclosure provides methods for reducing the reservoir of latent immunodeficiency virus in vitro and in vivo. The methods generally involve contacting an HIV-infected cell in which HIV is latent with a compound that suppresses or inhibits the action of one or more of the different isoforms of the serine/threonine kinase glycogen synthase kinase 3, such as for example a glycogen synthase kinase 3α inhibitor or a glycogen synthase kinase 3β inhibitor.

In some embodiments, the methods involve contacting an HIV-infected cell in which HIV is latent with a glycogen synthase kinase 3β (GSK-3β) antagonist of Formula I, e.g., Tideglusib (4-benzyl-2-(naphthalen-1-yl)-1,2,4-thiadiazolidine-3,5-dione) or a pharmaceutically acceptable salt or derivative thereof.

In other embodiments, the methods generally involve contacting an HIV-infected cell in which HIV is latent with a maleimide-based glycogen synthase kinase 3 antagonist of Formula II, e.g., SB-216763 (3-(2,4-Dichlorophenyl)-4-(1-methyl-1H-indol-3-yl)-1H-pyrrole-2,5-dione) or a pharmaceutically acceptable salt or derivative thereof. The maleimide-based glycogen synthase kinase 3 antagonist of Formula II may be a glycogen synthase kinase 3α and/or 3β inhibitor.

The present disclosure further provides detection methods for identifying a cell that has latent HIV. The methods generally involve contacting a cell obtained from an individual with a glycogen synthase kinase 3 inhibitor, such as a compound of Formula I, e.g., Tideglusib or a pharmaceutically acceptable salt or derivative thereof or a compound of Formula II, e.g., SB-216763 or a pharmaceutically acceptable salt or derivative thereof, and detecting expression of an HIV-encoded gene product. If the cell expresses an HIV-encoded gene product when contacted with a glycogen synthase kinase 3 inhibitor, such as a compound of Formula I, e.g., Tideglusib or a pharmaceutically acceptable salt or derivative thereof or a compound of Formula II, e.g., SB-216763 or a pharmaceutically acceptable salt or derivative thereof, but does not express detectable levels of the HIV-encoded gene product in the absence of the glycogen synthase kinase 3 inhibitor (e.g., the compound of Formula I, e.g., Tideglusib or the pharmaceutically acceptable salt or derivative thereof or compound of Formula II, e.g., SB-216763 or a pharmaceutically acceptable salt or derivative thereof), the cell is considered to have latent HIV.

The present disclosure further provides a method of identifying a candidate agent for treating an HIV infection in an individual. The method generally involves contacting a primary cell, e.g., a primary cell identified using a subject method, with a glycogen synthase kinase 3 inhibitor, such as a compound of Formula I, e.g., Tideglusib or a pharmaceutically acceptable salt or derivative thereof or a compound of Formula II, e.g., SB-216763, and a test agent; and determining the effect of the test agent on the level of HIV produced in the cell. A test agent that reduces the level of HIV produced in the cell, compared to the level of HIV produced in a control cell contacted with the glycogen synthase kinase 3 inhibitor (e.g., a compound of Formula I, e.g., Tideglusib or the pharmaceutically acceptable salt or derivative thereof or a compound of Formula II, e.g., SB-216763), but not with the test agent, is considered a candidate agent for inhibiting HIV and treating an HIV infection.

Treatment Methods

The present disclosure provides methods for reactivating latent immunodeficiency virus in a cell, the methods generally involving contacting the cell with a glycogen synthase kinase 3 inhibitor, such as a compound of Formula I, e.g., Tideglusib or a pharmaceutically acceptable salt or derivative thereof, or a compound of Formula II, e.g., SB-216763 or a pharmaceutically acceptable salt or derivative thereof. The present disclosure provides methods for reducing the reservoir of latent immunodeficiency virus in an individual by administering to the individual an effective amount of a glycogen synthase kinase 3 inhibitor, such as a compound of Formula I, e.g., Tideglusib or a pharmaceutically acceptable salt or derivative thereof, or a compound of Formula II, e.g., SB-216763 or a pharmaceutically acceptable salt or derivative thereof. The present disclosure provides methods of treating an immunodeficiency virus infection in an individual, the methods generally involving co-administering to the individual a glycogen synthase kinase 3 inhibitor, such as a compound of Formula I, e.g., Tideglusib or a pharmaceutically acceptable salt or derivative thereof, or a compound of Formula II, e.g., SB-216763 or a pharmaceutically acceptable salt or derivative thereof, and an anti-HIV agent.

In some embodiments, an effective amount of the glycogen synthase kinase 3 inhibitor (e.g., a compound of Formula I, e.g., Tideglusib or a pharmaceutically acceptable salt or derivative thereof, or a compound of Formula II, e.g., SB-216763 or a pharmaceutically acceptable salt thereof) is an amount that reactivates latent HIV and reduces the reservoir of latent HIV in an individual by at least about 20%, at least about 30%, at least about 40%, at least about 50%, at least about 60%, at least about 70%, at least about 80%, or at least about 90%. A "reduction in the reservoir of latent HIV" (also referred to as "reservoir of latently infected cells") is a reduction in the number of cells in the individual that harbor a latent HIV infection. Whether the reservoir of latently infected cells is reduced can be determined using any known method, including the method described in Blankson et al. (2000) *J. Infect. Disease* 182(6):1636-1642.

In some embodiments, a subject method of treating an immunodeficiency virus infection in an individual in need thereof involves: a) administering to the individual an effective amount of a glycogen synthase kinase 3 inhibitor (e.g., a compound of Formula I, e.g., Tideglusib or a pharmaceutically acceptable salt or derivative thereof, or a compound of Formula II, e.g., SB-216763 or a pharmaceutically acceptable salt or derivative thereof; and b) administering to the individual an effective amount of an agent that inhibits an immunodeficiency virus function. The immunodeficiency virus function can be selected from viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity.

In some embodiments, a glycogen synthase kinase 3 inhibitor (e.g., a compound of Formula I, e.g., Tideglusib or a pharmaceutically acceptable salt or derivative thereof, or a compound of Formula II, e.g., SB-216763 or a pharmaceutically acceptable salt or derivative thereof) is administered in a combination therapy (i.e., co-administered) with: 1) one or more nucleoside reverse transcriptase inhibitors (e.g., Combivir, Epivir, Hivid, Retrovir, Videx, Zerit, Ziagen, etc.); 2) one or more non-nucleoside reverse transcriptase inhibitors (e.g., Rescriptor, Sustiva, Viramune, etc.); 3) one or more protease inhibitors (e.g., Agenerase, Crixivan, Fortovase, Invirase, Kaletra, Norvir, Viracept, etc.); 4) an anti-HIV agent such as a protease inhibitor and a nucleoside reverse transcriptase inhibitor; 5) an anti-HIV agent such as a protease inhibitor, a nucleoside reverse transcriptase inhibitor, and a non-nucleoside reverse transcriptase inhibitor; 6) an anti-HIV agent such as a protease inhibitor and a non-nucleoside reverse transcriptase inhibitor, and/or 7) an anti-viral (e.g., HIV) agent such as a protein kinase C (PKC) activator (e.g., prostratin). Other combinations of an effective amount of a glycogen synthase kinase 3 inhibitor (e.g., a compound of Formula I, e.g., Tideglusib or a pharmaceutically acceptable salt or derivative thereof, or a compound of Formula II, e.g., SB216763 or a pharmaceutically acceptable salt or derivative thereof), with one or more anti-HIV agents, such as one or more of a protease inhibitor, a nucleoside reverse transcriptase inhibitor, a non-nucleoside reverse transcriptase inhibitor, and a protein kinase C (PKC) activator are contemplated.

A PKC activator (e.g., prostratin ((1aR,1bS,4aR,7aS,7bR,8R,9aS)-4a,7b-dihydroxy-3-(hydroxymethyl)-1,1,6,8-tetramethyl-5-oxo-1,1a,1b,4,4a,5,7a,7b,8,9-decahydro-9aH-cyclopropa[3,4]benzo[1,2-e]azulen-9a-yl)) can be administered in a separate formulation from a glycogen synthase kinase 3 inhibitor (e.g., a compound of Formula I, e.g., Tideglusib or a pharmaceutically acceptable salt or derivative thereof or a compound of Formula II, e.g., SB-216763 or a pharmaceutically acceptable salt or derivative thereof). A PKC activator can be co-formulated with a glycogen synthase kinase 3 inhibitor (e.g., a compound of Formula I, e.g., Tideglusib or a pharmaceutically acceptable salt or derivative thereof or a compound of Formula II, e.g., SB-216763 or a pharmaceutically acceptable salt or derivative thereof), and the co-formulation administered to an individual.

Any of a variety of methods can be used to determine whether a treatment method is effective. For example, methods of determining whether the methods of the invention are effective in reducing immunodeficiency virus (e.g., HIV) viral load, and/or treating an immunodeficiency virus (e.g., HIV) infection, are any known test for indicia of immunodeficiency virus (e.g., HIV) infection, including, but not limited to, measuring viral load, e.g., by measuring the amount of immunodeficiency virus (e.g., HIV) in a biological sample, e.g., using a polymerase chain reaction (PCR) with primers specific for an immunodeficiency virus (e.g., HIV) polynucleotide sequence; detecting and/or measuring a polypeptide encoded by an immunodeficiency virus (e.g., HIV), e.g., p24, gp120, reverse transcriptase, using, e.g., an immunological assay such as an enzyme-linked immunosorbent assay (ELISA) with an antibody specific for the polypeptide; and measuring the CD4$^+$ T cell count in the individual.

Glycogen Synthase Kinase 3α and/or 3β Antagonists and Pharmaceutically Acceptable Salts and Derivatives Thereof Compounds of Formula I The compositions of the present disclosure include compounds of Formula I, shown below, which formula encompasses Tideglusib (4-benzyl-2-(naphthalen-1-yl)-1,2,4-thiadiazolidine-3,5-dione) and pharmaceutically acceptable salts and derivatives thereof. Pharmaceutical compositions and methods of the present disclosure also contemplate compounds of Formula I.

In one of its composition aspects, the present embodiments provide a compound of Formula I:

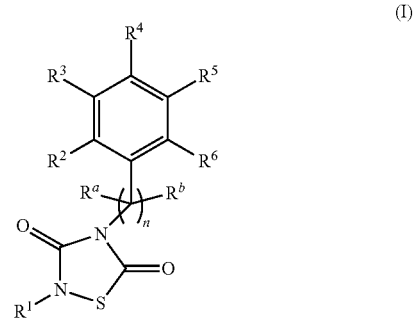

or a pharmaceutically acceptable salt, solvate or prodrug thereof, wherein:

n is an integer from 1 to 8; and each of $R^1$, $R^2$, $R^3$, $R^4$, $R^5$, $R^6$, $R^a$ and $R^b$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, —COR$^7$, —C(O)OR$^7$, —C(O)NR$^7$R$^8$, —C=NR$^7$, —OR$^7$, —OC(O)R$^7$, —S(O)$_t$—R$^7$, —NR$^7$R$^8$, —NR$^7$C(O)R$^8$, —N=CR$^7$R$^8$, wherein t is 0, 1, 2 or 3 and $R^7$ and $R^8$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen.

In some embodiments, n is 1. In other embodiments, n is 2. In other embodiments, n is 3. In other embodiments, n is 4. In other embodiments, n is 5. In other embodiments, n is 6. In other embodiments, n is 7. In other embodiments, n is 8.

In some embodiments, $R^1$ is hydrogen. In other embodiments, $R^1$ is alkyl or substituted alkyl. In other embodiments, $R^1$ is aryl or substituted aryl. In other embodiments, $R^1$ is heterocycloalkyl or substituted heterocycloalkyl. In other embodiments, $R^1$ is heteroaryl or substituted heteroaryl. In other embodiments, $R^1$ is hydroxyl, alkoxyl or substituted alkoxyl. In other embodiments, $R^1$ is acyloxy or substituted acyloxy. In other embodiments, $R^1$ is alkoxylcarbonyl or substituted alkoxycarbonyl. In other embodiments, $R^1$ is acyl or substituted acyl. In other embodiments, $R^1$ is thiol. In other embodiment, $R^1$ is amino or substituted amino. In other embodiments, $R^1$ is aminoacyl or substituted aminoacyl. In other embodiments, $R^1$ is azido. In other embodiments, $R^1$ is carboxyl, substituted carboxyl, carboxyalkyl or substituted carboxyalkyl. In other embodiments, $R^1$ is cyano. In other embodiments, $R^1$ is a halogen, such as —F, —Cl, —Br and —I. In other embodiments, $R^1$ is nitro. In certain embodiments, $R^1$ is naphthyl.

In some embodiments, $R^2$ is hydrogen. In other embodiments, $R^2$ is alkyl or substituted alkyl. In other embodiments, $R^2$ is aryl or substituted aryl. In other embodiments, $R^2$ is heterocycloalkyl or substituted heterocycloalkyl. In other embodiments, $R^2$ is heteroaryl or substituted heteroaryl. In other embodiments, $R^2$ is hydroxyl, alkoxyl or substituted alkoxyl. In other embodiments, $R^2$ is acyloxy or substituted acyloxy. In other embodiments, $R^2$ is alkoxylcarbonyl or substituted alkoxycarbonyl. In other embodiments, $R^2$ is acyl or substituted acyl. In other embodiments, $R^2$ is thiol. In other embodiment, $R^2$ is amino or substituted amino. In other embodiments, $R^2$ is aminoacyl or substituted aminoacyl. In other embodiments, $R^2$ is azido. In other embodiments, $R^2$ is carboxyl, substituted carboxyl, carboxyalkyl or substituted carboxyalkyl. In other embodiments, $R^2$ is cyano. In other embodiments, $R^2$ is a halogen, such as —F, —Cl, —Br and —I. In other embodiments, $R^2$ is nitro.

In some embodiments, $R^3$ is hydrogen. In other embodiments, $R^3$ is alkyl or substituted alkyl. In other embodiments, $R^3$ is aryl or substituted aryl. In other embodiments, $R^3$ is heterocycloalkyl or substituted heterocycloalkyl. In other embodiments, $R^3$ is heteroaryl or substituted heteroaryl. In other embodiments, $R^3$ is hydroxyl, alkoxyl or substituted alkoxyl. In other embodiments, $R^3$ is acyloxy or substituted acyloxy. In other embodiments, $R^3$ is alkoxylcarbonyl or substituted alkoxycarbonyl. In other embodiments, $R^3$ is acyl or substituted acyl. In other embodiments, $R^3$ is thiol. In other embodiment, $R^3$ is amino or substituted amino. In other embodiments, $R^3$ is aminoacyl or substituted aminoacyl. In other embodiments, $R^3$ is azido. In other embodiments, $R^3$ is carboxyl, substituted carboxyl, carboxyalkyl or substituted carboxyalkyl. In other embodiments, $R^3$ is cyano. In other embodiments, $R^3$ is a halogen, such as —F, —Cl, —Br and —I. In other embodiments, $R^3$ is chloro.

In some embodiments, $R^4$ is hydrogen. In other embodiments, $R^4$ is alkyl or substituted alkyl. In other embodiments, $R^4$ is aryl or substituted aryl. In other embodiments, $R^4$ is heterocycloalkyl or substituted heterocycloalkyl. In other embodiments, $R^4$ is heteroaryl or substituted heteroaryl. In other embodiments, $R^4$ is hydroxyl, alkoxyl or substituted alkoxyl. In other embodiments, $R^4$ is acyloxy or substituted acyloxy. In other embodiments, $R^4$ is alkoxylcarbonyl or substituted alkoxycarbonyl. In other embodiments, $R^4$ is acyl or substituted acyl. In other embodiments, $R^4$ is thiol. In other embodiment, $R^4$ is amino or substituted amino. In other embodiments, $R^4$ is aminoacyl or substituted aminoacyl. In other embodiments, $R^4$ is azido. In other embodiments, $R^4$ is carboxyl, substituted carboxyl, carboxyalkyl or substituted carboxyalkyl. In other embodiments, $R^4$ is cyano. In other embodiments, $R^4$ is a halogen, such as —F, —Cl, —Br and —I. In other embodiments, $R^4$ is nitro.

In some embodiments, $R^5$ is hydrogen. In other embodiments, $R^5$ is alkyl or substituted alkyl. In other embodiments, $R^5$ is aryl or substituted aryl. In other embodiments, $R^5$ is heterocycloalkyl or substituted heterocycloalkyl. In other embodiments, $R^5$ is heteroaryl or substituted heteroaryl. In other embodiments, $R^5$ is hydroxyl, alkoxyl or substituted alkoxyl. In other embodiments, $R^5$ is acyloxy or substituted acyloxy. In other embodiments, $R^5$ is alkoxylcarbonyl or substituted alkoxycarbonyl. In other embodiments, $R^5$ is acyl or substituted acyl. In other embodiments, $R^5$ is thiol. In other embodiment, $R^5$ is amino or substituted amino. In other embodiments, $R^5$ is aminoacyl or substituted aminoacyl. In other embodiments, $R^5$ is azido. In other embodiments, $R^5$ is carboxyl, substituted carboxyl, carboxyalkyl or substituted carboxyalkyl. In other embodiments, $R^5$ is cyano. In other embodiments, $R^5$ is a halogen, such as —F, —Cl, —Br and —I. In other embodiments, $R^5$ is nitro.

In some embodiments, $R^6$ is hydrogen. In other embodiments, KR is alkyl or substituted alkyl. In other embodiments, $R^6$ is aryl or substituted aryl. In other embodiments, $R^6$ is heterocycloalkyl or substituted heterocycloalkyl. In other embodiments, $R^6$ is heteroaryl or substituted heteroaryl. In other embodiments, $R^6$ is hydroxyl, alkoxyl or substituted alkoxyl. In other embodiments, $R^6$ is acyloxy or substituted acyloxy. In other embodiments, $R^6$ is alkoxylcarbonyl or substituted alkoxycarbonyl. In other embodiments, $R^6$ is acyl or substituted acyl. In other embodiments, $R^6$ is thiol. In other embodiment, $R^6$ is amino or substituted amino. In other embodiments, $R^6$ is aminoacyl or substituted aminoacyl. In other embodiments, $R^6$ is azido. In other embodiments, $R^6$ is carboxyl, substituted carboxyl, carboxyalkyl or substituted carboxyalkyl. In other embodiments, $R^6$ is cyano. In other embodiments, $R^6$ is a halogen, such as —F, —Cl, —Br and —I. In other embodiments, $R^6$ is nitro. In certain embodiments, $R^6$ is alkoxylcarbonyl, such as ethoxycarbonyl.

In some embodiments, $R^7$ is hydrogen. In other embodiments, $R^7$ is alkyl or substituted alkyl. In other embodiments, $R^7$ is aryl or substituted aryl. In other embodiments, $R^7$ is heterocycloalkyl or substituted heterocycloalkyl. In other embodiments, $R^7$ is heteroaryl or substituted heteroaryl. In other embodiments, $R^7$ is hydroxyl, alkoxyl or substituted alkoxyl. In other embodiments, $R^7$ is acyloxy or substituted acyloxy. In other embodiments, $R^7$ is alkoxylcarbonyl or substituted alkoxycarbonyl. In other embodiments, $R^7$ is acyl or substituted acyl. In other embodiments, $R^7$ is thiol. In other embodiment, $R^7$ is amino or substituted amino. In other embodiments, $R^7$ is aminoacyl or substituted aminoacyl. In other embodiments, $R^7$ is azido. In other embodiments, $R^7$ is carboxyl, substituted carboxyl, carboxyalkyl or substituted carboxyalkyl. In other embodiments, $R^7$ is cyano. In other embodiments, $R^7$ is a halogen, such as —F, —Cl, —Br and —I. In other embodiments, $R^7$ is nitro. In certain embodiments, $R^7$ is amino.

In certain embodiments, a compound of interest and salts or solvates or stereoisomers thereof, include:

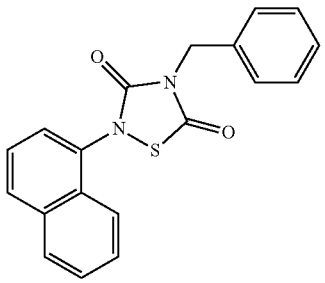 [SMILES: O=c1sn(-c2cccc3ccccc23)c(=O)n1Cc1ccccc1]

("Tideglusib") (4-benzyl-2-(naphthalen-1-yl)-1,2,4-thiadiazolidine-3,5-dione).

Compounds of Formula II

The compositions of the present disclosure include compounds of Formula II, shown below, which formula encompasses SB-216763 (3-(2,4-Dichlorophenyl)-4-(1-methyl-1H-indol-3-yl)-1H-pyrrole-2,5-dione) and pharmaceutically acceptable salts and derivatives thereof. Pharmaceutical compositions and methods of the present disclosure also contemplate compounds of Formula II.

In one of its composition aspects, the present embodiments provide a compound of Formula II:

Formula II

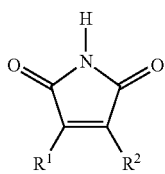

or a pharmaceutically acceptable salt, solvate or prodrug thereof, wherein:

$R^1$ and $R^2$ are independently $C_5$-$C_{12}$ cycloalkyl, substituted $C_5$-$C_{12}$ cycloalkyl, $C_5$-$C_{12}$ heterocycloalkyl, substituted $C_5$-$C_{12}$ heterocycloalkyl, $C_5$-$C_{12}$ aryl, substituted $C_5$-$C_{12}$ aryl, $C_5$-$C_{12}$ heteroaryl, substituted $C_5$-$C_{12}$ heteroaryl.

In some embodiments, the compound of Formula II is a compound of Formula IIa:

Formula IIa

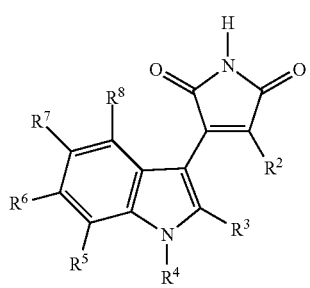

or a pharmaceutically acceptable salt, solvate or prodrug thereof, wherein:

$R^2$ are independently $C_5$-$C_{12}$ cycloalkyl, substituted $C_5$-$C_{12}$ cycloalkyl, $C_5$-$C_{12}$ heterocycloalkyl, substituted $C_5$-$C_{12}$ heterocycloalkyl, $C_5$-$C_{12}$ aryl, substituted $C_5$-$C_{12}$ aryl, $C_5$-$C_{12}$ heteroaryl, substituted $C_5$-$C_{12}$ heteroaryl;

each of $R^3$, $R^4$, $R^5$, $R^6$, $R^7$ and $R^8$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, —COR$^7$, —C(O)OR$^7$, —C(O)NR$^7$R$^8$, —C=NR$^7$, —OR$^7$, —OC(O)R$^7$, —S(O)$_t$—R$^7$, —NR$^7$R$^8$, —NR$^7$C(O)R$^8$, —N=CR$^7$R$^8$, wherein t is 0, 1, 2 or 3.

In certain instances, $R^2$ is a substituted cycloaryl; $R^3$ is methyl and each of $R^4$, $R^5$, $R^6$, $R^7$ and $R^8$ are hydrogen.

In some embodiments, the compound of Formula II is a compound of Formula IIb:

Formula IIb

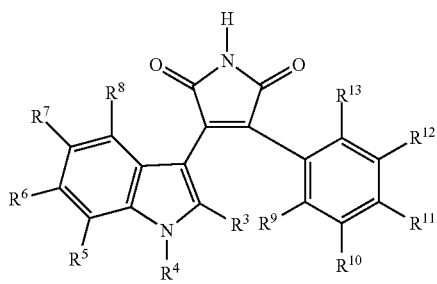

or a pharmaceutically acceptable salt, solvate or prodrug thereof, wherein:

each of $R^3$, $R^4$, $R^5$, $R^6$, $R^7$, $R^8$, $R^9$, $R^{10}$, $R^{11}$, $R^{12}$ and $R^{13}$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, —COR$^7$, —C(O)OR$^7$, —C(O)NR$^7$R$^8$, —C=NR$^7$, —OR$^7$, —OC(O)R$^7$, —S(O)$_t$—R$^7$, —NR$^7$R$^8$, —NR$^7$C(O)R$^8$, —N=CR$^7$R$^8$, wherein t is 0, 1, 2 or 3.

In some embodiments, $R^3$ is hydrogen. In other embodiments, $R^3$ is alkyl or substituted alkyl. In other embodiments, $R^3$ is aryl or substituted aryl. In other embodiments, $R^3$ is heterocycloalkyl or substituted heterocycloalkyl. In other embodiments, $R^3$ is heteroaryl or substituted heteroaryl. In other embodiments, $R^3$ is hydroxyl, alkoxyl or substituted alkoxyl. In other embodiments, $R^3$ is acyloxy or substituted acyloxy. In other embodiments, $R^3$ is alkoxylcarbonyl or substituted alkoxycarbonyl. In other embodiments, $R^3$ is acyl or substituted acyl. In other embodiments, $R^3$ is thiol. In other embodiment, $R^3$ is amino or substituted amino. In other embodiments, $R^3$ is aminoacyl or substituted aminoacyl. In other embodiments, $R^3$ is azido. In other embodiments, $R^3$ is carboxyl, substituted carboxyl, carboxyalkyl or substituted carboxyalkyl. In other embodiments, $R^3$ is cyano. In other embodiments, $R^3$ is a halogen, such as —F, —Cl, —Br and —I. In other embodiments, $R^3$ is chloro.

In some embodiments, $R^4$ is hydrogen. In other embodiments, $R^4$ is alkyl or substituted alkyl. In other embodiments, $R^4$ is aryl or substituted aryl. In other embodiments, $R^4$ is heterocycloalkyl or substituted heterocycloalkyl. In other embodiments, $R^4$ is heteroaryl or substituted heteroaryl. In other embodiments, $R^4$ is hydroxyl, alkoxyl or substituted alkoxyl. In other embodiments, $R^4$ is acyloxy or substituted acyloxy. In other embodiments, $R^4$ is alkoxylcarbonyl or substituted alkoxycarbonyl. In other embodiments, $R^4$ is acyl or substituted acyl. In other embodiments, $R^4$ is thiol. In other embodiment, $R^4$ is amino or substituted amino. In other embodiments, $R^4$ is aminoacyl or substituted aminoacyl. In other embodiments, $R^4$ is azido. In other embodiments, $R^4$ is carboxyl, substituted carboxyl, carboxyalkyl or substituted carboxyalkyl. In other embodiments, $R^4$ is cyano. In other embodiments, $R^4$ is a halogen, such as —F, —Cl, —Br and —I. In other embodiments, $R^4$ is nitro. In certain embodiments, $R^4$ is methyl.

In some embodiments, $R^5$ is hydrogen. In other embodiments, $R^5$ is alkyl or substituted alkyl. In other embodiments, $R^5$ is aryl or substituted aryl. In other embodiments, $R^5$ is heterocycloalkyl or substituted heterocycloalkyl. In other embodiments, $R^5$ is heteroaryl or substituted heteroaryl. In other embodiments, $R^5$ is hydroxyl, alkoxyl or substituted alkoxyl. In other embodiments, $R^5$ is acyloxy or substituted acyloxy. In other embodiments, $R^5$ is alkoxylcarbonyl or substituted alkoxycarbonyl. In other embodiments, $R^5$ is acyl or substituted acyl. In other embodiments, $R^5$ is thiol. In other embodiment, $R^5$ is amino or substituted amino. In other embodiments, $R^5$ is aminoacyl or substituted aminoacyl. In other embodiments, $R^5$ is azido. In other embodiments, $R^5$ is carboxyl, substituted carboxyl, carboxyalkyl or substituted carboxyalkyl. In other embodiments, $R^5$ is cyano. In other embodiments, $R^5$ is a halogen, such as —F, —Cl, —Br and —I. In other embodiments, $R^5$ is nitro.

In some embodiments, $R^6$ is hydrogen. In other embodiments, $R^6$ is alkyl or substituted alkyl. In other embodiments, $R^6$ is aryl or substituted aryl. In other embodiments, $R^6$ is heterocycloalkyl or substituted heterocycloalkyl. In other embodiments, $R^6$ is heteroaryl or substituted heteroaryl. In other embodiments, $R^6$ is hydroxyl, alkoxyl or substituted alkoxyl. In other embodiments, $R^6$ is acyloxy or substituted acyloxy. In other embodiments, $R^6$ is alkoxylcarbonyl or substituted alkoxycarbonyl. In other embodiments, $R^6$ is acyl or substituted acyl. In other embodiments, $R^6$ is thiol. In other embodiment, $R^6$ is amino or substituted amino. In other embodiments, $R^6$ is aminoacyl or substituted aminoacyl. In other embodiments, $R^6$ is azido. In other embodiments, $R^6$ is carboxyl, substituted carboxyl, carboxyalkyl or substituted carboxyalkyl. In other embodiments, $R^6$ is cyano. In other embodiments, $R^6$ is a halogen, such as —F, —Cl, —Br and —I. In other embodiments, $R^6$ is nitro. In certain embodiments, $R^6$ is alkoxylcarbonyl, such as ethoxycarbonyl.

In some embodiments, $R^7$ is hydrogen. In other embodiments, $R^7$ is alkyl or substituted alkyl. In other embodiments, $R^7$ is aryl or substituted aryl. In other embodiments, $R^7$ is heterocycloalkyl or substituted heterocycloalkyl. In other embodiments, $R^7$ is heteroaryl or substituted heteroaryl. In other embodiments, $R^7$ is hydroxyl, alkoxyl or substituted alkoxyl. In other embodiments, $R^7$ is acyloxy or substituted acyloxy. In other embodiments, $R^7$ is alkoxylcarbonyl or substituted alkoxycarbonyl. In other embodiments, $R^7$ is acyl or substituted acyl. In other embodiments, $R^7$ is thiol. In other embodiment, $R^7$ is amino or substituted amino. In other embodiments, $R^7$ is aminoacyl or substituted aminoacyl. In other embodiments, $R^7$ is azido. In other embodiments, $R^7$ is carboxyl, substituted carboxyl, carboxyalkyl or substituted carboxyalkyl. In other embodiments, $R^7$ is cyano. In other embodiments, $R^7$ is a halogen, such as —F, —Cl, —Br and —I. In other embodiments, $R^7$ is nitro. In certain embodiments, $R^7$ is amino.

In some embodiments, $R^8$ is hydrogen. In other embodiments, $R^8$ is alkyl or substituted alkyl. In other embodiments, $R^8$ is aryl or substituted aryl. In other embodiments, $R^8$ is heterocycloalkyl or substituted heterocycloalkyl. In other embodiments, $R^8$ is heteroaryl or substituted heteroaryl. In other embodiments, $R^8$ is hydroxyl, alkoxyl or substituted alkoxyl. In other embodiments, $R^8$ is acyloxy or substituted acyloxy. In other embodiments, $R^8$ is alkoxylcarbonyl or substituted alkoxycarbonyl. In other embodiments, $R^8$ is acyl or substituted acyl. In other embodiments, $R^8$ is thiol. In other embodiment, $R^8$ is amino or substituted amino. In other embodiments, $R^8$ is aminoacyl or substituted aminoacyl. In other embodiments, $R^8$ is azido. In other embodiments, $R^8$ is carboxyl, substituted carboxyl, carboxyalkyl or substituted carboxyalkyl. In other embodiments, $R^8$ is cyano. In other embodiments, $R^8$ is a halogen, such as —F, —Cl, —Br and —I. In other embodiments, $R^8$ is nitro. In certain embodiments, $R^8$ is amino.

In some embodiments, $R^9$ is hydrogen. In other embodiments, $R^9$ is alkyl or substituted alkyl. In other embodiments, $R^9$ is aryl or substituted aryl. In other embodiments, $R^9$ is heterocycloalkyl or substituted heterocycloalkyl. In other embodiments, $R^9$ is heteroaryl or substituted heteroaryl. In other embodiments, $R^9$ is hydroxyl, alkoxyl or substituted alkoxyl. In other embodiments, $R^9$ is acyloxy or substituted acyloxy. In other embodiments, $R^9$ is alkoxylcarbonyl or substituted alkoxycarbonyl. In other embodiments, $R^9$ is acyl or substituted acyl. In other embodiments, $R^9$ is thiol. In other embodiment, $R^9$ is amino or substituted amino. In other embodiments, $R^9$ is aminoacyl or substituted aminoacyl. In other embodiments, $R^9$ is azido. In other embodiments, $R^9$ is carboxyl, substituted carboxyl, carboxyalkyl or substituted carboxyalkyl. In other embodiments, $R^9$ is cyano. In other embodiments, $R^9$ is a halogen, such as —F, —Cl, —Br and —I. In other embodiments, $R^9$ is nitro. In certain embodiments, $R^9$ is amino.

In some embodiments, $R^{10}$ is hydrogen. In other embodiments, $R^{10}$ is alkyl or substituted alkyl. In other embodiments, $R^{10}$ is aryl or substituted aryl. In other embodiments, $R^{10}$ is heterocycloalkyl or substituted heterocycloalkyl. In other embodiments, $R^{10}$ is heteroaryl or substituted heteroaryl. In other embodiments, $R^{10}$ is hydroxyl, alkoxyl or substituted alkoxyl. In other embodiments, $R^{10}$ is acyloxy or substituted acyloxy. In other embodiments, $R^{10}$ is alkoxylcarbonyl or substituted alkoxycarbonyl. In other embodiments, $R^{10}$ is acyl or substituted acyl. In other embodiments, $R^{10}$ is thiol. In other embodiment, $R^{10}$ is amino or substituted amino.

In other embodiments, $R^{10}$ is aminoacyl or substituted aminoacyl. In other embodiments, $R^{10}$ is azido. In other embodiments, $R^{10}$ is carboxyl, substituted carboxyl, carboxyalkyl or substituted carboxyalkyl. In other embodiments, $R^{10}$ is cyano. In other embodiments, $R^{10}$ is a halogen, such as —F, —Cl, —Br and —I. In other embodiments, $R^{10}$ is nitro. In certain embodiments, $R^{10}$ is amino.

In some embodiments, $R^{11}$ is hydrogen. In other embodiments, $R^{11}$ is alkyl or substituted alkyl. In other embodiments, $R^{11}$ is aryl or substituted aryl. In other embodiments, $R^{11}$ is heterocycloalkyl or substituted heterocycloalkyl. In other embodiments, $R^{11}$ is heteroaryl or substituted heteroaryl. In other embodiments, $R^{11}$ is hydroxyl, alkoxyl or substituted alkoxyl. In other embodiments, $R^{11}$ is acyloxy or substituted acyloxy. In other embodiments, $R^{11}$ is alkoxylcarbonyl or substituted alkoxycarbonyl. In other embodiments, $R^{11}$ is acyl or substituted acyl. In other embodiments, $R^{11}$ is thiol. In other embodiment, $R^{11}$ is amino or substituted amino. In other embodiments, $R^{11}$ is aminoacyl or substituted aminoacyl. In other embodiments, $R^{11}$ is azido. In other embodiments, $R^{11}$ is carboxyl, substituted carboxyl, carboxyalkyl or substituted carboxyalkyl. In other embodiments, $R^{11}$ is cyano. In other embodiments, $R^{11}$ is a halogen, such as —F, —Cl, —Br and —I. In other embodiments, $R^{11}$ is nitro. In certain embodiments, $R^{11}$ is amino.

In some embodiments, $R^{12}$ is hydrogen. In other embodiments, $R^{12}$ is alkyl or substituted alkyl. In other embodiments, $R^{12}$ is aryl or substituted aryl. In other embodiments, $R^{12}$ is heterocycloalkyl or substituted heterocycloalkyl. In other embodiments, $R^{12}$ is heteroaryl or substituted heteroaryl. In other embodiments, $R^{12}$ is hydroxyl, alkoxyl or substituted alkoxyl. In other embodiments, $R^{12}$ is acyloxy or substituted acyloxy. In other embodiments, $R^{12}$ is alkoxylcarbonyl or substituted alkoxycarbonyl. In other embodiments, $R^{7}$ is acyl or substituted acyl. In other embodiments, $R^{12}$ is thiol. In other embodiment, $R^{12}$ is amino or substituted amino. In other embodiments, $R^{7}$ is aminoacyl or substituted aminoacyl. In other embodiments, $R^{12}$ is azido. In other embodiments, $R^{12}$ is carboxyl, substituted carboxyl, carboxyalkyl or substituted carboxyalkyl. In other embodiments, $R^{12}$ is cyano. In other embodiments, $R^{12}$ is a halogen, such as —F, —Cl, —Br and —I. In other embodiments, $R^{12}$ is nitro. In certain embodiments, $R^{12}$ is amino.

In some embodiments, $R^{13}$ is hydrogen. In other embodiments, $R^{13}$ is alkyl or substituted alkyl. In other embodiments, $R^{13}$ is aryl or substituted aryl. In other embodiments, $R^{13}$ is heterocycloalkyl or substituted heterocycloalkyl. In other embodiments, $R^{13}$ is heteroaryl or substituted heteroaryl. In other embodiments, $R^{13}$ is hydroxyl, alkoxyl or substituted alkoxyl. In other embodiments, $R^{13}$ is acyloxy or substituted acyloxy. In other embodiments, $R^{13}$ is alkoxylcarbonyl or substituted alkoxycarbonyl. In other embodiments, $R^{13}$ is acyl or substituted acyl. In other embodiments, $R^{13}$ is thiol. In other embodiment, $R^{13}$ is amino or substituted amino. In other embodiments, $R^{13}$ is aminoacyl or substituted aminoacyl. In other embodiments, $R^{13}$ is azido. In other embodiments, $R^{13}$ is carboxyl, substituted carboxyl, carboxyalkyl or substituted carboxyalkyl. In other embodiments, $R^{13}$ is cyano. In other embodiments, $R^{13}$ is a halogen, such as —F, —Cl, —Br and —I. In other embodiments, $R^{13}$ is nitro. In certain embodiments, $R^{13}$ is amino.

In certain embodiments, a compound of interest and salts or solvates or stereoisomers thereof, include:

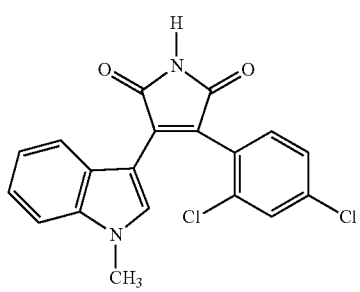 [SMILES: Cn1cc(C2=C(c3ccc(Cl)cc3Cl)C(=O)NC2=O)c2ccccc21]

("SB-216763") (3-(2,4-Dichlorophenyl)-4-(1-methyl-1H-indol-3-yl)-1H-pyrrole-2,5-dione).

Additional glycogen synthase kinase 3α and/or 3β inhibitors include:

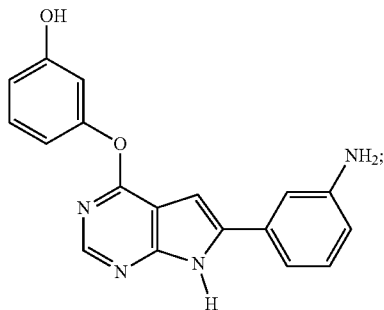

TWS119

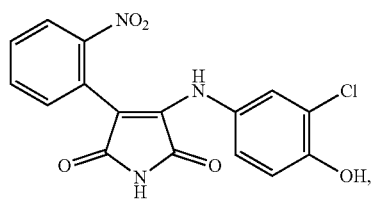

SB415286

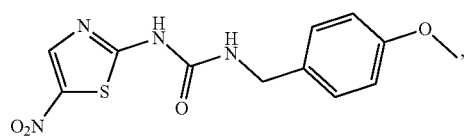

AR-A014418

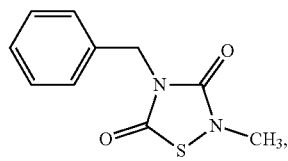

TDZD-8

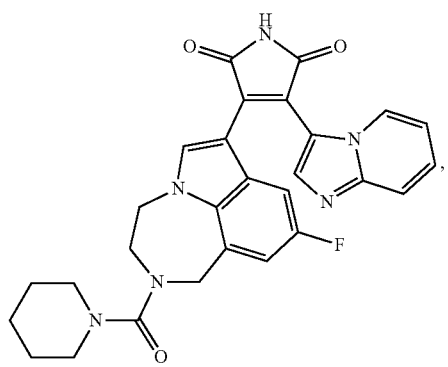

LY2090314 and pharmaceutically acceptable salts or derivatives thereof.

Additional compounds for reactivating latent immunodeficiency virus according to embodiments of the present disclosure are found in, e.g., WO2012/116170; WO2012/069525; WO2012/055880; WO2012/055879; WO2011/143651; WO2011/054848; WO2011/054846; WO2011/54845; WO2011/054843; WO2011/054553; and PCT/US2016/64614 (filed Dec. 2, 2016), the disclosures of each of which are incorporated herein by reference in their entireties and for all purposes.

Formulations, Dosages, and Routes of Administration

In general, an active agent (e.g., a GSK-3α and/or GSK-3β inhibitor, e.g., a compound of Formula I, e.g., Tideglusib or a pharmaceutically acceptable salt or derivative thereof, or a compound of Formula II, e.g., SB-216763 or a pharmaceutically acceptable salt or derivative thereof) is prepared in a pharmaceutically acceptable composition(s) for delivery to a host.

Pharmaceutically acceptable carriers preferred for use with active agents (and optionally one or more additional therapeutic agent) may include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, and microparticles, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. A composition comprising an active agent (and optionally one or more additional therapeutic agent) may also be lyophilized using means well known in the art, for subsequent reconstitution and use according to the invention.

Formulations

An active agent is administered to an individual in need thereof in a formulation with a pharmaceutically acceptable excipient(s). A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc. For the purposes of the following description of formulations, "active agent" includes an active agent as described above, and optionally one or more additional therapeutic agent.

In a subject method, an active agent may be administered to the host using any convenient means capable of resulting in the desired degree of reduction of immunodeficiency virus transcription. Thus, an active agent can be incorporated into a variety of formulations for therapeutic administration. For example, an active agent can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. In an exemplary embodiment, an active agent is formulated as a gel, as a solution, or in some other form suitable for intravaginal administration. In a further exemplary embodiment, an active agent is formulated as a gel, as a solution, or in some other form suitable for rectal (e.g., intrarectal) administration.

In pharmaceutical dosage forms, an active agent may be administered in the form of its pharmaceutically acceptable salts, or it may also be used alone or in appropriate association, as well as in combination, with other pharmaceutically active compounds. The following methods and excipients are merely exemplary and are in no way limiting.

In some embodiments, an active agent is formulated in an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

For oral preparations, an active agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An active agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

An active agent can be utilized in aerosol formulation to be administered via inhalation. An active agent can be formulated into pressurized acceptable propellants such as dichlorodifluoromethane, propane, nitrogen and the like.

Furthermore, an active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more active agents. Similarly, unit dosage forms for injection or intravenous administration may comprise the active agent(s) in a composition as a solution in sterile water, normal saline or another pharmaceutically acceptable carrier.

Unit dosage forms for intravaginal or intrarectal administration such as syrups, elixirs, gels, and suspensions may be provided wherein each dosage unit, for example, teaspoonful, tablespoonful, tablet, unit gel volume, or suppository, contains a predetermined amount of the composition containing one or more active agents.

The term "unit dosage form," as used herein, refers to physically discrete units suitable as unitary dosages for human and animal subjects, each unit containing a predetermined quantity of an active agent, calculated in an amount sufficient to produce the desired effect in association with a pharmaceutically acceptable diluent, carrier or vehicle. The specifications for a given active agent will depend in part on the particular compound employed and the effect to be achieved, and the pharmacodynamics associated with each compound in the host.

Other modes of administration will also find use with the subject invention. For instance, an active agent can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), e.g. about 1% to about 2%.

An active agent can be administered as an injectable. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

An active agent will in some embodiments be formulated for vaginal delivery. A subject formulation for intravaginal administration comprises an active agent formulated as an intravaginal bioadhesive tablet, intravaginal bioadhesive microparticle, intravaginal cream, intravaginal lotion, intravaginal foam, intravaginal ointment, intravaginal paste, intravaginal solution, or intravaginal gel.

An active agent will in some embodiments be formulated for rectal delivery. A subject formulation for intrarectal administration comprises an active agent formulated as an intrarectal bioadhesive tablet, intrarectal bioadhesive microparticle, intrarectal cream, intrarectal lotion, intrarectal foam, intrarectal ointment, intrarectal paste, intrarectal solution, or intrarectal gel.

A subject formulation comprising an active agent includes one or more of an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, poly(ethylene glycol), sucrose or starch), a disintegrator (e.g., starch, carboxymethylcellulose, hydroxypropyl starch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol).

Tablets comprising an active agent may be coated with a suitable film-forming agent, e.g., hydroxypropylmethyl cellulose, hydroxypropyl cellulose or ethyl cellulose, to which a suitable excipient may optionally be added, e.g., a softener such as glycerol, propylene glycol, diethylphthalate, or glycerol triacetate; a filler such as sucrose, sorbitol, xylitol, glucose, or lactose; a colorant such as titanium hydroxide; and the like.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosages

Although the dosage used will vary depending on the clinical goals to be achieved, a suitable dosage range of an active agent is one which provides up to about 1 mg to about 5000 mg, e.g., from about 1 mg to about 25 mg, from about 25 mg to about 50 mg, from about 50 mg to about 100 mg, from about 100 mg to about 200 mg, from about 200 mg to about 250 mg, from about 250 mg to about 500 mg, from about 500 mg to about 1000 mg, or from about 1000 mg to about 5000 mg of an active agent, which can be administered in a single dose.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

In some embodiments, a suitable dose of a compound of Formula I, e.g., Tideglusib or a pharmaceutically acceptable salt or derivative thereof, is in the range of from about 1 mg/kg body weight to about 500 mg/kg body weight, e.g., from about 5 mg/kg body weight to about 500 mg/kg body weight, from about 10 mg/kg body weight to about 500 mg/kg body weight, from about 20 mg/kg body weight to about 500 mg/kg body weight, from about 30 mg/kg body weight to about 500 mg/kg body weight, from about 40 mg/kg body weight to about 500 mg/kg body weight, from about 50 mg/kg body weight to about 500 mg/kg body weight, from about 60 mg/kg body weight to about 500 mg/kg body weight, from about 70 mg/kg body weight to about 500 mg/kg body weight, from about 80 mg/kg body weight to about 500 mg/kg body weight, from about 90 mg/kg body weight to about 500 mg/kg body weight, from about 100 mg/kg body weight to about 500 mg/kg body weight, from about 200 mg/kg body weight to about 500 mg/kg body weight, from about 300 mg/kg body weight to about 500 mg/kg body weight, or from about 400 mg/kg body weight to about 500 mg/kg body weight.

In some embodiments, a suitable dose of a compound of Formula I, e.g., Tideglusib or a pharmaceutically acceptable salt or derivative thereof, is in the range of from about 1 mg/kg body weight to about 5 mg/kg body weight, from about 5 mg/kg body weight to about 10 mg/kg body weight, from about 10 mg/kg body weight to about 20 mg/kg body weight, from about 20 mg/kg body weight to about 30 mg/kg body weight, from about 30 mg/kg body weight to about 40 mg/kg body weight, from about 40 mg/kg body weight to about 50 mg/kg body weight, from about 50 mg/kg body weight to about 100 mg/kg body weight, or from about 100 mg/kg body weight to about 500 mg/kg body weight.

In some embodiments, a single dose of an active agent is administered. In other embodiments, multiple doses of an active agent are administered. Where multiple doses are administered over a period of time, an active agent is administered, e.g., twice daily (qid), daily (qd), every other day (qod), every third day, three times per week (tiw), or twice per week (biw) over a period of time. For example, an active agent is administered qid, qd, qod, tiw, or biw over a period of from about one day to about 2 years or more. For example, an active agent is administered at any of the aforementioned frequencies for one week, two weeks, one month, two months, six months, one year, or two years, or more, depending on various factors.

Where two different active agents are administered, a first active agent and a second active agent can be administered in separate formulations. A first active agent and a second active agent can be administered substantially simultaneously, or within about 30 minutes, about 1 hour, about 2 hours, about 4 hours, about 8 hours, about 16 hours, about 24 hours, about 36 hours, about 72 hours, about 4 days, about 7 days, or about 2 weeks of one another.

Routes of Administration

An active agent is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, transdermal, subcutaneous, intradermal, topical application, intravenous, vaginal, nasal, and other parenteral routes of administration. In some embodiments, an active agent is administered via an intravaginal route of administration. In other embodiments, an active agent is administered via an intrarectal route of administration. Routes of administration may be combined, if desired, or adjusted depending upon the agent and/or the desired effect. The composition can be administered in a single dose or in multiple doses.

An active agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, vaginal, transdermal, subcutaneous, intramuscular, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

An active agent can also be delivered to the subject by enteral administration. Enteral routes of administration include, but are not necessarily limited to, oral and rectal (e.g., using a suppository) delivery.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as the number of viral particles per unit blood. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts (wherein the term "host" is used interchangeably herein with the terms "subject" and "patient") are treatable according to the subject methods. Generally such hosts are "mammals" or "mammalian," where these terms are used broadly to describe organisms which are within the class mammalia, and primates (e.g., humans, chimpanzees, and monkeys), that are susceptible to immunodeficiency virus (e.g., HIV) infection. In many embodiments, the hosts will be humans.

Kits, Containers, Devices, Delivery Systems

Kits with unit doses of the active agent, e.g. in oral, vaginal, rectal, transdermal, or injectable doses (e.g., for intramuscular, intravenous, or subcutaneous injection), are provided. In such kits, in addition to the containers containing the unit doses will be an informational package insert describing the use and attendant benefits of the drugs in treating an immunodeficiency virus (e.g., an HIV) infection. Suitable active agents and unit doses are those described herein above.

In many embodiments, a subject kit will further include instructions for practicing the subject methods or means for obtaining the same (e.g., a website URL directing the user to a webpage which provides the instructions), where these instructions are typically printed on a substrate, which substrate may be one or more of: a package insert, the packaging, formulation containers, and the like.

In some embodiments, a subject kit includes one or more components or features that increase patient compliance, e.g., a component or system to aid the patient in remembering to take the active agent at the appropriate time or interval. Such components include, but are not limited to, a calendaring system to aid the patient in remembering to take the active agent at the appropriate time or interval.

The present invention provides a delivery system comprising a GSK-3α and/or GSK-3β inhibitor, e.g., a compound of Formula I, e.g., Tideglusib or a pharmaceutically acceptable salt or derivative thereof, or a compound of Formula II, e.g., SB-216763 or a pharmaceutically acceptable salt or derivative thereof. In some embodiments, the delivery system is a delivery system that provides for injection of a formulation comprising an active agent subcutaneously, intravenously, or intramuscularly. In other embodiments, the delivery system is a vaginal or rectal delivery system.

In some embodiments, an active agent is packaged for oral administration. The present invention provides a packaging unit comprising daily dosage units of an active agent. For example, the packaging unit is in some embodiments a conventional blister pack or any other form that includes tablets, pills, and the like. The blister pack will contain the appropriate number of unit dosage forms, in a sealed blister pack with a cardboard, paperboard, foil, or plastic backing, and enclosed in a suitable cover. Each blister container may be numbered or otherwise labeled, e.g., starting with day 1.

In some embodiments, a subject delivery system comprises an injection device. Exemplary, non-limiting drug delivery devices include injections devices, such as pen injectors, and needle/syringe devices. In some embodiments, the invention provides an injection delivery device that is pre-loaded with a formulation comprising an effective amount of a GSK-3α and/or GSK-3β inhibitor, e.g., a compound of Formula I, e.g., Tideglusib or a pharmaceutically acceptable salt or derivative thereof, or an injection delivery device that is pre-loaded with a formulation comprising an effective amount of a compound of Formula II, e.g., SB-216763 or a pharmaceutically acceptable salt or derivative thereof. For example, a subject delivery device comprises an injection device pre-loaded with a single dose of a GSK-3α and/or GSK-3β inhibitor, e.g., a compound of Formula I, e.g., Tideglusib or a pharmaceutically acceptable salt or derivative thereof, or an injection device pre-loaded with a single dose of a compound of Formula II, e.g., SB-216763 or a pharmaceutically acceptable salt or derivative thereof. A subject injection device can be re-usable or disposable.

Pen injectors are well known in the art. Exemplary devices which can be adapted for use in the present methods are any of a variety of pen injectors from Becton Dickinson, e.g., BD™ Pen, BD™ Pen II, BD™ Auto-Injector; a pen injector from Innoject, Inc.; any of the medication delivery pen devices discussed in U.S. Pat. Nos. 5,728,074, 6,096,010, 6,146,361, 6,248,095, 6,277,099, and 6,221,053; and the like. The medication delivery pen can be disposable, or reusable and refillable.

The present invention provides a delivery system for vaginal or rectal delivery of an active agent to the vagina or rectum of an individual. The delivery system comprises a device for insertion into the vagina or rectum. In some embodiments, the delivery system comprises an applicator for delivery of a formulation into the vagina or rectum; and a container that contains a formulation comprising an active agent. In these embodiments, the container (e.g., a tube) is adapted for delivering a formulation into the applicator. In other embodiments, the delivery system comprises a device that is inserted into the vagina or rectum, which device includes an active agent. For example, the device is coated with, impregnated with, or otherwise contains a formulation comprising the active agent.

In some embodiments, the vaginal or rectal delivery system is a tampon or tampon-like device that comprises a subject formulation. Drug delivery tampons are known in the art, and any such tampon can be used in conjunction with a subject drug delivery system. Drug delivery tampons are described in, e.g., U.S. Pat. No. 6,086,909. If a tampon or tampon-like device is used, there are numerous methods by which an active agent can be incorporated into the device. For example, the drug can be incorporated into a gel-like bioadhesive reservoir in the tip of the device. Alternatively, the drug can be in the form of a powdered material positioned at the tip of the tampon. The drug can also be absorbed into fibers at the tip of the tampon, for example, by dissolving the drug in a pharmaceutically acceptable carrier and absorbing the drug solution into the tampon fibers. The drug can also be dissolved in a coating material which is applied to the tip of the tampon. Alternatively, the drug can be incorporated into an insertable suppository which is placed in association with the tip of the tampon.

In other embodiments, the drug delivery device is a vaginal or rectal ring. Vaginal or rectal rings usually consist of an inert elastomer ring coated by another layer of elastomer containing an active agent to be delivered. The rings can be easily inserted, left in place for the desired period of time (e.g., up to 7 days), then removed by the user. The ring can optionally include a third, outer, rate-controlling elastomer layer which contains no drug. Optionally, the third ring can contain a second drug for a dual release ring. The drug can be incorporated into polyethylene glycol throughout the silicone elastomer ring to act as a reservoir for drug to be delivered.

In other embodiments, a subject vaginal or rectal delivery system is a vaginal or rectal sponge. The active agent is incorporated into a silicone matrix which is coated onto a cylindrical drug-free polyurethane sponge, as described in the literature.

Pessaries, tablets, and suppositories are other examples of drug delivery systems which can be used, e.g., in carrying out a method of the present disclosure. These systems have been described extensively in the literature.

Bioadhesive microparticles constitute still another drug delivery system suitable for use in the present invention. This system is a multi-phase liquid or semi-solid preparation which does not seep from the vagina or rectum as do many suppository formulations. The substances cling to the wall of the vagina or rectum and release the drug over a period of time. Many of these systems were designed for nasal use but can be used in the vagina or rectum as well (e.g. U.S. Pat. No. 4,756,907). The system may comprise microspheres with an active agent; and a surfactant for enhancing uptake of the drug. The microparticles have a diameter of 10-100 μm and can be prepared from starch, gelatin, albumin, collagen, or dextran.

Another system is a container comprising a subject formulation (e.g., a tube) that is adapted for use with an applicator. The active agent is incorporated into creams, lotions, foams, paste, ointments, and gels which can be applied to the vagina or rectum using an applicator. Processes for preparing pharmaceuticals in cream, lotion, foam, paste, ointment and gel formats can be found throughout the literature. An example of a suitable system is a standard fragrance free lotion formulation containing glycerol, ceramides, mineral oil, petrolatum, parabens, fragrance and water such as the product sold under the trademark JERGENS™ (Andrew Jergens Co., Cincinnati, Ohio). Suitable nontoxic pharmaceutically acceptable systems for use in the compositions of the present invention will be apparent to those skilled in the art of pharmaceutical formulations and examples are described in Remington's Pharmaceutical Sciences, 19th Edition, A. R. Gennaro, ed., 1995. The choice of suitable carriers will depend on the exact nature of the particular vaginal or rectal dosage form desired, e.g., whether the active ingredient(s) is/are to be formulated into a cream, lotion, foam, ointment, paste, solution, or gel, as well as on the identity of the active ingredient(s). Other suitable delivery devices are those described in U.S. Pat. No. 6,476,079.

Combination Therapy

In some embodiments, two or more GSK-3α and/or GSK-3β inhibitors, e.g., a compound of Formula I, e.g., Tideglusib or a pharmaceutically acceptable salt or derivative thereof and a compound of Formula II, e.g., SB-216763 or a pharmaceutically acceptable salt or derivative thereof are administered. In some embodiments, a GSK-3α and/or GSK-3β inhibitor, e.g., a compound of Formula I, e.g., Tideglusib or a pharmaceutically acceptable salt or derivative thereof and/or a compound of Formula II, e.g., SB-216763 or a pharmaceutically acceptable salt or derivative thereof, is administered in combination therapy with one or more additional therapeutic agents. Suitable additional therapeutic agents include agents that inhibit one or more functions of an immunodeficiency virus; agents that treat or ameliorate a symptom of an immunodeficiency virus infection; agents that treat an infection that occurs secondary to an immunodeficiency virus infection; and the like.

Therapeutic agents include, e.g., beta-lactam antibiotics, tetracyclines, chloramphenicol, neomycin, gramicidin, bacitracin, sulfonamides, nitrofurazone, nalidixic acid, cortisone, hydrocortisone, betamethasone, dexamethasone, fluocortolone, prednisolone, triamcinolone, indomethacin, sulindac, acyclovir, amantadine, rimantadine, recombinant soluble CD4 (rsCD4), anti-receptor antibodies (e.g., for rhinoviruses), nevirapine, cidofovir (Vistide™), trisodium phosphonoformate (Foscarnet™), famcyclovir, pencyclovir, valacyclovir, nucleic acid/replication inhibitors, interferon, zidovudine (AZT, Retrovir™), didanosine (dideoxyinosine, ddI, Videx™), stavudine (d4T, Zerit™), zalcitabine (dideoxycytosine, ddC, Hivid™), nevirapine (Viramune™), lamivudine (Epivir™, 3TC), protease inhibitors, saquinavir (Invirase™, Fortovase™), ritonavir (Norvir™), nelfinavir (Viracept™), efavirenz (Sustiva™), abacavir (Ziagen™), amprenavir (Agenerase™) indinavir (Crixivan™), ganciclovir, AzDU, delavirdine (Rescriptor™), kaletra, trizivir, rifampin, clathiromycin, erythropoietin, colony stimulating factors (G-CSF and GM-CSF), non-nucleoside reverse transcriptase inhibitors, nucleoside inhibitors, adriamycin, fluorouracil, methotrexate, asparaginase and combinations thereof. Anti-HIV agents are those in the preceding list that specifically target a function of one or more HIV proteins.

In some embodiments, a GSK-3α and/or GSK-3β inhibitor, e.g., a compound of Formula I, e.g., Tideglusib or a pharmaceutically acceptable salt or derivative thereof, or a compound of Formula II, e.g., SB-216763 or a pharmaceutically acceptable salt or derivative thereof, is administered in combination therapy with two or more anti-HIV agents. For example, a GSK-3α and/or GSK-3β inhibitor, e.g., a compound of Formula I, e.g., Tideglusib or a pharmaceutically acceptable salt or derivative thereof, or a compound of Formula II, e.g., SB-216763 or a pharmaceutically acceptable salt or derivative thereof, can be administered in combination therapy with one, two, or three nucleoside reverse transcriptase inhibitors (e.g., Combivir, Epivir, Hivid, Retrovir, Videx, Zerit, Ziagen, etc.). A GSK-3α and/or GSK-3β inhibitor, e.g., compound of Formula I, e.g., Tideglusib or a pharmaceutically acceptable salt or derivative thereof, or a compound of Formula II, e.g., SB-216763 or a pharmaceutically acceptable salt or derivative thereof, can be administered in combination therapy with one or two non-nucleoside reverse transcriptase inhibitors (e.g., Rescriptor, Sustiva, Viramune, etc.). A GSK-3α and/or GSK-3β inhibitor, e.g., a compound of Formula I, e.g., Tideglusib or a pharmaceutically acceptable salt or derivative thereof, or a compound of Formula II, e.g., SB-216763 or a pharmaceutically acceptable salt or derivative thereof, can be administered in combination therapy with one or two protease inhibitors (e.g., Agenerase, Crixivan, Fortovase, Invirase, Kaletra, Norvir, Viracept, etc.). A GSK-3α and/or GSK-3β inhibitor, e.g., a compound of Formula I, e.g., Tideglusib or a pharmaceutically acceptable salt or derivative thereof, or a compound of Formula II, e.g., SB-216763 or a pharmaceutically acceptable salt or derivative thereof, can be administered in combination therapy with a protease inhibitor and a nucleoside reverse transcriptase inhibitor. A GSK-3α and/or GSK-3β inhibitor, e.g., a compound of Formula I, e.g., Tideglusib or a pharmaceutically acceptable salt or derivative thereof, or a compound of Formula II, e.g., SB-216763 or a pharmaceutically acceptable salt or derivative thereof, can be administered in combination therapy with a protease inhibitor, a nucleoside reverse transcriptase inhibitor, and a non-nucleoside reverse transcriptase inhibitor. A GSK-3α and/or GSK-3β inhibitor, e.g., a compound of Formula I, e.g., Tideglusib or a pharmaceutically acceptable salt or derivative thereof, or a compound of Formula II, e.g., SB-216763 or a pharmaceutically acceptable salt or derivative thereof, can be administered in combination therapy with a protease inhibitor and a non-nucleoside reverse transcriptase inhibitor. Other combinations of a GSK-3α and/or GSK-3β inhibitor, e.g., a compound of Formula I, e.g., Tideglusib or a pharmaceutically acceptable salt or derivative thereof, or a compound of Formula II, e.g., SB-216763 or a pharmaceutically acceptable salt or derivative thereof, with one or more of a protease inhibitor, a nucleoside reverse transcriptase inhibitor, and a non-nucleoside reverse transcriptase inhibitor are contemplated.

In some embodiments, a subject treatment method involves administering: a) a GSK-3α and/or GSK-3β inhibitor, e.g., a compound of Formula I, e.g., Tideglusib or a pharmaceutically acceptable salt or derivative thereof, or a compound of Formula II, e.g., SB-216763 or a pharmaceutically acceptable salt or derivative thereof; and b) an agent that inhibits an immunodeficiency virus function selected from viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity.

In some embodiments, a subject treatment method involves administering: a) a GSK-3α and/or GSK-3β inhibitor, e.g., a compound of Formula I, e.g., Tideglusib or a pharmaceutically acceptable salt or derivative thereof, or a compound of Formula II, e.g., SB-216763 or a pharmaceutically acceptable salt or derivative thereof; and b) an HIV inhibitor, where suitable HIV inhibitors include, but are not limited to, one or more nucleoside/nucleotide reverse transcriptase inhibitors (NRTIs), non-nucleoside reverse transcriptase inhibitors (NNRTIs), protease inhibitors (PIs), fusion inhibitors, integrase inhibitors, chemokine receptor (e.g., CXCR4, CCR5) inhibitors, and hydroxyurea.

Nucleoside reverse transcriptase inhibitors include, but are not limited to, abacavir (ABC; ZIAGEN™), didanosine (dideoxyinosine (ddI); VIDEX™), lamivudine (3TC; EPIVIR™), stavudine (d4T; ZERIT™, ZERIT XR™), zalcitabine (dideoxycytidine (ddC); HIVID™), zidovudine (ZDV, formerly known as azidothymidine (AZT); RETROVIR™), abacavir, zidovudine, and lamivudine (TRIZIVIR™), zidovudine and lamivudine (COMBIVIR™), and emtricitabine (EMTRIVA™). Nucleotide reverse transcriptase inhibitors include tenofovir disoproxil fumarate (VIREAD™). Non-nucleoside reverse transcriptase inhibitors for HIV include, but are not limited to, nevirapine (VIRAMUNE™), delavirdine mesylate (RESCRIPTOR™), and efavirenz (SUSTIVA™).

Protease inhibitors (PIs) for treating HIV infection include amprenavir (AGENERASE™), saquinavir mesylate (FORTOVASE™, INVIRASE™.), ritonavir (NORVIR™), indinavir sulfate (CRIXIVAN™), nelfmavir mesylate (VIRACEPT™), lopinavir and ritonavir (KALETRA™), atazanavir (REYATAZ™), and fosamprenavir (LEXIVA™).

Fusion inhibitors prevent fusion between the virus and the cell from occurring, and therefore, prevent HIV infection and multiplication. Fusion inhibitors include, but are not limited to, enfuvirtide (FUZEON™), Lalezari et al., New England J. Med., 348:2175-2185 (2003); and maraviroc (SELZENTRY™, Pfizer).

An integrase inhibitor blocks the action of integrase, preventing HIV-1 genetic material from integrating into the host DNA, and thereby stopping viral replication. Integrase inhibitors include, but are not limited to, raltegravir (ISENTRESS™, Merck); and elvitegravir (GS 9137, Gilead Sciences).

Maturation inhibitors include, e.g., bevirimat (3α-(3-carboxy-3-methyl-butanoyloxy) lup-20(29)-en-28-oic acid); and Vivecon (MPC9055).

In some embodiments, a subject treatment method involves administering: a) a GSK-3α and/or GSK-3β inhibitor, e.g., a compound of Formula I, e.g., Tideglusib or a pharmaceutically acceptable salt or derivative thereof, or a compound of Formula II, e.g., SB-216763 or a pharmaceutically acceptable salt or derivative thereof; and b) one or more of: (1) an HIV protease inhibitor selected from amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-2/2, DPU-681, DPC-684, GW640385X, DG17, PPL-100, DG35, and AG 1859; (2) an HIV non-nucleoside inhibitor of reverse transcriptase selected from capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirene), efavirenz, BILR 355 BS, VRX 840773, UK-453061, and RDEA806; (3) an HIV nucleoside inhibitor of reverse transcriptase selected from zidovudine, emtricitabine, didanosine, stavudine, zalcitabine, lamivudine, abacavir, amdoxovir, elvucitabine, alovudine, MIV-210, racivir, D-d4FC, emtricitabine, phosphazide, fozivudine tidoxil, apricitibine (AVX754), amdoxovir, KP-1461, and fosalvudine tidoxil (formerly HDP 99.0003); (4) an HIV nucleotide inhibitor of reverse transcriptase selected from tenofovir and adefovir; (5) an HIV integrase inhibitor selected from curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-53 8158, GSK364735C, BMS-707035, MK-2048, and BA 011; (6) a gp41 inhibitor selected from enfuvirtide, sifuvirtide, FB006M, and TRI-1144; (7) a CXCR4 inhibitor, such as AMD-070; (8) an entry inhibitor, such as SP01A; (9) a gp120 inhibitor, such as BMS-488043 and/or BlockAide/CR; (10) a G6PD and NADH-oxidase inhibitor, such as immunitin; (11) a CCR5 inhibitors selected from the group consisting of aplaviroc, vicriviroc, maraviroc, PRO-140, INCB15050, PF-232798 (Pfizer), and CCR5 mAb004; (12) another drug for treating HIV selected from BAS-100, SPI-452, REP 9, SP-01A, TNX-355, DES6, ODN-93, ODN-112, VGV-1, PA-457 (bevirimat), Ampligen, HRG214, Cytolin, VGX-410, KD-247, AMZ 0026, CYT 99007A-221 HIV, DEBIO-025, BAY 50-4798, MDXO10 (ipilimumab), PBS 119, ALG 889, and PA-1050040 (PA-040); (13) any combinations or mixtures of the above.

As further examples, in some embodiments, a subject treatment method involves administering: a) a GSK-3α and/or GSK-3β inhibitor, e.g., a compound of Formula I, e.g., Tideglusib or a pharmaceutically acceptable salt or derivative thereof, or a compound of Formula II, e.g., SB-216763 or a pharmaceutically acceptable salt or derivative thereof; and b) one or more of: i) amprenavir (Agenerase; (3S)-oxolan-3-yl N-[(2S,3R)-3-hydroxy-4-[N-(2-methylpropyl)(4-aminobenzene)sulfonamido]-1-phenylbutan-2-yl]carbamate) in an amount of 600 mg or 1200 mg twice daily; ii) tipranavir (Aptivus; N-{3-[(1R)-1-[(2R)-6-hydroxy-4-oxo-2-(2-phenylethyl)-2-propyl-3,4-dihydro-2H-pyran-5-yl]propyl]phenyl}-5-(trifluoromethyl) pyridine-2-sulfonamide) in an amount of 500 mg twice daily; iii) idinavir (Crixivan; (2S)-1-[(2S,4R)-4-benzyl-2-hydroxy-4-{[(1S,2R)-2-hydroxy-2,3-dihydro-1H-inden-1-yl]carbamoyl}butyl]-N-tert-butyl-4-(pyridin-3-ylmethyl) piperazine-2-carboxamide) in an amount of 800 mg three times daily; iv) saquinavir (Invirase; 2S)—N-[(2S,3R)-4-[(3S)-3-(tert-butylcarbamoyl)-decahydroisoquinolin-2-yl]-3-hydroxy-1-phenylbutan-2-yl]-2-(quinolin-2-ylformamido)butanediamide) in an amount of 1,000 mg twice daily; v) lopinavir and ritonavir (Kaleta; where lopinavir is 2S)—N-[(2S,4S,5S)-5-[2-(2,6-dimethylphenoxy)acetamido]-4-hydroxy-1,6-diphenylhexan-2-yl]-3-methyl-2-(2-oxo-1,3-diazinan-1-yl)butanamide; and ritonavir is 1,3-thiazol-5-ylmethyl N-[(2S,3S,5S)-3-hydroxy-5-[(2S)-3-methyl-2-{[methyl({[2-(propan-2-yl)-1,3-thiazol-4-yl]methyl}) carbamoyl]amino}butanamido]-1,6-diphenylhexan-2-yl] carbamate) in an amount of 133 mg twice daily; vi) fosamprenavir (Lexiva; {[(2R,3S)-1-[N-(2-methylpropyl) (4-aminobenzene)sulfonamido]-3-({[(3S)-oxolan-3-yloxy] carbonyl}amino)-4-phenylbutan-2-yl]oxy}phosphonic acid) in an amount of 700 mg or 1400 mg twice daily); vii) ritonavir (Norvir) in an amount of 600 mg twice daily; viii) nelfinavir (Viracept; (3S,4aS,8aS)—N-tert-butyl-2-[(2R,3R)-2-hydroxy-3-[(3-hydroxy-2-methylphenyl)formamido]-4-(phenylsulfanyl)butyl]-decahydroisoquinoline-3-carboxamide) in an amount of 750 mg three times daily or in an amount of 1250 mg twice daily; ix) Fuzeon (Acetyl-YTSLIHSLIEESQNQ QEKNEQELLELDKWASLWNWF-amide; SEQ ID NO: 1) in an amount of 90 mg twice daily; x) Combivir in an amount of 150 mg lamivudine (3TC; 2',3'-dideoxy-3'-thiacytidine) and 300 mg zidovudine (AZT; azidothymidine) twice daily; xi) emtricitabine (Emtriva; 4-amino-5-fluoro-1-[(2R,5S)-2-(hydroxymethyl)-1,3-oxathiolan-5-yl]-1,2-dihydropyrimidin-2-one) in an amount of 200 mg once daily; xii) Epzicom in an amount of 600 mg abacavir (ABV; {(1S,4R)-4-[2-amino-6-(cyclopropylamino)-9H-purin-9-yl]cyclopent-2-en-1-yl}methanol) and 300 mg 3TC once daily; xiii) zidovudine (Retrovir; AZT or azidothymidine) in an amount of 200 mg three times daily; xiv) Trizivir in an amount of 150 mg 3TC and 300 mg ABV and 300 mg AZT twice daily; xv) Truvada in an amount of 200 mg emtricitabine and 300 mg tenofovir (({[((2R)-1-(6-amino-9H-purin-9-yl)propan-2-yl]oxy}methyl)phosphonic acid) once daily; xvi) didanosine (Videx; 2',3'-dideoxyinosine) in an amount of 400 mg once daily; xvii) tenofovir (Viread) in an amount of 300 mg once daily; xviii) abacavir (Ziagen) in an amount of 300 mg twice daily; xix) atazanavir (Reyataz; methyl N-[(1S)-1-{[(2S,3S)-3-hydroxy-4-[(2S)-2-[(methoxycarbonyl)amino]-3,3-dimethyl-N'-{[4-(pyridin-2-yl)phenyl]methyl}butanehydrazido]-1-phenylbutan-2-yl] carbamoyl}-2,2-dimethylpropyl]carbamate) in an amount of 300 mg once daily or 400 mg once daily; xx) lamivudine (Epivir) in an amount of 150 mg twice daily; xxi) stavudine (Zerit; 2'-3'-didehydro-2'-3'-dideoxythymidine) in an amount of 40 mg twice daily; xxii) delavirdine (Rescriptor; N-[2-({4-[3-(propan-2-ylamino)pyridin-2-yl]piperazin-1-yl}carbonyl)-1H-indol-5-yl]methanesulfonamide) in an amount of 400 mg three times daily; xxiii) efavirenz (Sustiva; (4S)-6-chloro-4-(2-cyclopropylethynyl)-4-(trifluoromethyl)-2,4-dihydro-1H-3,1-benzoxazin-2-one) in an amount of 600 mg once daily); xxiv) nevirapine (Viramune; 11-cyclopropyl-4-methyl-5,11-dihydro-6H-dipyrido[3,2-b:2',3'-e] [1,4]diazepin-6-one) in an amount of 200 mg twice daily); xxv) bevirimat; and xxvi) Vivecon.

In some embodiments, a subject treatment method involves administering: a) a GSK-3α and/or GSK-3β inhibitor, e.g., a compound of Formula I, e.g., Tideglusib or a pharmaceutically acceptable salt or derivative thereof, or a compound of Formula II, e.g., SB-216763 or a pharmaceutically acceptable salt or derivative thereof; and b) a PKC activator. An example of a suitable PKC activator is prostratin ((1aR,1bS,4aR,7aS,7bR,8R,9aS)-4a,7b-dihydroxy-3-(hydroxymethyl)-1,1,6,8-tetramethyl-5-oxo-1,1a, 1b,4,4a,5, 7a,7b,8,9-decahydro-9aH-cyclopropa[3,4]benzo[1,2-e] azulen-9a-yl). The PKC activator can be administered in a separate formulation from a GSK-3α and/or GSK-3β inhibitor, e.g., a compound of Formula I, e.g., Tideglusib or a pharmaceutically acceptable salt or derivative thereof, or a compound of Formula II, e.g., SB-216763 or a pharmaceutically acceptable salt or derivative thereof. A PKC activator can be co-formulated with a GSK-3α and/or GSK-3β inhibitor, e.g., a compound of Formula I, e.g., Tideglusib or a pharmaceutically acceptable salt or derivative thereof, or a compound of Formula II, e.g., SB-216763 or a pharmaceutically acceptable salt or derivative thereof, and the co-formulation administered to an individual. The present disclosure provides a kit comprising a PKC activator in a first container; and a GSK-3α and/or GSK-3β inhibitor, e.g., a compound of Formula I, e.g., Tideglusib or a pharmaceutically acceptable salt or derivative thereof, or a compound of Formula II, e.g., SB-216763 or a pharmaceutically acceptable salt or derivative thereof, in a second container.

In some embodiments, a GSK-3α and/or GSK-3β inhibitor, e.g., a compound of Formula I, e.g., Tideglusib or a pharmaceutically acceptable salt or derivative thereof, or a compound of Formula II, e.g., SB-216763 or a pharmaceutically acceptable salt or derivative thereof, is administered in combination therapy with one or more additional LRAs as described herein. Such a combination may be administered, for example, in further combination with e.g., agents that inhibit one or more functions of an immunodeficiency virus; agents that treat or ameliorate a symptom of an immunodeficiency virus infection; and agents that treat an infection that occurs secondary to an immunodeficiency virus infection as described herein. Additional LRAs are described in, e.g., WO2012/116170; WO2012/069525; WO2012/055880; WO2012/055879; WO2011/143651; WO2011/054848; WO2011/054846; WO2011/54845; WO2011/054843; WO2011/054553; and PCT/US2016/64614 (filed Dec. 2, 2016), the disclosures of each of which are incorporated herein by reference in their entireties and for all purposes. Additional LRAs which may be used in combination with a GSK-3α and/or GSK-3β inhibitor, e.g., a compound of Formula I, e.g., Tideglusib or a pharmaceutically acceptable salt or derivative thereof, or a compound of Formula II, e.g., SB-216763 or a pharmaceutically acceptable salt or derivative thereof, include, e.g., protein kinase C (PKC) activators (e.g., ingenol-3, prostratin, and bryostatin-1), protein kinase B (AKT) activators (e.g., SC-79 (2-amino-6-chloro-α-cyano-3-(ethoxycarbonyl)-4H-1-benzopyran-4-acetic acid ethyl ester)), HDAC inhibitors (e.g., suberanilohydroxamic acid (vorinostat or SAHA), romidepsin, and panobinostat), bromodomain and extra-terminal domain (BET) family inhibitors (e.g., JQ1, IBET), GSK-3β inhibitors (e.g., SB-216763 (3-(2,4-Dichlorophenyl)-4-(1-methyl-1H-indol-3-yl)-1H-pyrrole-2,5-dione)), pharmaceutically acceptable salts or derivatives thereof, and combinations thereof or combinations of pharmaceutically acceptable salts or derivatives thereof. The additional LRA can be administered in a separate formulation from a GSK-3α and/or GSK-3β inhibitor, e.g., a compound of Formula I, e.g., Tideglusib or a pharmaceutically acceptable salt or derivative thereof, or a compound of Formula II, e.g., SB-216763 or a pharmaceutically acceptable salt or derivative thereof. An additional LRA can be co-formulated with a GSK-3α and/or GSK-3β inhibitor, e.g., a compound of Formula I, e.g., Tideglusib or a pharmaceutically acceptable salt or derivative thereof, or a compound of Formula II, e.g., SB-216763 or a pharmaceutically acceptable salt or derivative thereof, and the co-formulation administered to an individual. The present disclosure provides a kit comprising an additional LRA activator in a first container; and a GSK-3α and/or GSK-3β inhibitor, e.g., a compound of Formula I, e.g., Tideglusib or a pharmaceutically acceptable salt or derivative thereof, or a compound of Formula II, e.g., SB-216763 or a pharmaceutically acceptable salt or derivative thereof, in a second container.

Subjects Suitable for Treatment

The methods of the present disclosure are suitable for treating individuals who have an immunodeficiency virus infection, e.g., who have been diagnosed as having an immunodeficiency virus infection.

The methods of the present disclosure are suitable for treating individuals who have an HIV infection (e.g., who have been diagnosed as having an HIV infection). Such individuals may include individuals with an acute or chronic HIV infection (e.g., who have been diagnosed as having an acute or chronic HIV infection). Individuals suitable for treatment include individuals infected with HIV-1 and/or HIV-2, or any variant, group, or subtype thereof.

The methods of the present disclosure are suitable for treating individuals who have previously been treated with a conventional antiretroviral treatment (ART).

Detection Methods

The present disclosure provides detection methods for identifying a cell that has latent HIV. In some embodiments, the methods involve contacting a cell obtained from an individual with a GSK-3α and/or GSK-3β inhibitor; and detecting expression of an HIV-encoded gene product. If the cell expresses an HIV-encoded gene product when contacted with the GSK-3α and/or GSK-3β inhibitor, but does not express detectable levels of the HIV-encoded gene product in the absence of the GSK-3α and/or GSK-3β inhibitor, the cell is considered to harbor latent HIV (i.e., to have latent HIV present in the cell genome). Thus, a subject detection method can comprise contacting a cell obtained from an individual with a GSK-3α and/or GSK-3β inhibitor; detecting expression of an HIV-encoded gene product; and comparing the expression, if any, of the HIV-encoded gene product in the cell contacted with the GSK-3α and/or GSK-3β inhibitor with expression of the HIV-encoded gene product in a control cell not contacted with the GSK-3α and/or GSK-3β inhibitor.

In some embodiments, the methods involve contacting a cell obtained from an individual with a compound of Formula I, e.g., Tideglusib or a pharmaceutically acceptable salt or derivative thereof; and detecting expression of an HIV-encoded gene product. If the cell expresses an HIV-encoded gene product when contacted with a compound of Formula I, e.g., Tideglusib or the pharmaceutically acceptable salt or derivative thereof, but does not express detectable levels of the HIV-encoded gene product in the absence of a compound of Formula I, e.g., Tideglusib or the pharmaceutically acceptable salt or derivative thereof, the cell is considered to harbor latent HIV (i.e., to have latent HIV present in the cell genome). Thus, a subject detection method can comprise contacting a cell obtained from an individual with a compound of Formula I, e.g., Tideglusib or a pharmaceutically acceptable salt or derivative thereof; detecting expression of an HIV-encoded gene product; and comparing the expression, if any, of the HIV-encoded gene product in the cell contacted with the compound of Formula I, e.g., Tideglusib or the pharmaceutically acceptable salt or derivative thereof, with expression of the HIV-encoded gene product in a control cell not contacted with the compound of Formula I, e.g., Tideglusib or the pharmaceutically acceptable salt or derivative thereof.

In other embodiments, the methods generally involve contacting a cell obtained from an individual with a compound of Formula II, e.g., SB-216763 or a pharmaceutically acceptable salt or derivative thereof; and detecting expression of an HIV-encoded gene product. If the cell expresses an HIV-encoded gene product when contacted with a compound of Formula II, e.g., SB-216763 or a pharmaceutically acceptable salt or derivative thereof, but does not express detectable levels of the HIV-encoded gene product in the absence of a compound of Formula II, e.g., SB-216763 or a pharmaceutically acceptable salt or derivative thereof, the cell is considered to harbor latent HIV (i.e., to have latent HIV present in the cell genome). Thus, a subject detection method can comprise contacting a cell obtained from an individual with a compound of Formula II, e.g., SB-216763 or a pharmaceutically acceptable salt or derivative thereof; detecting expression of an HIV-encoded gene product; and comparing the expression, if any, of the HIV-encoded gene product in the cell contacted with the compound of Formula II, e.g., SB-216763 or a pharmaceutically acceptable salt or derivative thereof, with expression of the HIV-encoded gene product in a control cell not contacted with the compound oft Formula II, e.g., SB-216763 or a pharmaceutically acceptable salt or derivative thereof.

Cells obtained from an individual include cells in a liquid cell suspension sample, and cells in a solid tissue sample. A cell sample obtained from an individual can be from any of a variety of tissues, e.g., brain, blood, saliva, muscle, liver, bronchoalveolar lavage, sputum, etc. The cells can be obtained in any of a variety of forms, e.g., in a buccal swab, in a blood sample, or in any type of tissue biopsy. The cell sample can be obtained from a living individual. The cell sample can be a post-mortem sample. Cells present in the cell sample can be living cells.

In some embodiments, a cell in a cell sample obtained from an individual is contacted with a GSK-3α and/or GSK-3β inhibitor, e.g., a compound of Formula I, e.g., Tideglusib or a pharmaceutically acceptable salt or derivative thereof, or a compound of Formula II, e.g., SB-216763 or a pharmaceutically acceptable salt or derivative thereof; and expression of an HIV-encoded gene product is detected. Gene products include nucleic acids (e.g., mRNA) and protein.

Methods of detecting nucleic acid gene products are well known in the art; any such method can be used in a subject detection method. For example, a hybridization method can be used, using a suitably labeled nucleic acid probe. Detection can be accomplished by any known method, including, but not limited to, in situ hybridization, PCR, RT-PCR, and "Northern" or RNA blotting, or combinations of such techniques, using a suitably labeled nucleic acid probe.

In some cases, a polymerase chain reaction (PCR) method (e.g., a reverse transcription-PCR method; a quantitative PCR method; etc.) is used, employing primers (e.g., pairs of primer oligonucleotides) that amplify an HIV gene. The primer nucleic acids are prepared using any known method, e.g., automated synthesis, and the like. The primer pairs are chosen such that they specifically amplify a cDNA copy of an mRNA encoding an HIV polypeptide.

Methods using PCR amplification can be performed on the DNA from a single cell, although it is convenient to use at least about $10^5$ cells. A detectable label may be included in the amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^3H$; etc. The label may be a two stage system, where the amplified DNA is conjugated to biotin, haptens, etc. having a high-affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

A number of methods are available for determining the expression level of a gene or protein in a particular sample. For example, detection may utilize staining of cells or histological sections with labeled antibodies, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a fluorescent compound, e.g. fluorescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

Methods of detecting polypeptide gene products are known in the art, and include, e.g., immunological assays such as an enzyme-linked immunosorbent assay (ELISA), a protein blot assay, a radioimmunoassay, and the like, where such assays employ an antibody specific for an HIV-encoded polypeptide.

A subject detection method can be used to detect the presence, in a cell sample obtained from an individual, of a cell harboring latent HIV. In some cases, detection in a cell sample obtained from a living individual of a cell harboring latent HIV may indicate that the individual should be treated with an agent that reactivates latent HIV. For example, the individual may be undergoing treatment for an HIV infection at the time the individual is subjected to a subject detection method; in such cases, the individual may be treated with both a treatment regimen for treating the HIV infection, and with an agent that reactivates latent HIV.

A subject detection method can be used to isolate primary cells harboring latent HIV. Such cells can be used in a subject screening method, as described below.

In some cases, a subject detection method further comprises isolating a cell that has been identified as harboring latent HIV in its genome.

Screening Methods

The present disclosure provides a method of identifying a candidate agent for treating an HIV infection in an individual. The method generally involves contacting a primary cell, identified using a detection method as described herein or using any suitable detection method known in the art, with a GSK-3α and/or GSK-3β inhibitor, e.g., a compound of Formula I, e.g., Tideglusib or a pharmaceutically acceptable salt or derivative thereof, or a compound of Formula II, e.g., SB-216763 or a pharmaceutically acceptable salt or derivative thereof, and a test agent; and determining the effect of the test agent on the level of HIV produced in the cell and/or the level of an HIV-encoded gene product in the cell. A test agent that reduces the level of HIV produced in the cell and/or the level of production of an HIV-encoded gene product, compared to the level of HIV produced and/or the level of an HIV-encoded gene product in a control cell contacted with the GSK-3α and/or GSK-3β inhibitor, e.g., the compound of Formula I, e.g., Tideglusib or the pharmaceutically acceptable salt or derivative thereof, or the compound of Formula II, e.g., SB-216763 or a pharmaceutically acceptable salt or derivative thereof, but not with the test agent, is considered a candidate agent for inhibiting HIV and treating an HIV infection.

A test agent that reduces level of HIV produced in the cell and/or the level of production of an HIV-encoded gene product by at least about 10%, at least about 20%, at least about 25%, at least about 30%, at least about 40%, at least about 50%, at least about 60%, at least about 70%, at least about 80%, or more than 80%, relative to a suitable control, is considered a candidate agent for treating an HIV infection.

As used herein, the term "determining" refers to both quantitative and qualitative determinations and as such, the term "determining" is used interchangeably herein with "assaying," "measuring," and the like.

The terms "candidate agent," "test agent," "agent", "substance" and "compound" are used interchangeably herein. Candidate agents encompass numerous chemical classes, typically synthetic, semi-synthetic, or naturally occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.) and can also be used. Alternatively, libraries of natural compounds in the form of bacterial, fungal, plant and animal extracts are available from Pan Labs (Bothell, Wash.) or are readily producible.

Candidate agents can be small organic or inorganic compounds having a molecular weight of more than 50 and less than about 2,500 daltons. Candidate agents can comprise functional groups necessary for structural interaction with proteins, e.g., hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, and derivatives, structural analogs or combinations thereof.

Exemplary Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-79 are provided below. As will be apparent to those of ordinary skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A method of reactivating a latent human immunodeficiency virus (HIV) integrated into the genome of a cell infected with HIV, the method comprising contacting the cell with a glycogen synthase kinase 3 inhibitor, wherein the glycogen synthase kinase 3 inhibitor reactivates the latent HIV integrated into the genome of the cell.

2. The method of 1, wherein the glycogen synthase kinase 3 inhibitor is a glycogen synthase kinase 3α inhibitor.

3. The method of 1, wherein the glycogen synthase kinase 3 inhibitor is a glycogen synthase kinase 3β inhibitor.

4. The method of 1, wherein the glycogen synthase kinase 3 inhibitor is an inhibitor of both glycogen synthase kinase 3α and glycogen synthase kinase 3β.

5. The method of any one of 1-4, wherein the contacting does not significantly reduce CD4⁺ T cell viability.

6. The method of any one of 1-5, wherein the contacting does not significantly reduce CD8⁺ T cell viability.

7. The method of any one of 1-6, wherein the contacting does not significantly reduce NK cell viability.

8. The method of any one of 1-7, wherein the contacting does not significantly increase CD4⁺ T cell activation.

9. The method of any one of 1-8, wherein the contacting does not significantly inhibit or enhances cytoxic effector functions of CTLs or NK cells.

10. The method of any one of 1-9, wherein the glycogen synthase kinase 3 inhibitor is:

a) a compound of Formula I:

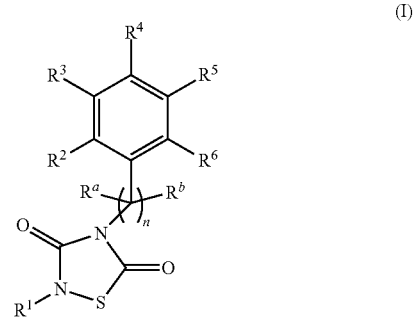

(I)

or a pharmaceutically acceptable salt, solvate or prodrug thereof, wherein:

n is an integer from 1 to 8;

each of $R^1$, $R^2$, $R^3$, $R^4$, $R^5$, $R^6$, $R^a$ and $R^b$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, —COR⁷, —C(O)OR⁷, —C(O)NR⁷R⁸, —C═NR⁷, —OR⁷, —OC(O)R⁷, —S(O)ₜ—R⁷, —NR⁷R⁸, —NR⁷C(O)R⁸, —N═CR⁷R⁸, wherein t is 0, 1, 2 or 3; and each of R⁷ and R⁸ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen; or b) a compound of Formula II:

(Formula II)

or a pharmaceutically acceptable salt, solvate or prodrug thereof, wherein:

$R^1$ and $R^2$ are independently $C_5$-$C_{12}$ cycloalkyl, substituted $C_5$-$C_{12}$ cycloalkyl, $C_5$-$C_{12}$ heterocycloalkyl, substituted $C_5$-$C_{12}$ heterocycloalkyl, $C_5$-$C_{12}$ aryl, substituted $C_5$-$C_{12}$ aryl, $C_5$-$C_{12}$ heteroaryl, substituted $C_5$-$C_{12}$ heteroaryl, wherein the compound of Formula I or the compound of Formula II reactivates the latent HIV integrated into the genome of the cell.

11. The method of 10, wherein the compound of Formula II is a compound of Formula IIa:

Formula IIa or a pharmaceutically acceptable salt, solvate or prodrug thereof, wherein:

$R^2$ are independently $C_5$-$C_{12}$ cycloalkyl, substituted $C_5$-$C_{12}$ cycloalkyl, $C_5$-$C_{12}$ heterocycloalkyl, substituted $C_5$-$C_{12}$ heterocycloalkyl, $C_5$-$C_{12}$ aryl, substituted $C_5$-$C_{12}$ aryl, $C_5$-$C_{12}$ heteroaryl, substituted $C_5$-$C_{12}$ heteroaryl;

each of $R^3$, $R^4$, $R^5$, $R^6$, $R^7$ and $R^8$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, —$COR^7$, —$C(O)OR^7$, —$C(O)NR^7R^8$, —$C=NR^7$, —$OR^7$, —$OC(O)R^7$, —$S(O)_t$—$R^7$, —$NR^7R^8$, —$NR^7C(O)R^8$, —$N=CR^7R^8$, wherein t is 0, 1, 2 or 3, 12. The method of 10, wherein the compound of Formula II is a compound of Formula IIb:

Formula IIb or a pharmaceutically acceptable salt, solvate or prodrug thereof, wherein:

each of $R^3$, $R^4$, $R^5$, $R^6$, $R^7$, $R^8$, $R^9$, $R^1$, $R^1$, $R^{12}$ and $R^{13}$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, —$COR^7$, —$C(O)OR^7$, —$C(O)NR^7R^8$, —$C=NR^7$, —$OR^7$, —$OC(O)R^7$, —$S(O)_t$—$R^7$, —$NR^7R^8$, —$NR^7C(O)R^8$, —$N=CR^7R^8$, wherein t is 0, 1, 2 or 3.

13. The method of any one of 1-9, wherein the glycogen synthase kinase 3 inhibitor is Tideglusib (4-benzyl-2-(naphthalen-1-yl)-1,2,4-thiadiazolidine-3,5-dione)) or pharmaceutically acceptable salt or derivative thereof or SB-216763 (3-(2,4-Dichlorophenyl)-4-(1-methyl-1H-indol-3-yl)-1H-pyrrole-2,5-dione) or pharmaceutically acceptable salt or derivative thereof.

14. The method of any one of 1-13, wherein the contacting occurs in lymphoid tissue.

15. A method of reducing the number of cells containing a latent human immunodeficiency virus in an individual, the method comprising administering to the individual an effective amount of a glycogen synthase kinase 3 inhibitor, wherein the glycogen synthase kinase 3 inhibitor reactivates latent HIV integrated into the genome of one or more cells in the individual.

16. The method of 15, wherein the glycogen synthase kinase 3 inhibitor is a glycogen synthase kinase 3α inhibitor.

17. The method of 15, wherein the glycogen synthase kinase 3 inhibitor is a glycogen synthase kinase 3β inhibitor.

18. The method of 15, wherein the glycogen synthase kinase 3 inhibitor is an inhibitor of both glycogen synthase kinase 3α and glycogen synthase kinase 3β.

19 The method of any one of 15-18, wherein the administering does not significantly reduce CD4+ T cell viability in the individual.

20. The method of any one of 15-19, wherein the administering does not significantly reduce CD8+ T cell viability in the individual.

21. The method of any one of claims 15-20, wherein the administering does not significantly reduce NK cell viability in the individual.

22. The method of any one of 15-21, wherein the administering does not significantly increase CD4+ T cell activation in the individual.

23. The method of any one of 15-22, wherein the administering does not significantly inhibit or enhances cytoxic effector functions of CTLs or NK cells in the individual.

24. The method of any one of 15-23, wherein the glycogen synthase kinase 3 inhibitor is:

a) a compound of Formula I:

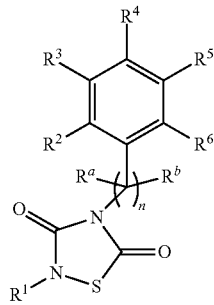

(I)

or a pharmaceutically acceptable salt, solvate or prodrug thereof, wherein:

n is an integer from 1 to 8;

each of $R^1$, $R^2$, $R^3$, $R^4$, $R^5$, $R^6$, $R^a$ and $R^b$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, —$COR^7$, —$C(O)OR^7$, —$C(O)NR^7R^8$, —$C=NR^7$, —$OR^7$, —$OC(O)R^7$, —$S(O)_t$—$R^7$, —$NR^7R^8$, —$NR^7C(O)R^8$, —$N=CR^7R^8$, wherein t is 0, 1, 2 or 3; and each of $R^7$ and $R^8$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen; or b) a compound of Formula II:

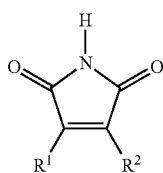

(Formula II)

or a pharmaceutically acceptable salt, solvate or prodrug thereof, wherein:

$R^1$ and $R^2$ are independently $C_5$-$C_{12}$ cycloalkyl, substituted $C_5$-$C_{12}$ cycloalkyl, $C_5$-$C_{12}$ heterocycloalkyl, substituted $C_5$-$C_{12}$ heterocycloalkyl, $C_5$-$C_{12}$ aryl, substituted $C_5$-$C_{12}$ aryl, $C_5$-$C_{12}$ heteroaryl, substituted $C_5$-$C_{12}$ heteroaryl.

25. The method of 24, wherein the compound of Formula II is a compound of Formula IIa:

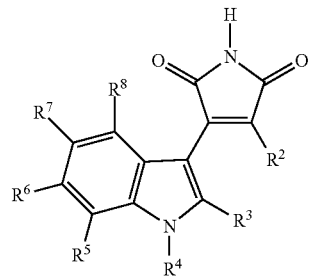

Formula IIa or a pharmaceutically acceptable salt, solvate or prodrug thereof, wherein:

$R^2$ are independently $C_5$-$C_{12}$ cycloalkyl, substituted $C_5$-$C_{12}$ cycloalkyl, $C_5$-$C_{12}$ heterocycloalkyl, substituted $C_5$-$C_{12}$ heterocycloalkyl, $C_5$-$C_{12}$ aryl, substituted $C_5$-$C_{12}$ aryl, $C_5$-$C_{12}$ heteroaryl, substituted $C_5$-$C_{12}$ heteroaryl;

each of $R^3$, $R^4$, $R^5$, $R^6$, $R^7$ and $R^8$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, —$COR^7$, —$C(O)OR^7$, —$C(O)NR^7R^8$, —$C=NR^7$, —$OR^7$, —$OC(O)R^7$, —$S(O)_t$—$R^7$, —$NR^7R^8$, —$NR^7C(O)R^8$, —$N=CR^7R^8$, wherein t is 0, 1, 2 or 3, 26. The method of 24, wherein the compound of Formula II is a compound of Formula IIb:

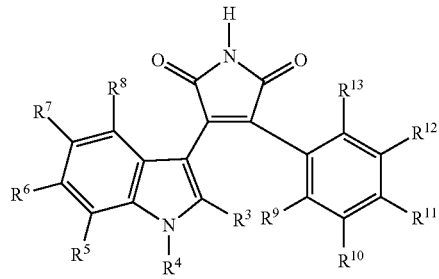

Formula IIb or a pharmaceutically acceptable salt, solvate or prodrug thereof, wherein:

each of $R^3$, $R^4$, $R^5$, $R^6$, $R^7$, $R^8$, $R^9$, $R^{10}$, $R^{11}$, $R^{12}$ and $R^{13}$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, —$COR^7$, —$C(O)OR^7$, —$C(O)NR^7R^8$, —$C=NR^7$, —$OR^7$, —$OC(O)R^7$, —$S(O)_t$—$R^7$, —$NR^7R^8$, —$NR^7C(O)R^8$, —$N=CR^7R^8$, wherein t is 0, 1, 2 or 3.

27. The method of any one of 15-23, wherein the glycogen synthase kinase 3 inhibitor is Tideglusib (4-benzyl-2-(naphthalen-1-yl)-1,2,4-thiadiazolidine-3,5-dione)) or pharmaceutically acceptable salt or derivative thereof or SB-216763 (3-(2,4-Dichlorophenyl)-4-(1-methyl-1H-indol-3-yl)-1H-pyrrole-2,5-dione) or pharmaceutically acceptable salt or derivative thereof.

28. The method of any one of 15-27, wherein said administering is effective to reduce the number of cells containing a latent human immunodeficiency virus in the individual by at least 20%.

29. A method of treating a human immunodeficiency virus (HIV) infection in an individual, the method comprising:
administering to an individual an effective amount of a glycogen synthase kinase 3 inhibitor, wherein the glycogen synthase kinase 3 inhibitor reactivates latent HIV integrated into the genome of a cell in the individual; and
administering to the individual an effective amount of a second active agent, wherein the second active agent inhibits an immunodeficiency virus function selected from viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity.

30. The method of 29, wherein the glycogen synthase kinase 3 inhibitor is a glycogen synthase kinase 3α inhibitor.

31. The method of 29, wherein the glycogen synthase kinase 3 inhibitor is a glycogen synthase kinase 3β inhibitor.

32. The method of 29, wherein the glycogen synthase kinase 3 inhibitor is an inhibitor of both glycogen synthase kinase 3α and glycogen synthase kinase 3β.

33. The method of any one of 29-32, wherein the administering does not significantly reduce CD4$^+$ T cell viability in the individual.

34. The method of any one of 29-33, wherein the administering does not significantly reduce CD8$^+$ T cell viability in the individual.

35. The method of any one of 29-34, wherein the administering does not significantly reduce NK cell viability in the individual.

36. The method of any one of 29-35, wherein the administering does not significantly increase CD4$^+$ T cell activation in the individual.

37. The method of any one of 29-36, wherein the administering does not significantly inhibit or enhances cytoxic effector functions of CTLs or NK cells in the individual.

38. The method of any one of 29-37, wherein the glycogen synthase kinase 3 inhibitor is:
a) a compound of Formula I:

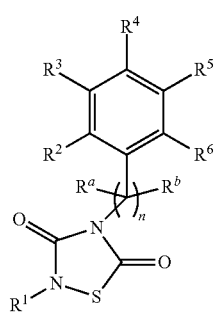

(I)

or a pharmaceutically acceptable salt, solvate or prodrug thereof, wherein:
n is an integer from 1 to 8;
each of $R^1$, $R^2$, $R^3$, $R^4$, $R^5$, $R^6$, $R^a$ and $R^b$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, —COR$^7$, —C(O)OR$^7$, —C(O)NR$^7$R$^8$, —C=NR$^7$, —OR$^7$, —OC(O)R$^7$, —S(O)$_t$—R$^7$, —NR$^7$R$^8$, —NR$^7$C(O)R$^8$, —N=CR$^7$R$^8$,
wherein t is 0, 1, 2 or 3; and
each of $R^7$ and $R^8$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen; or
b) a compound of Formula II:

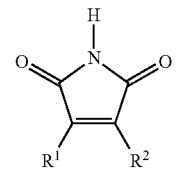

(Formula II)

or a pharmaceutically acceptable salt, solvate or prodrug thereof,
wherein:
$R^1$ and $R^2$ are independently $C_5$-$C_{12}$ cycloalkyl, substituted $C_5$-$C_{12}$ cycloalkyl, $C_5$-$C_{12}$ heterocycloalkyl, substituted $C_5$-$C_{12}$ heterocycloalkyl, $C_5$-$C_{12}$ aryl, substituted $C_5$-$C_{12}$ aryl, $C_5$-$C_{12}$ heteroaryl, substituted $C_5$-$C_{12}$ heteroaryl.

39. The method of 38, wherein the compound of Formula II is a compound of Formula IIa:

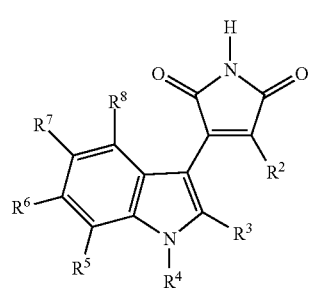

Formula IIa or a pharmaceutically acceptable salt, solvate or prodrug thereof,
wherein:
$R^2$ are independently $C_5$-$C_{12}$ cycloalkyl, substituted $C_5$-$C_{12}$ cycloalkyl, $C_5$-$C_{12}$ heterocycloalkyl, substituted $C_5$-$C_{12}$ heterocycloalkyl, $C_5$-$C_{12}$ aryl, substituted $C_5$-$C_{12}$ aryl, $C_5$-$C_{12}$ heteroaryl, substituted $C_5$-$C_{12}$ heteroaryl;
each of $R^3$, $R^4$, $R^5$, $R^6$, $R^7$ and $R^8$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, —COR$^7$, —C(O)OR$^7$, —C(O)NR$^7$R$^8$, —C═NR$^7$, —OR$^7$, —OC(O)R$^7$, —S(O)$_t$—R$^7$, —NR$^7$R$^8$, —NR$^7$C(O)R$^8$, —N═CR$^7$R$^8$, wherein t is 0, 1, 2 or 3, 40. The method of 38, wherein the compound of Formula II is a compound of Formula IIb:

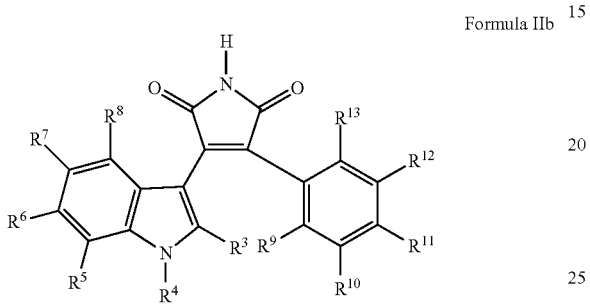

Formula IIb or a pharmaceutically acceptable salt, solvate or prodrug thereof, wherein:

each of R$^3$, R$^4$, R$^5$, R$^6$, R$^7$, R$^8$, R$^9$, R$^1$, R$^1$, R$^{12}$ and R$^{13}$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, —COR$^7$, —C(O)OR$^7$, —C(O)NR$^7$R$^8$, —C═NR$^7$, —OR$^7$, —OC(O)R$^7$, —S(O)$_t$—R$^7$, —NR$^7$R$^8$, —NR$^7$C(O)R$^8$, —N═CR$^7$R$^8$, wherein t is 0, 1, 2 or 3.

41. The method of any one of 29-37, wherein the glycogen synthase kinase 3 inhibitor is Tideglusib (4-benzyl-2-(naphthalen-1-yl)-1,2,4-thiadiazolidine-3,5-dione)) or pharmaceutically acceptable salt or derivative thereof or SB-216763 (3-(2,4-Dichlorophenyl)-4-(1-methyl-1H-indol-3-yl)-1H-pyrrole-2,5-dione) or pharmaceutically acceptable salt or derivative thereof.

42. The method of any one of 29-41, wherein one or both of said administering steps is by a vaginal route of administration, by a rectal route of administration, by an oral route of administration, or by an intravenous route of administration.

43. A drug delivery device comprising:

a) a first container comprising glycogen synthase kinase 3 inhibitor, wherein the glycogen synthase kinase 3 inhibitor reactivates latent immunodeficiency virus transcription; and b) a second container comprising an agent that inhibits an immunodeficiency virus function selected from viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity.

44. The device of 43, wherein the glycogen synthase kinase 3 inhibitor is a glycogen synthase kinase 3α inhibitor.

45. The device of 43, wherein the glycogen synthase kinase 3 inhibitor is a glycogen synthase kinase 3β inhibitor.

46. The device of 43, wherein the glycogen synthase kinase 3 inhibitor is an inhibitor of both glycogen synthase kinase 3α and glycogen synthase kinase 3β.

47. The device of any one of 43-46, wherein the glycogen synthase kinase 3 inhibitor is:

a) a compound of Formula I:

(I)

or a pharmaceutically acceptable salt, solvate or prodrug thereof, wherein:

n is an integer from 1 to 8;

each of R$^1$, R$^2$, R$^3$, R$^4$, R$^5$, R$^6$, R$^a$ and R$^b$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, —COR$^7$, —C(O)OR$^7$, —C(O)NR$^7$R$^8$, —C═NR$^7$, —OR$^7$, —OC(O)R$^7$, —S(O)$_t$—R$^7$, —NR$^7$R$^8$, —NR$^7$C(O)R$^8$, —N═CR$^7$R$^8$, wherein t is 0, 1, 2 or 3; and each of R$^7$ and R$^8$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen; or b) a compound of Formula II:

(Formula II)

or a pharmaceutically acceptable salt, solvate or prodrug thereof, wherein:

R$^1$ and R$^2$ are independently C$_5$-C$_{12}$ cycloalkyl, substituted C$_5$-C$_{12}$ cycloalkyl, C$_5$-C$_{12}$ heterocycloalkyl, substituted C$_5$-C$_2$ heterocycloalkyl, C$_5$-C$_2$ aryl, substituted C$_5$-C$_2$ aryl, C$_5$-C$_{12}$ heteroaryl, substituted C$_5$-C$_{12}$ heteroaryl.

48. The device of 47, wherein the compound of Formula II is a compound of Formula IIa:

Formula IIa

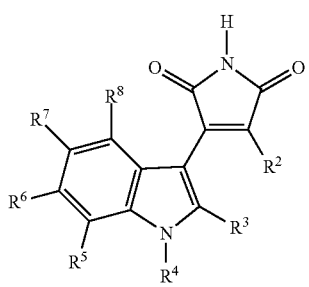

or a pharmaceutically acceptable salt, solvate or prodrug thereof,
wherein:
$R^2$ are independently $C_5$-$C_{12}$ cycloalkyl, substituted $C_5$-$C_{12}$ cycloalkyl, $C_5$-$C_{12}$ heterocycloalkyl, substituted $C_5$-$C_{12}$ heterocycloalkyl, $C_5$-$C_{12}$ aryl, substituted $C_5$-$C_{12}$ aryl, $C_5$-$C_{12}$ heteroaryl, substituted $C_5$-$C_{12}$ heteroaryl;
each of $R^3$, $R^4$, $R^5$, $R^6$, $R^7$ and $R^8$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, —$COR^7$, —$C(O)OR^7$, —$C(O)NR^7R^8$, —C=$NR^7$, —$OR^7$, —$OC(O)R^7$, —$S(O)_t$—$R^7$, —$NR^7R^8$, —$NR^7C(O)R^8$, —N=$CR^7R^8$, wherein t is 0, 1, 2 or 3, 49. The device of 47, wherein the compound of Formula II is a compound of Formula IIb:

Formula IIb

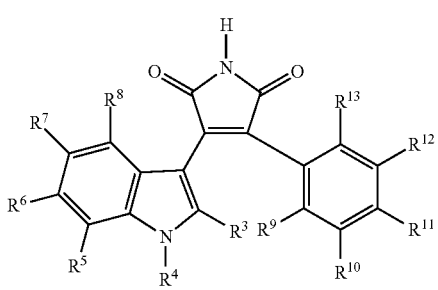

or a pharmaceutically acceptable salt, solvate or prodrug thereof,
wherein:
each of $R^3$, $R^4$, $R^5$, $R^6$, $R^7$, $R^8$, $R^9$, $R^{10}$, $R^{11}$, $R^{12}$ and $R^{13}$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, —$COR^7$, —$C(O)OR^7$, —$C(O)NR^7R^8$, —C=$NR^7$, —$OR^7$, —$OC(O)R^7$, —$S(O)_t$—$R^7$, —$NR^7R^8$, —$NR^7C(O)R^8$, —N=$CR^7R^8$, wherein t is 0, 1, 2 or 3.

50. The device of any one of 43-49, wherein the glycogen synthase kinase 3 inhibitor is Tideglusib (4-benzyl-2-(naphthalen-1-yl)-1,2,4-thiadiazolidine-3,5-dione)) or pharmaceutically acceptable salt or derivative thereof or SB-216763 (3-(2,4-Dichlorophenyl)-4-(1-methyl-1H-indol-3-yl)-1H-pyrrole-2,5-dione) or pharmaceutically acceptable salt or derivative thereof.

51. A method of identifying a candidate agent for treating a human immunodeficiency virus (HIV) infection in an individual, the method comprising:
contacting a cell comprising latent HIV with a test agent and a glycogen synthase kinase 3 inhibitor;
determining the effect of the test agent on the level of HIV produced in the cell and/or the level of an HIV-encoded gene product in the cell,
wherein a test agent that reduces the level of HIV produced in the cell and/or the level of production of an HIV-encoded gene product, compared to the level of HIV produced and/or the level of an HIV-encoded gene product in a control cell contacted with the glycogen synthase kinase 3 inhibitor in the absence of the test agent, is a candidate agent for treating an HIV infection.

52. The method of 51, wherein the glycogen synthase kinase 3 inhibitor is a glycogen synthase kinase 3α inhibitor.

53. The method of 51, wherein the glycogen synthase kinase 3 inhibitor is a glycogen synthase kinase 3β inhibitor.

54. The method of 51, wherein the glycogen synthase kinase 3 inhibitor is an inhibitor of both glycogen synthase kinase 3α and glycogen synthase kinase 3β.

55. The method of any one of 51-54, wherein the contacting does not significantly reduce CD4+ T cell viability.

56. The method of any one of 51-55, wherein the contacting does not significantly reduce CD8+ T cell viability.

57. The method of any one of 51-56, wherein the contacting does not significantly reduce NK cell viability.

58. The method of any one of 51-57, wherein the contacting does not significantly increase CD4+ T cell activation.

59. The method of any one of 51-58, wherein the contacting does not significantly inhibit or enhances cytoxic effector functions of CTLs or NK cells.

60. The method of any one of 51-59, wherein the glycogen synthase kinase 3 inhibitor is:
a) a compound of Formula I:

(I)

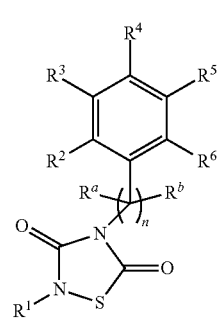

or a pharmaceutically acceptable salt, solvate or prodrug thereof,
wherein:
n is an integer from 1 to 8;
each of $R^1$, $R^2$, $R^3$, $R^4$, $R^5$, $R^6$, $R^a$ and $R^b$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, —COR$^7$, —C(O)OR$^7$, —C(O)NR$^7$R$^8$, —C=NR$^7$, —OR$^7$, —OC(O)R$^7$, —S(O)$_t$—R$^7$, —NR$^7$R$^8$, —NR$^7$C(O)R$^8$, —N=CR$^7$R$^8$, wherein t is 0, 1, 2 or 3; and each of R$^7$ and R$^8$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen; or b) a compound of Formula II:

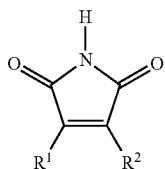

(Formula II)

or a pharmaceutically acceptable salt, solvate or prodrug thereof, wherein:

R$^1$ and R$^2$ are independently C$_5$-C$_{12}$ cycloalkyl, substituted C$_5$-C$_{12}$ cycloalkyl, C$_5$-C$_{12}$ heterocycloalkyl, substituted C$_5$-C$_{12}$ heterocycloalkyl, C$_5$-C$_{12}$ aryl, substituted C$_5$-C$_{12}$ aryl, C$_5$-C$_{12}$ heteroaryl, substituted C$_5$-C$_{12}$ heteroaryl.

61. The method of 60, wherein the compound of Formula II is a compound of Formula IIa:

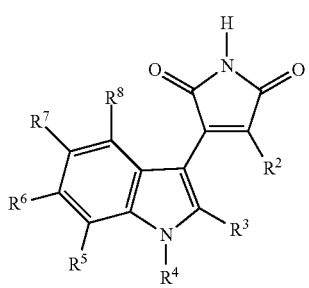

Formula IIa or a pharmaceutically acceptable salt, solvate or prodrug thereof, wherein:

R$^2$ are independently C$_5$-C$_{12}$ cycloalkyl, substituted C$_5$-C$_{12}$ cycloalkyl, C$_5$-C$_{12}$ heterocycloalkyl, substituted C$_5$-C$_{12}$ heterocycloalkyl, C$_5$-C$_{12}$ aryl, substituted C$_5$-C$_{12}$ aryl, C$_5$-C$_{12}$ heteroaryl, substituted C$_5$-C$_{12}$ heteroaryl;

each of R$^3$, R$^4$, R$^5$, R$^6$, R$^7$ and R$^8$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, —COR$^7$, —C(O)OR$^7$, —C(O)NR$^7$R$^8$, —C=NR$^7$, —OR$^7$, —OC(O)R$^7$, —S(O)$_t$—R$^7$, —NR$^7$R$^8$, —NR$^7$C(O)R$^8$, —N=CR$^7$R$^8$, wherein t is 0, 1, 2 or 3, 62. The method of 60, wherein the compound of Formula II is a compound of Formula IIb:

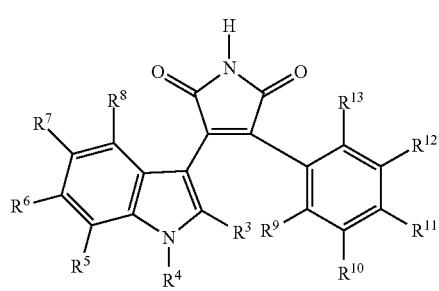

Formula IIb or a pharmaceutically acceptable salt, solvate or prodrug thereof, wherein:

each of R$^3$, R$^4$, R$^5$, R$^6$, R$^7$, R$^8$, R$^9$, R$^{10}$, R$^{11}$, R$^{12}$ and R$^{13}$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, —COR$^7$, —C(O)OR$^7$, —C(O)NR$^7$R$^8$, —C=NR$^7$, —OR$^7$, —OC(O)R$^7$, —S(O)$_t$—R$^7$, —NR$^7$R$^8$, —NR$^7$C(O)R$^8$, —N=CR$^7$R$^8$, wherein t is 0, 1, 2 or 3.

63. The method of any one of 51-59, wherein the glycogen synthase kinase 3 inhibitor is Tideglusib (4-benzyl-2-(naphthalen-1-yl)-1,2,4-thiadiazolidine-3,5-dione)) or pharmaceutically acceptable salt or derivative thereof or SB-216763 (3-(2,4-Dichlorophenyl)-4-(1-methyl-1H-indol-3-yl)-1H-pyrrole-2,5-dione) or pharmaceutically acceptable salt or derivative thereof.

64. A method of detecting in a cell sample a cell comprising latent human immunodeficiency virus (HIV), the method comprising:

a) contacting a cell sample obtained from an individual with a glycogen synthase kinase 3 inhibitor, wherein the glycogen synthase kinase 3 inhibitor reactivates latent immunodeficiency virus transcription; and b) detecting HIV gene expression in the cell, compared to HIV gene expression in a control cell not contacted with the agent, wherein detection of HIV gene expression in the cell contacted with the agent indicates that the cell comprises HIV.

65. The method of 64, wherein the glycogen synthase kinase 3 inhibitor is a glycogen synthase kinase 3α inhibitor.

66. The method of 64, wherein the glycogen synthase kinase 3 inhibitor is a glycogen synthase kinase 3β inhibitor.

67. The method of 64, wherein the glycogen synthase kinase 3 inhibitor is an inhibitor of both glycogen synthase kinase 3α and glycogen synthase kinase 3β.

68. The method of any one of 64-67, wherein the contacting does not significantly reduce CD4$^+$ T cell viability.

69. The method of any one of 64-68, wherein the contacting does not significantly reduce CD8+ T cell viability.

70. The method of any one of 64-69, wherein the contacting does not significantly reduce NK cell viability.

71. The method of any one of 64-70, wherein the contacting does not significantly increase CD4+ T cell activation.

72. The method of any one of 64-71, wherein the contacting does not significantly inhibit or enhances cytoxic effector functions of CTLs or NK cells.

73. The method of any one of 64-72, wherein the cell sample is obtained from lymphoid tissue.

74. The method of any one of 64-73, wherein the glycogen synthase kinase 3 inhibitor is:

a) a compound of Formula I:

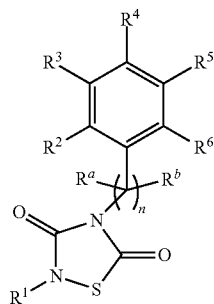

(I)

or a pharmaceutically acceptable salt, solvate or prodrug thereof,
wherein:
n is an integer from 1 to 8;
each of $R^1$, $R^2$, $R^3$, $R^4$, $R^5$, $R^6$, $R^a$ and $R^b$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, —$COR^7$, —$C(O)OR^7$, —$C(O)NR^7R^8$, —C=$NR^7$, —$OR^7$, —$OC(O)R^7$, —$S(O)_t$—$R^7$, —$NR^7R^8$, —$NR^7C(O)R^8$, —N=$CR^7R^8$,
wherein t is 0, 1, 2 or 3; and
each of $R^7$ and $R^8$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen; or b) a compound of Formula II:

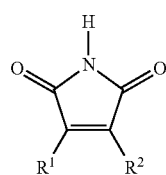

(Formula II)

or a pharmaceutically acceptable salt, solvate or prodrug thereof, wherein:
$R^1$ and $R^2$ are independently $C_5$-$C_{12}$ cycloalkyl, substituted $C_5$-$C_{12}$ cycloalkyl, $C_5$-$C_{12}$ heterocycloalkyl, substituted $C_5$-$C_{12}$ heterocycloalkyl, $C_5$-$C_{12}$ aryl, substituted $C_5$-$C_{12}$ aryl, $C_5$-$C_{12}$ heteroaryl, substituted $C_5$-$C_{12}$ heteroaryl.

75. The method of 74, wherein the compound of Formula II is a compound of Formula IIa:

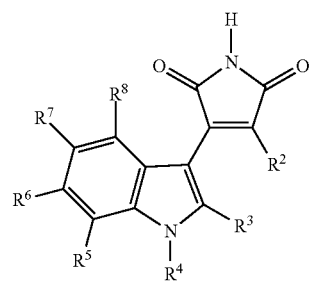

Formula IIa or a pharmaceutically acceptable salt, solvate or prodrug thereof,
wherein:
$R^2$ are independently $C_5$-$C_{12}$ cycloalkyl, substituted $C_5$-$C_{12}$ cycloalkyl, $C_5$-$C_{12}$ heterocycloalkyl, substituted $C_5$-$C_{12}$ heterocycloalkyl, $C_5$-$C_{12}$ aryl, substituted $C_5$-$C_{12}$ aryl, $C_5$-$C_{12}$ heteroaryl, substituted $C_5$-$C_{12}$ heteroaryl;
each of $R^3$, $R^4$, $R^5$, $R^6$, $R^7$ and $R^8$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, —$COR^7$, —$C(O)OR^7$, —$C(O)NR^7R^8$, —C=$NR^7$, —$OR^7$, —$OC(O)R^7$, —$S(O)_t$—$R^7$, —$NR^7R^8$, —$NR C(O)R^8$, —N=$CR^7R^8$, wherein t is 0, 1, 2 or 3, 76. The method of 74, wherein the compound of Formula II is a compound of Formula IIb:

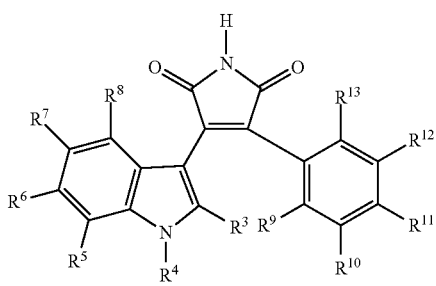

Formula IIb or a pharmaceutically acceptable salt, solvate or prodrug thereof,
wherein:
each of $R^3$, $R^4$, $R^5$, $R^6$, $R^7$, $R^8$, $R^9$, $R^{10}$, $R^{11}$, $R^{12}$ and $R^{13}$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, —COR$^7$, —C(O)OR$^7$, —C(O)NR$^7$R$^8$, —C═NR$^7$, —OR$^7$, —OC(O)R$^7$, —S(O)$_t$—R$^7$, —NR$^7$R$^8$, —NR$^7$C(O)R$^8$, —N═CR$^7$R$^8$, wherein t is 0, 1, 2 or 3.

77. The method of any one of 64-67, wherein the glycogen synthase kinase 3 inhibitor is Tideglusib (4-benzyl-2-(naphthalen-1-yl)-1,2,4-thiadiazolidine-3,5-dione)) or pharmaceutically acceptable salt or derivative thereof or SB-216763 (3-(2,4-Dichlorophenyl)-4-(1-methyl-1H-indol-3-yl)-1H-pyrrole-2,5-dione) or pharmaceutically acceptable salt or derivative thereof.

78. The method of any one of 64-77, further comprising isolating the cell from the sample.

79. The method of any one of 64-78, wherein detection of HIV gene expression comprises detecting an HIV-encoded gene product.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1: Reactivation of Latent HIV with the Glycogen Synthase Kinase 3β Antagonist Tideglusib (4-Benzyl-2-(Naphthalen-1-Yl)-1,2,4-Thiadiazolidine-3,5-Dione)

Materials and Methods

CD4$^+$ T cells were extracted from three HIV-1-infected individuals. The patients were selected by the SCOPE Study (See the website located by placing "https://" immediately preceding "hiv.ucsf.edu/research/scope.html") on the criteria of suppressive ART (antiretroviral treatment) and undetectable plasma HIV-1 RNA levels (<50 copies per ml) for a minimum of 6 months.

CD4$^+$ T cells were extracted from peripheral blood mononuclear cells (PBMCs) from continuous-flow centrifugation leukapheresis product and subsequent density centrifugation on a Ficoll-Hypaque gradient. Resting CD4$^+$ T lymphocytes were enriched by negative depletion with an EasySepHuman CD4$^+$ T Cell Isolation Kit (Stemcell). Cells were cultured in RPMI medium supplemented with 10% fetal bovine serum, penicillin/streptomycin and 5 μM Saquinavir. At least 5 million resting CD4$^+$ lymphocytes were stimulated with αCD3/CD28 beads, 0.01% (v/v) DMSO (negative control), or Tideglusib (TDG) diluted in DMSO at the indicated concentrations for 48 hours. For two different donors, SB-216763 treatment was compared with TDG treatment at the indicated concentrations. After LRA treatment, the supernatant was collected and spun down at 26,000 g for 2 hours. The pellet was then lysed and the RNA was extracted with an RNeasy kit (Quiagen). A Superscript III One-Step RT-PCR system was used to generate cDNA and concomitantly pre-amplify viral mRNA (i.e. 10-cycles pre-amplification) before analysis and quantification with digital droplet PCR (ddPCR).

Results

Figure 1:
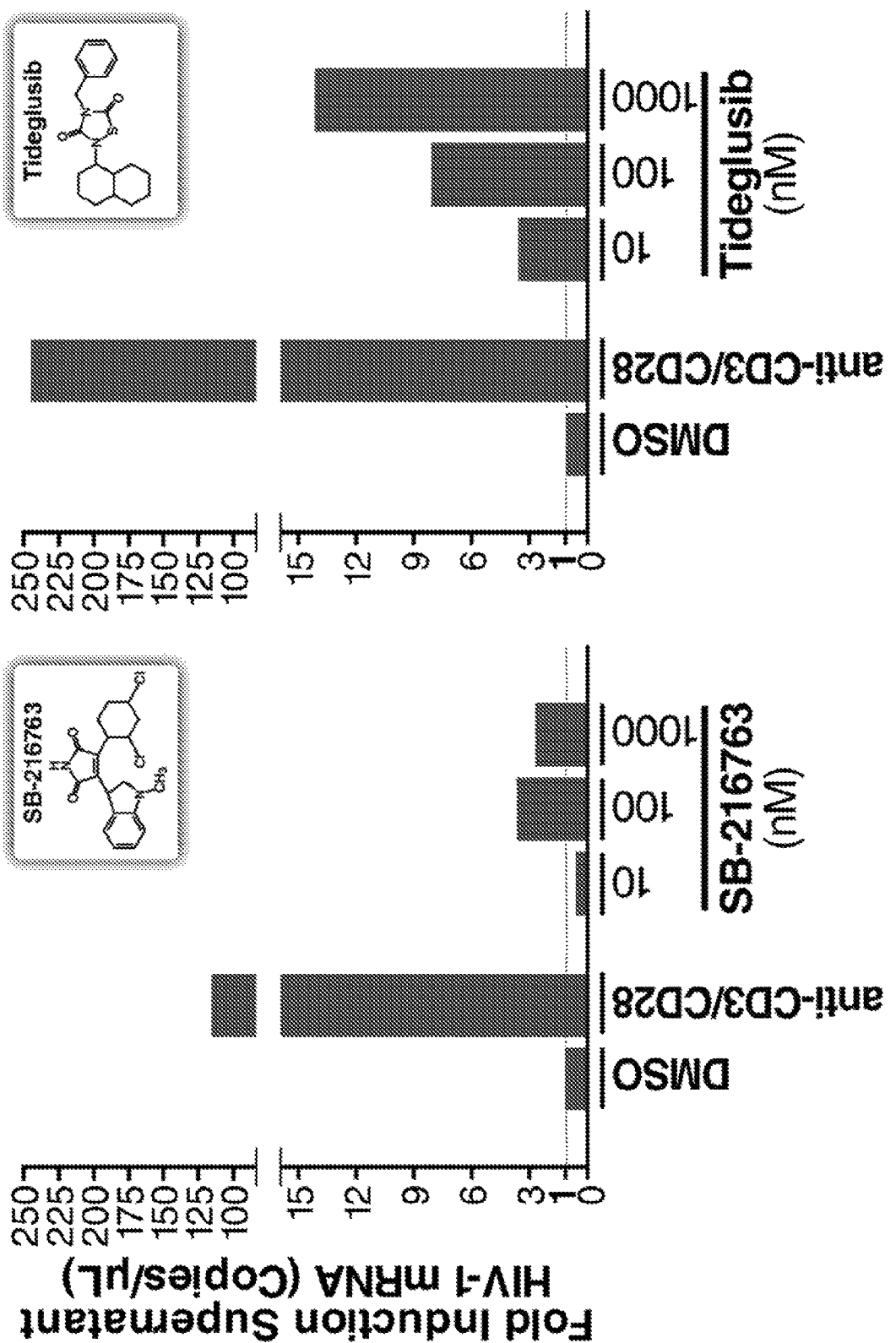
FIG. 1 depicts the effects of Tideglusib (right) and GSK-3α and β inhibitor SB-216763 (left) at three different concentrations on the reversal of HIV latency in primary CD4+ T cells isolated from an HIV-infected individual on antiretroviral therapy (ART) according to certain embodiments.
Figure 2:
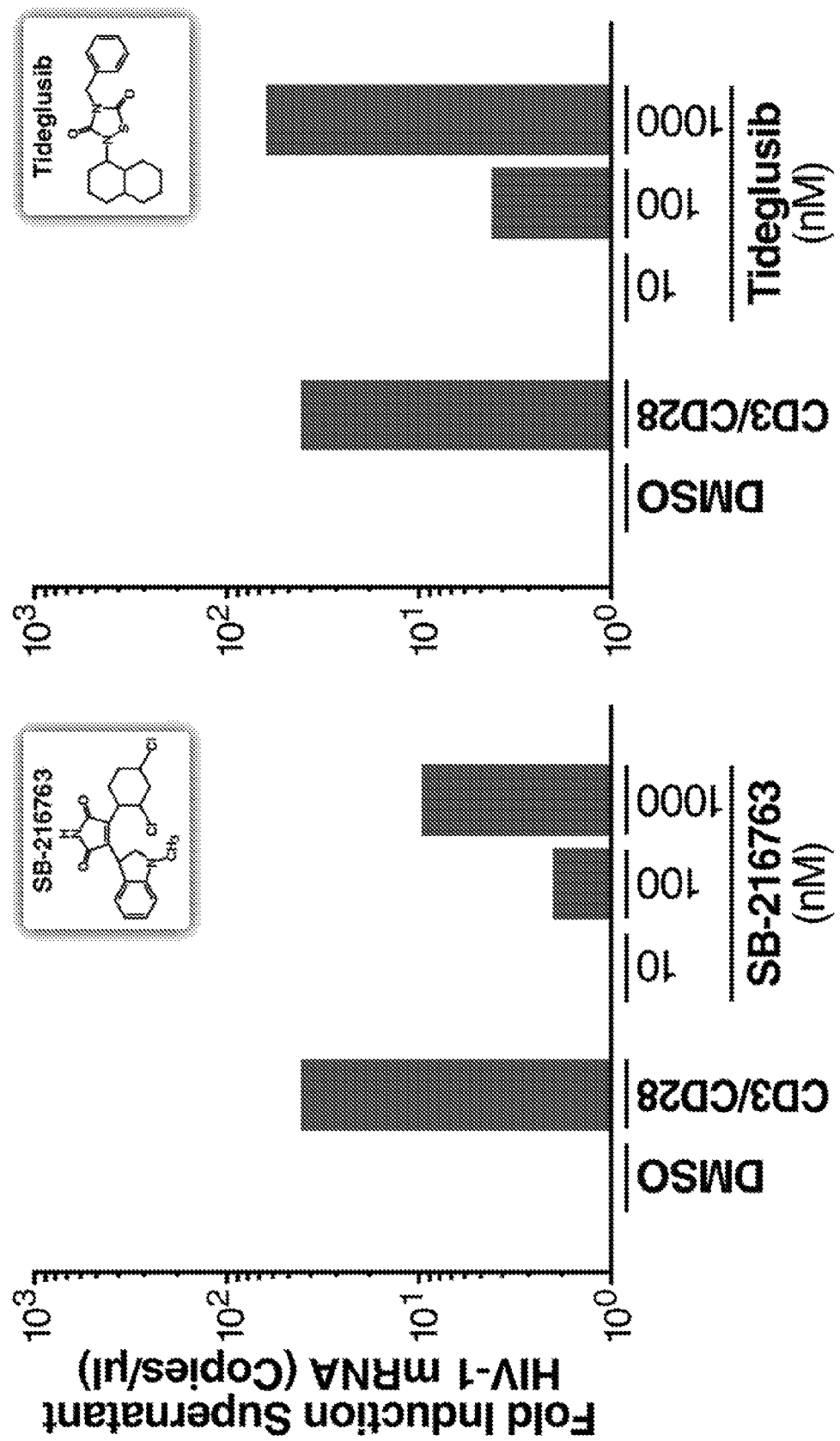
FIG. 2 depicts the effects of Tideglusib (right) and GSK-3α and β inhibitor SB-216763 (left) at three different concentrations on the reversal of HIV latency in CD4+ T cells isolated from a second HIV-infected donor on ART according to certain embodiments.

The efficacy of the glycogen synthase kinase 3β antagonist Tideglusib (4-benzyl-2-(naphthalen-1-yl)-1,2,4-thiadiazolidine-3,5-dione) on HIV latency reversion was tested. The results show a high level of reactivation of latent HIV from CD4$^+$ T cells upon ex vivo treatment with Tideglusib. This reactivation was even greater than that demonstrated with SB-216763, another GSK-3β inhibitor (FIGS. 1, 2 and 3A). As shown in FIGS. 1 and 2, treatment with 1 μM Tideglusib resulted in an average 30-fold increase (up to 60-fold induction in one donor) in viral mRNA released into the culture supernatant compared to untreated control (DMSO-treated cells).

Example 2: Viability of Patient-Derived CD4$^+$ T Cells Following Treatment with the GSK-3β Inhibitor Tideglusib Materials and Methods Following treatment with Tideglusib, the CD4$^+$ T cells were spun down and stained with the cell-death marker Zombie Violet (BioLegend). Briefly, cells were harvested 48 hours after LRA treatment, incubated with the Zombie dye for 15 minutes at room temperature, than washed and fixed with 1% PFA for 30 minutes; then washed again and analyzed via flow cytometer. Percentage of live (Zombie negative (−)) T Cells (CD3+) was normalized to the DMSO-treated control (DMSO or "untreated"=1).

Results

The percentage of zombie negative T cells (i.e. viable cells) measured at the flow cytometer for Tideglusib-treated CD4$^+$ T cells was similar to that for the untreated control, indicating that 48 h incubation with Tideglusib does not reduce cell-viability (FIG. 3B). In comparison, Panobinostat, a known latency-reversing agent, is highly toxic as shown in PCT/US2016/64614 (filed Dec. 2, 2016), the disclosure of which is incorporated by reference herein.

Example 3: Expression of Activation Markers in Patient-Derived CD4$^+$ T Cells Following Treatment with the GSK-3β Inhibitor Tideglusib Materials and Methods Following treatment with Tideglusib, the CD4$^+$ T cells were spun down and stained with antibodies for the activation markers CD69 and CD25. Briefly, cells were harvested 48 hours after Tideglusib treatment, incubated with the antibodies for 15 minutes at room temperature, than washed and fixed with 1% PFA for 30 minutes; then washed again and analyzed via flow cytometer.

Results

As shown in FIG. 3C, activation markers CD69 and CD25 (normalized to 100% upon treatment with anti-CD3/CD28 beads) are not up-regulated on the surface of patient derived CD4$^+$ T cells following treatment with Tideglusib, indicating a lack of increased cellular activation, which may be desirable in the context of HIV-1 latency reversion. In contrast, treatment with Bryostatin-1, a known latency-reversing agent, results in an increase in activation marker expression as shown in PCT/US2016/64614 (filed Dec. 2, 2016), the disclosure of which is incorporated by reference herein.

Example 4: Effect of the GSK-3β Inhibitor Tideglusib on CTL and NK Cell Function (Prophetic)

Lack of significant interference with the function of CTLs and NK cells is a potentially important characteristic for LRAs. Previous studies have confirmed enhancements in CTL response (Taylor et al. *Immunity.* 2016 Feb. 16; 44(2): 274-286) and NK-mediated killing (Parameswaran et al. *Nature Communications* 7, Article number: 11154 (2016) doi:10.1038/ncomms11154) as a result of GSK-3 inhibition, suggesting that Tideglusib should have a similar effect.

The effect of Tideglusib on CTL function may be determined using an HIV elimination assay modified from Jones et al. *PLoS Pathog.* 2014 Aug. 14; 10(8):e1004287. doi: 10.1371/journal.ppat. 1004287. eCollection 2014 August Briefly, HLA-A02$^+$ primary CD4$^+$ T-cells are infected with HIV JR-CSF and then co-cultured with HLA-A02-restricted HIV-specific CTL clone of defined epitope specificity that have been pre-treated for 2 hours with Tideglusib at various concentrations. Following a 16 hour co-culture in the continued presence of Tideglusib, the frequency of HIV-infected cells is determined by flow cytometry and compared this to co-cultures of untreated CTLs and infected CD4$^+$ cells in the absence of Tideglusib.

The effect of Tideglusib on CTL function may be determined using an HIV elimination assay modified from Garrido et al. *Front Immunol.* 2016 Sep. 21; 7:356. eCollection 2016. Briefly, CD4$^+$ T cells are isolated by negative selection in parallel to NK cells from each donor. Isolated CD4$^+$ T cells are activated during 24 h with 2 μg/mL PHA (Sigma Aldrich, St Louis, Mo., USA) and 60 U/mL IL-2 (Peprotech, Rocky Hill, Conn., USA). Cells are then infected with the JR-CSF viral strain by spinoculation for 90 min at 2500 rpm. After spinoculation, cells are extensively washed to remove free virions and 50,000 CD4$^+$ T cells are plated in triplicate for each condition in a 96-well plate. NK cells, previously exposed to LRAs or not (reference control), are added to the wells in an effector:target (E:T) ratio of 1:1, and left in culture for 7 days in cIMDM with 5 U/mL IL-2, with a media change at day 4. Viral production is assessed in the supernatant by p24 ELISA (ABL$_{inc}$, Rockville, Mass., USA), and percentage of viral inhibition of the different conditions is compared to inhibition from untreated NK cells.

These results shown above in Examples 1-4 indicate that Tidglusib is a new, highly efficient and non-toxic LRA for the reactivation of HIV latent reservoirs.

Example 5—Glycogen Synthase Kinase 3 Inhibitors—Non-Toxic and Non-T-Cell Activating HIV Latency Reversing Agents Materials and Methods
Study Participants HIV-1-infected individuals were enrolled at the Zuckerberg San Francisco General Hospital based on the criteria of suppressive ART and undetectable plasma HIV-1 RNA levels (<50 copies per ml) for a minimum of 6 months. Leukapheresis was performed through the UCSF SCOPE cohort for the collection of >1 billion Peripheral blood mononuclear cells (PBMCs).

Isolation and Culture of Peripheral Blood Mononuclear Cells, CD4$^+$ T Cells and Gut Associated Lymphoid Tissue Cells PBMCs were purified from whole blood or continuous flow centrifugation leukapheresis products via density centrifugation on a Ficoll-Hypaque gradient.

Subsequently, resting CD4$^+$ T cells were enriched by negative depletion with an EasySepHuman CD4$^+$ T Cell Isolation Kit (STEMCELL). Enriched cells were cultured in RPMI medium supplemented with 10% fetal bovine serum, penicillin/streptomycin. PBMCs and CD4$^+$ T cells from HIV-positive donors were cultured and treated in the presence of 5 μM saquinavir. For gut-associated lymphoid tissue (GALT) cells, to remove the epithelium and epithelial cells, 30 tissue biopsy tissue pieces were incubated in pre-warmed buffer containing 10 mM DTT, 5 mM EDTA, 10 mM HEPES and 5% FBS for 20 minutes at 37° C. under continuous rotation, vortexed and the supernatant aspirated. Tissue pieces were then incubated for a second time in the same pre-warmed buffer for a further 20 minutes at 37° C. under continuous rotation. The sample was again vortexed, and then rinsed for 20 minutes at 37° C. under continuous rotation with RMPI, 10 mM HEPES and 5% FBS. To then isolate lymphocytes from the lamina propria, a second, pre-warmed buffer containing RPMI, 10 mM HEPES, 7.5 g/ml DNAse and 5% FBS was applied to the tissue pieces, and these were again incubated for 20 minutes at 37° C. under continuous rotation. The samples were then vortexed, and aspirated numerous times with a blunt 20G needle until tissue was viably broken down. The cells were then rinsed twice with RMPI, 10 mM HEPES and 5% FBS and passed through a 70 μm cell strainer, pelleted and stained as described below for fluorescent activated sorting. GALT cells from HIV-positive donors were cultured and treated in the presence of 20 ng/ml enfuvirtide.

Drug Treatments

Anti-CD3/CD28 coated beads treatment was done at 25 μl per 1×10$^6$ cells (for bead-to-cell ratio=1:1); bryostatin-1 was used at 10 nM; panobinostat was used at 50 nM; SB-216763 (Tocris Bioscience) was used at 10/100/1000 nM; tideglusib (Selleckchem) was used at 10/100/1000 nM; SC79 (Tocris Bioscience) was used at 10/100/1000 nM; PP242 (Tocris Bioscience) was used at 250 nM; IKK-V (Millipore) was used at 25 nM, 2-DG (Sigma-Aldrich) was used at 50 mM, API-2 (Tocris Bioscience) was used at 250 nM.

Latency Reversing Agent Treatment Conditions and Measurement of Virus-Associated mRNA 5 million resting CD4$^+$ T lymphocytes were plated and either left unstimulated (media alone plus DMSO), stimulated with anti-CD3/CD28 coated or incubated with LRAs for 48 hours. The final DMSO percentage was never higher than 0.01% (v/v) for all treatments. Treated or untreated CD4$^+$ T cells. After treatment, cells were collected and spun down at 1000 rpm for 10 minutes in order to separate cells and supernatant: The cells were then subsequently used for assessment of viability and analysis of activation markers via flow cytometry; the supernatant was ultra-centrifuged at 26,000×g for 1.5 hours at 4° C. to purify released viruses. Pelleted viruses were re-suspended in RTL lysis buffer (qiagen) and RNA was extracted with an RNeasy mini kit (qiagen), according to manufacturer's protocol. The extracted RNA were then reverse-transcribed with a Superscript III One-Step RT-PCR system (Life Technologies), using the same primers as for ddPCR analysis (see below). Reaction mixes contained 15 μl of a PCR mix containing reaction mix, Superscript III, primers (900 nM final concentration) and 10 μl purified RNA. Pre-amplification was carried out using the following steps: reverse transcription at 50° C. for 30 min, denaturation at 95° C. for 2 min, 10-15 cycles of amplification (94° C. 15 sec, 55° C. 30 sec, 68 C 30 sec) on a GeneAmp PCR system 9700 (ThermoFisher). Subsequently, ddPCR was applied to quantify pre-amplified cDNA. Each 25 mL ddPCR mix comprised the ddPCR Probe Supermix (no dUTP), 900 nM primers, 250 nM probe, and 8 µl cDNA. The following cycling conditions were used: 10 min at 95° C., 40 cycles each consisting of 30 sec denaturation at 94° C. followed by 59.4° C. extension for 60 sec, and a final 10 min at 98° C. Reaction mixes were loaded into the Bio-Rad QX-100 emulsification device and droplets were formed following the manufacturer's instructions. Then, samples were transferred to a 96-well reaction plate and sealed with a pre-heated Eppendorf 96-well heat sealer for 10 sec, as recommended by Bio-Rad. Finally, samples were amplified on a BioRad C1000 Thermocycler and analyzed using a BioRad QX100 ddPCR Reader. Primers and probe used for HIV-1 mRNA reverse transcription and ddPCR analysis were chosen as previously described (ref Laird et al., 2015):

```
forward (5'->3')
CAGATGCTGCATATAAGCAGCTG (9501-9523);

reverse (5'->3')
TTTTTTTTTTTTTTTTTTTTTTGAAGCAC (9629-poly A);

probe (50/30)
FAM-CCTGTACTGGGTCTCTCTGG-MGB (9531-9550).
```

Analysis of CD4+ T Cell Viability

25 µl from each well/treatment were incubated with Cell Titer Blue reagent (Promega) for 3 to 4 hours at 37° C. The assay is based on the ability of living cells to convert a redox dye (resazurin) into a fluorescent end product (resorufin). Colorimetric analysis of treated cells was done with a Perkin Elmer EnSpire 2300 Multimode plate reader set to detect fluorescence (Ex:579 nm/Em:584 nm).

Cytokines Release Assay

Supernatant was collected from the treated cell cultures described above and stored at −80° C. for later analysis. Supernatant cytokine levels were determined using a V-PLEX Proinflammatory Panel 1 (human) Kit (#K15049D-1) and a V-PLEX IL-17A Gen. B (human) (#K151WMD) from Meso Scale Discovery, following the manufacturer's protocol. The assay was done on undiluted supernatant samples in order to increase the sensitivity of the assay.

RNA and Protein Expression Profiling with Nanostring

Quantitative RNA and protein expression data were generated using the nCounter Vantage 3D Solid Tumor Assay and the nCounter SPRINT profiler (NanoString Technologies), comprising 770 RNA and 30 protein targets including positive and negative controls. 1-3 million negatively selected primary CD4+ T cells purified from HIV-positive donors on suppressive ART, as described above, were treated with 1 µM tideglusib or left untreated (DMSO control). Samples were then collected after different time points: 0.25, 0.5, 1, or 6 hours, and RNA and protein lysates prepared according to the manufacturer's instructions. For RNA samples, an additional RNA purification step (Qiagen miRNeasy Mini Kit) was necessary to ensure an appropriate sample input for the nCounter assay. A total of at least 30 ng RNA was used for each sample. Otherwise, samples were processed according to the manufacturer's instructions. RNA and protein expression values were normalized and analyzed using the nSolver Analysis Software 4.0 and the add-on Advanced Analysis Software 2.0.115 (NanoString Technologies). Normalization genes for each sample were automatically selected by the software based on the geNorm algorithm (ref vandesompele). Biological replicates were then grouped according to treatment and the differential expression of each analyte-type (RNA or protein target) was determined in comparison to the untreated condition by considering inter-donor differences as confounding variables. Based on the differential expression of each gene, pre-defined gene sets by nanoString, representing different pathways included in this assay, were analyzed by calculating global significance scores for each gene set within each treatment, as follows:

$$\text{Global significance statistic} = \left(\frac{1}{p}\sum_{i=1}^{p} t_i^2\right)^{\frac{1}{2}},$$

where $t_i$ is the t-statistic from the $i^{th}$ pathway gene.

The directed global significance statistic is similar to the global significance statistic, but rather than measuring the tendency of a pathway to have differentially expressed genes, it measures the tendency to have over- or under-expressed genes. It is calculated similarly to the undirected global significance score, but it takes the sign of the t-statistics into account:

Directed global significance statistic=$\text{sign}(U)|U|^{1/2}$ where $$U = \left(\frac{1}{p}\sum_{i=1}^{p}\text{sign}(t_i)*t_i^2\right)$$

and where sign(U) equals −1 if U is negative and 1 if U is positive.

Mass Spectrometry Analysis

Cells were lysed in a buffer containing 8M urea, 100 mM Tris pH 8.0, 150 mM NaCl, and protease inhibitors (Roche Complete tablet). Lysates were reduced with 4 mM TCEP for 30 minutes at room temperature and alkylated with 10 mM iodoacetamide for 30 minutes at room temperature in the dark. Samples were diluted 1:4 in 100 mM Tris pH 8.0 to reduce urea concentration to 2M and digested with trypsin (1:100 enzyme:substrate ratio) overnight at 37 degrees Celsius. Peptides were desalted with SepPak C 18 solid phase extraction (Waters) according the manufacturer's specifications and lyophilized to dryness. Phosphopeptides were purified using an immobilized metal affinity chromatography approach.

Samples were analyzed on a Thermo Scientific LTQ Orbitrap Elite MS system equipped with an Easy nLC-1000 HPLC and autosampler system that is capable of maintaining back pressures of up to 10,000 psi for high resolution chromatographic separations. The HPLC interfaces with the MS system via a nanoelectrospray source.

Samples were injected onto a C18 reverse phase capillary column (75 um inner diameter×25 cm length, packed with 1.9 um C18 particles). Peptides were then separated by an organic gradient from 5% to 30% ACN in 0.1% formic acid over 180 minutes at a flow rate of 300 nl/min. The MS continuously collected spectra in a data-dependent fashion over the entire gradient.

Raw mass spectrometry data were analyzed using the MaxQuant software package (version 1.3.0.5). Data were matched to the SwissProt human reference sequence database. MaxQuant was configured to generate and search against a reverse sequence database for false discovery rate calculations. Variable modifications were allowed for methionine oxidation, protein N-terminus acetylation, and serine, threonine, or tyrosine phosphorylation. A fixed modification was indicated for cysteine carbamidomethylation. Full trypsin specificity was required. The first search was performed with a mass accuracy of +/−20 parts per million and the main search was performed with a mass accuracy of +/−6 parts per million. A maximum of 5 modifications were allowed per peptide. A maximum of 2 missed cleavages were allowed. The maximum charge allowed was 7+. Individual peptide mass tolerances were allowed. For MS/MS matching, a mass tolerance of 0.5 Da was allowed and the top 6 peaks per 100 Da were analyzed. MS/MS matching was allowed for higher charge states, water and ammonia loss events. Data were searched against a concatenated database containing all sequences in both forward and reverse directions with reverse hits indicating the false discovery rate of identifications. The data were filtered to obtain a peptide, protein, and site-level false discovery rate of 0.01. The minimum peptide length was 7 amino acids. Results were matched between runs with a time window of 2 minutes for technical duplicates.

The MaxQuant-analyzed data were subsequently analyzed using an in-house computational pipeline for statistical analysis of relative quantification with fixed and/or mixed effect models, implemented in the MSstats Bioconductor package (version 3.3.10). Contaminants, decoy hits, and peptides not containing phosphorylated residues were removed and all samples were normalized by median-centering the log 2-transformed MS1-intensity distributions. Then, the MSstats groupComparison function was run with the following options: no interaction terms for missing values, no interference, unequal intensity feature variance, restricted technical and biological scope of replication.

Analysis of NF-κB (p65) Binding with Target DNA Sequences

To determine the specific NF-κB p65 DNA binding activity of treated CD4$^+$ T cells, an aliquot of the same nuclear extracts used for the p65/TBP western blots were submitted to the Transcription Factor Assay kit (Abcam, catalogue no. ab133112). Following the manufactures instructions sequentially, nuclear extracts were incubated in the TFA 96 well plate coated with double strand DNA NF-κB oligos. The wells were washed then incubated with primary anti-p65 antibody that is then detected by incubation with HRP conjugated secondary antibody. Developing reagents are added and absorbance is read at 450 nM. The level of absorbance indicates the DNA binding activity. For each donor experiment, binding specificity controls include a NF-κB competitor dsDNA control well and a non-specific binding control well. The assay was performed on 3 different donor samples.

GO Enrichment Analysis of Phosphoproteomics Data

GO enrichment analysis of the A set of 142 unique gene names was extracted from the differential analysis of 1 μM tideglusib vs untreated phosphoproteomics results using cutoffs of log 2 fold change >1 or <−1 and p-Value <0.05 and translated from UniProt identifiers to HGNC symbols. The gene set was submitted to Enrichr for enrichment analysis against dozens of public ontologies and annotated gene sets (PMC4987924). Tabular enrichments results were downloaded for WikiPathways and Gene Ontology:Biological Process (PMC5753270, PMC3037419) and selected terms were plotted using R based on relevance, uniqueness and combined score. The combined score is the product of −log p-Value and Z-score.

Analysis of Basal and Compensatory Glycolysis

ECAR was determined using the Seahorse SF Glycolytic Rate Assay Kit (Agilent, 103344-100) and a Seahorse XF96 Extracellular Flux Analyzer (Seahorse Bioscience). Resting (2×105 per well) were seeded onto Cell-Tak-coated wells (354240; Corning) in buffered Seahorse XF RPMI medium (Agilent, 103576-100) supplemented with 10 mM glucose, 2 mM L-glutamine, 1 mM pyruvate and 5 mM HEPES (pH 7.4). Measurements were obtained under basal conditions and after adding 0.5 μM rotenone/antimycin A (103015-100; Seahorse Bioscience), and 2-deoxy-d-glucose (2-DG) at a final well concentration of 50 mM (Agilent Technologies). Basal glycolysis and Proton Efflux Rate (PER) were calculated according to. Lactate measurements were detected using the Cayman L-Lactate Assay Kit (Cayman Chemical, 70010) In brief, 24 hours post treatment, supernatant from 200.000 primary resting and activated CD4$^+$ T cells was harvested and measured according to the manufacturer's recommendation.

Western Blot Analysis

For Analysis of Phosphor-GSK-3β:

Proteins were extracted from cells with RIPA buffer (diluted from 10× stock solution, Sigma Aldrich cat #20-188) with Protease and Phosphatase Inhibitors (Roche) added according to manufacturers instructions. Laemmli 2× buffer was added to prepare the SDS PAGE samples. Whole-cell lysates were run on NuPage 4-12% gradient Bis-Tris gels with loading of equal cell numbers per lane and transferred to PVDF membrane (Bio-Rad). Membranes were blocked for 1 hour in TBST+5% BSA, followed by primary antibody incubation overnight at 4 C, a 1 hour wash period, secondary antibody incubation (1 hour at RT, with anti-rabbit, HRP-conjugated antibodies (SouthernBiotech) diluted 1:10,000 in TBST+5% BSA+2.5% milk), and a final 2 hour wash period. Protein levels were assessed using the following primary antibodies: p-S9-GSK3β (CST #9323) and pan-GSK3β (CST #9315). Blots were developed using Chemiluminescent Western Blot detection ECL (PerkinElmer) or Luminata Forte (Millipore).

For Analysis of p65:

Nuclear extracts were prepared from purified CD4$^+$ T cells using the NE-PER Nuclear and Cytoplasmic Extraction reagent supplemented with protease inhibitor cocktail, as specified by the manufacturers protocol (Thermoscientific, catalogue no. 78833). Protein concentration of extracts was determined by Biorad protein assay (Biorad, catalogue no. 5000001). Nuclear extracts were resolved by electrophoresis on a 10% SDS-polyacrylamide gel using 15 μg of protein per condition and then transferred to PVDF membrane. Membranes were immunoblotted with primary antibodies for p65 (Cell signal Tech., catalogue no. 8242) and TATA binding protein (Abcam, catalogue no. ab63766); primary antibodies were diluted at 1:1000. Detection of primary antibodies was achieved by incubation with HRP conjugated secondary antibody. Bands were visualized by chemiluminescent detection using Immobilon Forte Western HRP ECL substrate (Millipore, catalogue no. WBLUF0100) followed by exposure to hyperfilm ECL (GE/Amersham, catalogue no. 45001508).

Lactate Production Analysis

CD4$^+$ T cells isolated from 3 HIV-negative donors were treated for 24 hours at 37° C. as indicated in the text either in normal RPMI or in media+50 mM 2-deoxy-D-glucose (2-DG). Subsequently, media of the treated samples were tested for production of L-lactated using a Glycolysis Cell-Based Assay Kit (Cayman Chemical). This test measures the quantity of formazan, an artificial chromogenic dye that results from the reduction of tetrazolium salts in the presence of NADH in the culture media. Colored formazan absorbs between 490 and 520 nm and can be detected by a plate reader. Since lactate dehydrogenase catalyzes the reaction between NAD+ and lactate, yielding pyruvate and NADH, which directly reduces the tetrazolium salt, the quantity of formazan produced is proportional to the quantity of L-lactate in the culture medium, and is thus an indirect measurement of glycolysis. In order to determine specific L-Lactate concentration, a standard curve was obtained analyzing absorbance of known concentration of L-lactate as indicated in the manufacturer's protocol.

Flow Cytometry

Freshly isolated PBMCs or CD4+ T cells were stained for viability, using the fixable viability dye Zombie violet (1:50, Biolegend) according to the manufacturer's recommendation. Surface staining was performed with the following antibodies at 1:100 dilutions: CD3-PE-Cy7, CD4-APC-Cy7, CD69-FITC, CD25-PE (all 1:100, Biolegend), and Glut-1-Ax647 (BD Bioscience, 566580) in staining buffer for 20 min on ice and cells were fixed in 1% PFA-containing PBS. All flow analysis was performed on the LSRII (BD Biosciences) using FlowJo software (v.10.4.2). Color compensations were performed using single-stained samples for each of the fluorochromes used. Data were analyzed using FlowJo software (TreeStar, San Carlos, Calif.).

Assessment of CD8 T-Cell Cytotoxic Effector Functions

After drug treatment, human PBMCs were cultured in complete RPMI in the presence of CD107a-BV650 (1:50, 328637, BioLegend) or CD107a-FITC antibodies (1:50, 555800, BD Bioscience) and PMA/ionomycin (50 ng/ml and 1 uM) dor 3.5 hours, adding Brefeldin A and Monensin (eBioscience) for the last hour. Cells were subsequently stained for viability using the viability dyes eFluor 506, (eBioscience) according to the provided protocol. After surface marker staining with the following antibodies (all at 1:100 dilution): CD3-APC-H7 (560176; BD Biosciences), CD8-V450 (560347; BD Biosciences), CD45RA-APC (17-0458; eBioscience), and CCR7-PE-Cy7 (557648; BD Biosciences), cells were permeabilized and fixed using the Foxp3/Transcription Factor Fixation/Permeabilization Concentrate and Diluent kit (eBioscience). Intracellular staining was performed with IFN-γ-PerCP-Cy5.5 antibody (1:100, 560704, BD Bioscience) in FOXP3 perm/wash buffer for 1 h at 4° C. After washing and fixation of the cells in 1% paraformaldehyde/PBS, cells were analyzed by flow cytometry. Final data stems from having gated on CD8hi- and CD8lo-expressing T cells.

Assessment of NK Cell Cytotoxic Effector Functions

Density centrifugation using a Ficoll-Hypaqua gradient was performed to purify PBMCs from continuous-flow centrifugation leukapheresis product. Subsequently, cells were plated in 96-well U-bottom plated in complete RPMI, which was supplemented with 10 ng/ml recombinant IL-15 (R&D systems), treated with LRAs or vehicle controls (DMSO) and incubated at 37° C., 5% CO2 for 48 h. To assay NK cell functionality, cells were analyzed by flow cytometry. Briefly, 1×10^6 cells/200 ul were stained with FITC anti-CD107 antibodies (1:50, BD Biosciences), mixed with 1×105 K562 cells and incubated at 37° C., 5% CO2 for 1 h. Then, in order to enhance intracellular cytokine staining, protein transport was blocked with Brefeldin A (Sigma-Aldrich) and golgi stop (BD Biosciences) according to the manufacturer instructions and the cells were incubated at 37° C., 5% CO2 for another 5 h. Afterwards, cells were spun down (5 min, 330×g, RT), the supernatant was removed and the cells were stained using Zombie violet (1:50, Biolegend) according to the manufacturer protocol. Subsequently, cells were stained for surface proteins staining with the following antibodies: APC/Cy7 anti CD3 (1:100, Biolegend), APC anti CD14 (1:100, Biolegend), APC anti CD19 (1:100, Biolegend), PE/Cy7 anti CD56 (1:100, BD Biosciences), Alexa Fluor 700 anti CD16 (1:100, Biolegend), PE anti CD7 (1:50, Thermo Fisher Scientific) for 15 min at room temperature. Next, cells were permeabilized and fixed using the Foxp3/Transcription Factor Fixation/Permeabilization Concentrate and Diluent kit (eBioscience) and stained intracellularly with PerCP/Cy5 anti IFN-γ (1:50, BD Bioscience) in FOXP3 perm/wash buffer for 1 h at 4° C. Finally, cells were washed and fixed in 1% paraformaldehyde/PBS, and subjected to flow cytometry analysis on a LSRII (BD Biosciences). Data were obtained using FlowJo software (Treestar). Samples were gated for singlets, live, CD3 negative, CD14/CD19 negative and CD7 positive cells as previously described (York, Milush). CD16high/CD56dim, CD16dim/CD56high cells were considered for analysis of IFN-γ and CD107a positivity. All gates were defined, based on fluorescence minus one (FMO) samples.

Granzyme B Cytotoxicity Assay and Infected CD4+ T-Cell Elimination (ICE)

PBMCs were co-incubated with HIVSF162-infected autologous CD4+ T-cell targets (E:T 25:1)+/−tideglusib at a final concentration of 1 CpM in 96 deep (1 mL) well plates for 6 days. As before, cultured day 6 cells were then labeled with immuno-magnetic beads (CD8 T-cell Isolation Kit II, Miltenyi Biotec) prior to negative selection of CD8+ T-cells by magnetic automated cell sorting (ref Migueles et al., 2008, 2009). Cytotoxic responses were measured against LIVE/DEAD Fixable Violet Stain (Molecular Probes, Invitrogen Detection Technologies, Eugene, Oreg., USA)-labeled HIVSF162-infected or uninfected autologous CD4+ T-cell targets in assays examining GrB target cell activity and infected CD4+ T-cell elimination (ICE) as previously reported (ref Migueles et al., 2008, 2009). Cells were analyzed on a FACSAria multi-laser cytometer (Becton-Dickinson) with FACSDiva software. Gates were drawn on labeled CD4+ T-cell targets and 5,000-15,000 events were collected. Color compensations were performed using single-stained samples for each of the fluorochromes used. Data were analyzed using FlowJo software (TreeStar, San Carlos, Calif.).

Statistical Analysis

Comparisons were carried out group-wise and calculated using a ratio paired Student's t test (comparing populations derived from the same donor). Unless differently indicated, data are presented as mean±SEM. Statistical significance is indicated in all figures by the following annotations: *, $P<0.05$; , $P<0.01$; *, $P<0.001$; ****, $P<0.0001$.

Results

GSK-3 Inhibitors Induce Latency Reversion Ex Vivo in Blood and Gut Tissue from HIV-Positive Donors on ART, in a Manner Dependent of mTOR and NF-κB To test GSK-3 inhibition on HIV latency reversion, 5 million purified CD4+ T cells from infected individuals on suppressive ART were treated with anti-CD3/CD28-coated beads (25 μl per 1×106 cells for bead-to-cell ratio=1:1), single LRAs or vehicle control (DMSO) for 48 hours. Subsequently, viruses released in the supernatant were collected and quantified with droplet digital PCR (ddPCR) levels of virus-associated HIV-1 mRNA with a primer/probe set that detects the 3' sequence common to all correctly terminated HIV-1 mRNAs. Quantitating virus production represents functional viral replication better than cell-associated viral RNA and allows predictions about how LRA therapy would affect a readily measurable clinical parameter, plasma HIV-1 RNA, in an established model of viral dynamics.

Figure 4A:
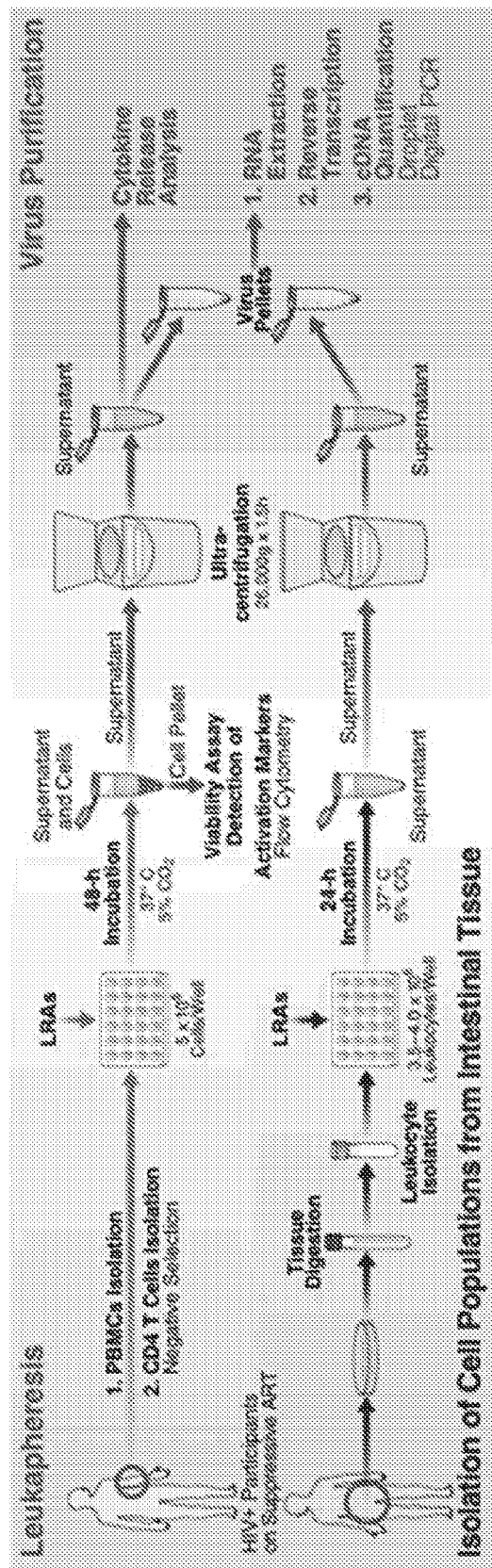
FIGS. 4A-4D depict inhibition of GSK-3 that leads to mTOR- and NF-κB-dependent latency reversion ex vivo in blood and gut tissue from HIV-positive donors on antiretroviral therapy (ART).
Figure 4B:
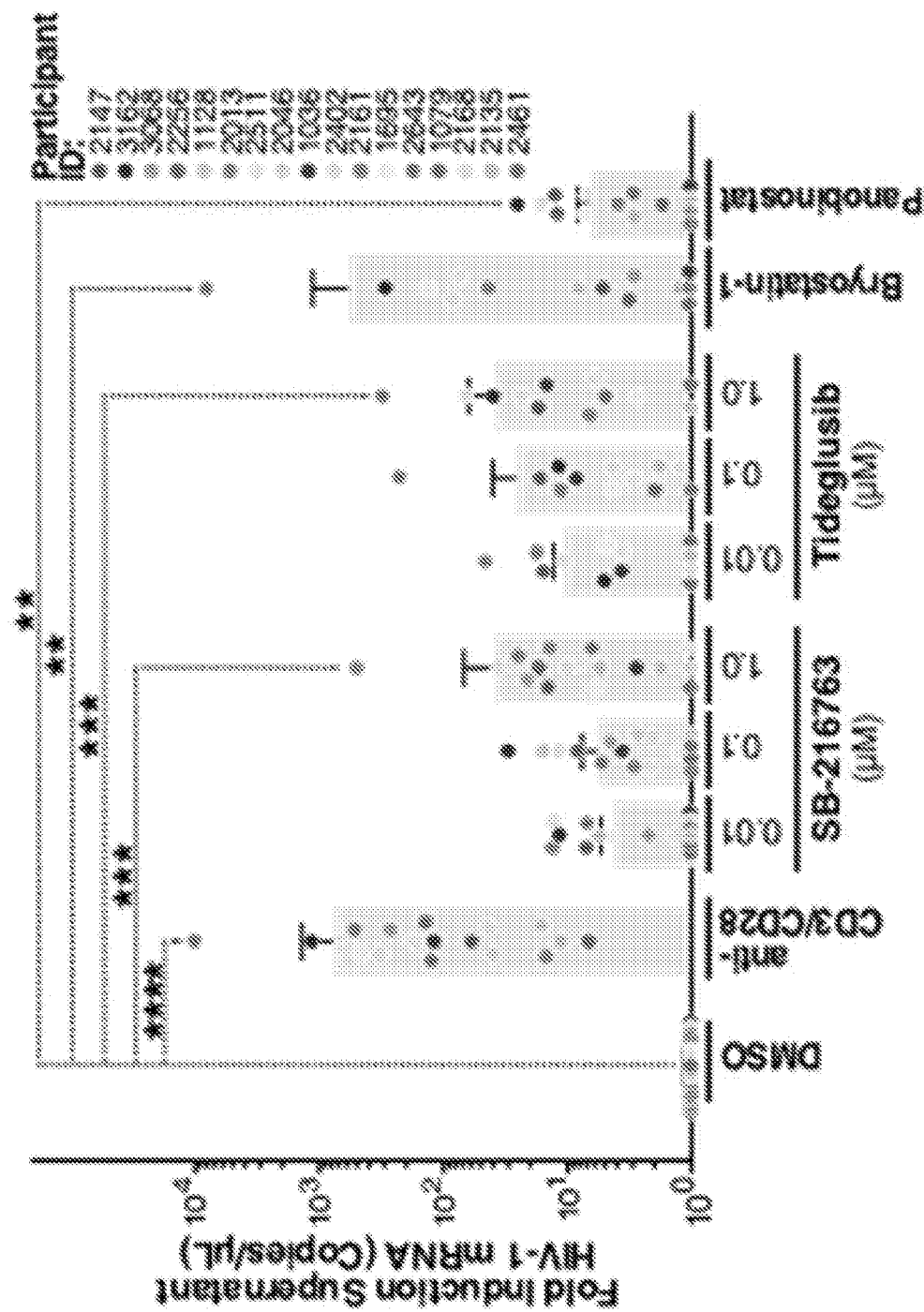

Two inhibitors of GSK-3 were used: SB-216763 inhibits GSK-3α and β, and tideglusib is specific for GSK-3β (FIG. 4A). Both were used at three concentrations from 0.01-1 µM. First-generation LRAs (i.e., bryostatin-1 and panobinostat) were used at concentrations that effectively reverse latency in model systems. All LRAs caused increases in virus-associated HIV-1 mRNA. The highest amount of virus-associated HIV-1 mRNA was realized with 10 nM bryostatin-1 (mean fold-change: anti-CD3/CD28=769.5; 1 µM SB-216763=38.61; 1 µM tideglusib=38.32; bryostatin-1=574.4; Panobinostat=6.304, FIG. 4B). However, by median values, 1 µM tideglusib resulted in release of two-fold more virus-associated HIV-1 mRNA than bryostatin-1 (median values: 1 µM tideglusib=10.3; bryostatin-1=5.086), suggesting that different donors responded in a much more homogeneous way to tideglusib than bryostatin-1. The similar results in latency reversion obtained with SB-216763 and tideglusib suggest that they have similar potency in reversing latency in primary CD4$^+$ T cells. Moreover, tideglusib has exhibited very low side effects in humans.

Figure 4D:
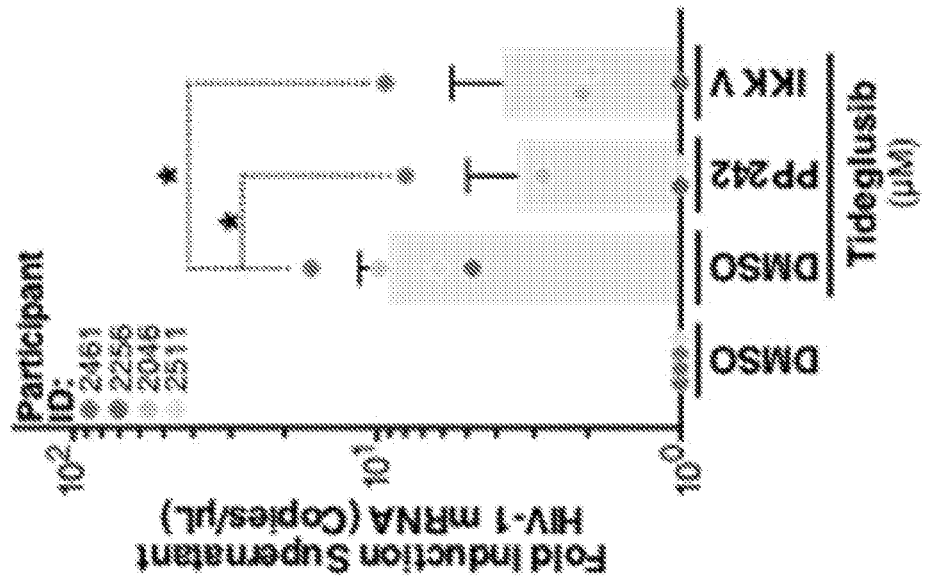
Figure 4C:
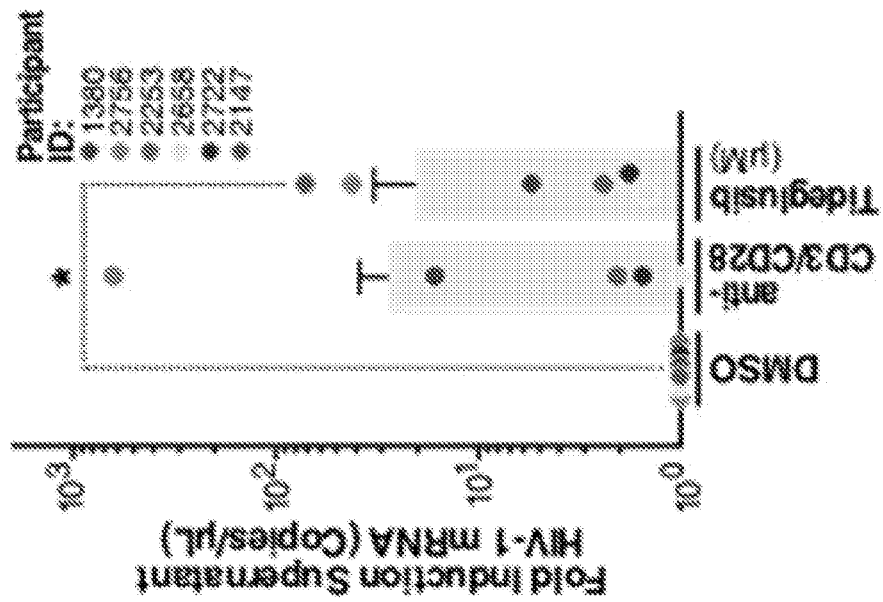

Next, the effectiveness of tideglusib in reversing HIV-1 latency in cultures of gut-associated lymphoid tissue (GALT) from HIV-positive donors on suppressive ART was examined. Biopsies were treated with digestion buffer and kept in culture with RPMI for subsequent LRA treatment and incubated with either anti-CD3/CD28 coated beads, 1 µM tideglusib, or left untreated (DMSO control). GALT cultures are extremely delicate and show very low viability even if left alone untreated for longer than 1 day. For this reason, GALT cultures were treated for only 24 hours. After treatment, virus-associated mRNA was isolated from the culture supernatant and quantified with ddPCR. After 24 hours of treatment with tideglusib, more virus-associated mRNA was found in the culture supernatant than that of untreated cells (1 µM tideglusib treatment: median value=20.69) (FIG. 4C). These results confirm that inhibition of GSK-3 in infected cells results in reactivation of latent virus. To confirm that the effects on latency reversion with tideglusib are due to induction of the AKT/mTOR pathway, a specific AKT agonist (i.e., SC79) on CD4$^+$ T cells isolated from five HIV-positive participants on suppressive ART was tested. 48 hours of treatment with SC79 also resulted in increased release of virions in the culture supernatant.

Activation of HIV-1 production is tightly controlled by the transcriptional activity of its long terminal repeat region (LTR). The LTR is regulated by viral proteins and host factors, including NF-κB, that become activated in virus-infected cells. mTOR may be required to reactivate latent HIV in the presence of a strong stimuli, such as anti-CD3/CD28. To investigate involvement of NF-κB and mTOR in tideglusib-mediated latency reversion, CD4$^+$ T cells isolated from HIV-positive donors were treated with 1 µM tideglusib alone or together with either an inhibitor of mTOR (PP242) or the IKK-2 inhibitor V (IKK V), a cell-permeable salicylamide compound that acts as an IKK-2 inhibitor by selectively blocking IκBα phosphorylation and preventing induction of NF-κB p65 nuclear translocation. After treatment, the released viruses in the culture supernatant were purified and quantified virus-associated HIV-1 mRNA with ddPCR. Addition of either an mTOR or an NF-κB inhibitor resulted in a decrease in virus production (ca. 66% less virus in tideglusib+PP242 and ca 62% less in tideglusib+IKK V). These results suggest that the molecular mechanism behind tideglusib-mediated latency reversion includes, to a similar extent, both functionalities of NF-κB and mTOR (FIG. 4D).

GSK-3 Inhibitors do not Induce Broad T-Cell Activation, Cytokine Release or Reduction of CD4$^+$ T-Cell Viability The effects of different LRAs on cell viability were examined. The same CD4$^+$ T-cell cultures used to study latency reversion (FIG. 4B) were tested for viability, expression of activation markers, and release of inflammatory cytokines. Treatment with GSK-3 inhibitors or bryostatin-1 caused minimal decrease in CD4$^+$T-cell viability, as assessed by cell titer blue assay (FIG. 5A) and confirmed by live/dead staining via flow cytometric analysis (data not shown). However, treatment with panobinostat caused a dramatic decrease in CD4$^+$ T-cell viability, resulting in an almost 50% cell death. CD4$^+$ T cells stimulated for 48 hours with either SB-216763 or tideglusib exhibited no increase in surface expression of the activation markers CD69 or CD25. On the other hand, treatment with anti-CD3/CD28-coated beads resulted in a marked increase in both CD69 and CD25, and treatment with the PKC agonists bryostatin-1 markedly increased CD69 surface expression (FIG. 5B, 5C). Although activation marker expression is a useful indication of an ongoing T-cell activation process, the production and release of pro-inflammatory cytokines provide a more direct measurement of functional T-cell activation, especially with regard to potential toxic effects. Global activation by anti-CD3/CD28-coated beads induced production and release of high levels of multiple cytokines, whereas GSK-3 inhibitors and panobinostat caused little or no cytokine production (FIG. 5D). Treatment of CD4$^+$ T cells with bryostatin-1 caused release of IFN-γ, IL-6, IL-13.

Treatment with Tideglusib Activates Proteins of the AKT/mTOR Pathway

Inactivation of GSK-3 can be triggered by different extracellular stimuli, such as binding of insulin with its receptor on the cell surface or engagement of TCR. This is mostly regulated through Phosphatidylinositol-4,5-bisphosphate 3-kinase (PI3K) and AKT. Specifically, PI3K activates AKT favoring its phosphorylation on S437. AKT, in turn, phosphorylates both GSK-3 isoforms (S9 of GSK-3β; S21 of GSK-3α), thus inhibiting them. The GSK-3α/β inhibitor SB-216763 induces phosphorylation of AKT on S473. Without intending to be bound by any particular theory, this may suggest a feedback regulation on AKT controlled by GSK-3. The treatment of CD4$^+$ T cells with the GSK-3β inhibitor tideglusib affects activation of AKT/mTOR in a time-dependent manner was tested. CD4$^+$ T cells from five HIV-positive individuals on ART were treated with 1 µM tideglusib for up to 6 hours, performing measurement at four times: 15, 30, 60 and 360 minutes. 15 minutes post-treatment, only a non-significant activation of the AKT/mTOR pathway was detected, as indicated by increased phosphorylation of GSK-3β, AKT and TSC2 (FIG. 6A). At 1 hour, significant phosphorylation values of the inhibiting phosphorylation of GSK-3β on S9 and the activating phosphorylation of p70S6K on T389 were detected, and an even higher fold-change of T389 phosphorylation at 6 hours. Phosphorylation of p70S6K on T389 is generally considered to show mTOR pathway activation. At 6 hours after treatment, statistically-relevant phosphorylation of AKT on S473 and the inhibiting phosphorylation of TSC2 on T1426 was also detected, which results in activation of mTORC1. Analysis of 700 transcripts showed that, upon treatment with tideglusib, the overall transcriptome changes predominantly after 1 and 6 hours treatment (data not shown), corresponding to activation of the mitogen-activated protein kinase (MAPK), PI3K, Ras, Wnt and TGFβ pathways and deactivation of the Hedgehog, Notch and Janus kinases (JAK) and signal transducer and activator of transcription proteins (STAT)-pathways (data not shown).

To further confirm the results, an unbiased phosphoproteomics analysis of CD4+ T cells treated with tideglusib was performed for only 15 minutes. FIG. 6C shows the phosphospectrum of S9 on GSK-3β, plus two new residues that were not included in the nanoString panel: T1295 on Rictor and S939 on TSC2. Together with T1426, S939 is another target of phosphorylation on TSC2 mediated by AKT; these two residues, once phosphorylated, prevent TSC2 from inhibiting mTORC1, releasing also the block on p70S6K. Phosphorylation of T1295 on Rictor is an uncharacterized phosphorylation that is present on activated CD4+ T cells. GO enrichment analysis of the tideglusib-treated and -untreated phosphoproteomics results also showed activation of TCR signaling (data not shown), together with overall spliceosome complex activity, transcription activation, mRNA processing and EGFR signaling.

Tideglusib Induces NF-κB Binding with Target DNA Sequences in an AKT-Dependent Manner.

Regulation of NF-κB functionalities is a complex process that is controlled at different levels and by different signaling pathways. For example, AKT promotes NF-κB activity by phosphorylating and activating IKK, an IκBα inhibitor, delivering it to proteasome degradation and consequently releasing p65. Here, p65 nuclear translocation and binding with target DNA sequences in nuclear extracts of CD4+ T cells was analyzed in the presence of tideglusib, tideglusib+ PP242 (a specific mTOR inhibitor), tideglusib+API-2 (a specific AKT inhibitor), or left untreated. p65 nuclear translocation in the presence of tideglusib peaked at 60 minutes after treatment initiation (except in participant 2, where nuclear p65 amount is slightly higher at 30 minutes, FIG. 7A). Addition of the AKT inhibitor API-2 reduced tideglusib-mediated p65 nuclear translocation at early time points (i.e. at 10 at 30 minutes, in all three donors). Co-treatment with the mTOR inhibitor PP242 showed less reduction in nuclear translocation.

FIG. 7B shows a time-dependent increase in p65/DNA binding upon treatment with tideglusib and a statistically-relevant reduction in the presence of the mTOR and AKT inhibitors at 60 minutes. In parallel, nuclear extracts from CD4+ T cells treated with anti-CD3/CD28 coated beads with or without PP24 or API-2 were analyzed. Similarly, p65 nuclear translocation and binding with dsDNA peaked at 60 minutes after treatment and addition of either PP242 or API-2 resulted in only a diminution of nuclear p65 and dsDNA binding activity. Nuclear extracts from participant 3 that showed less overall response to tideglusib, and a weaker dependency on mTOR and AKT inhibition, reported a similar response to TCR stimulation. These results suggest that tideglusib-mediated association between p65 and its DNA sites depends, at least in part, on mTOR and AKT activity.

Tideglusib is concluded to activate the AKT/mTOR pathway and that AKT activation favors nuclear translocation and activation of NF-kB. Without intending to be bound by any particularly theory, based on the results of the pathway analysis with nanoString, with phosphoproteomics and the data on NF-kB actation above, a schematic representation of the molecular mechanism of tideglusib in CD4+ T cells is shown in FIG. 8.

Inhibition of GSK-3 does not Affect CD4+ T-Cell Metabolism

The switch from OXPHOS to glycolytic metabolism during TCR stimulation involves multiple steps (e.g., the Notch1 and JAK-STAT signaling, engagement of the chemokine receptor CXCR4). These steps converge to activate PI3K, a key signaling molecule that allows mTORC2-mediated phosphorylation of AKT, which in turn phosphorylates the glucose transporter-1 (GLUT1) and increases its expression on the plasma membrane. AKT also activates mTORC1, and signals from this kinase to augment the glycolytic metabolism to support cell growth and proliferation. Interestingly, inhibition of GSK-3β increases glucose metabolism in skeletal muscle cells and cardiomyocytes.

Changes to the metabolism of resting CD4+ T-cells by tideglusib were studied. First, plasma membrane expression of GLUT1 in CD4+ T cells isolated from blood of three HIV-negative donors treated with 1 µM tideglusib was measured, stimulated with anti-CD3/CD28 coated beads, with or without the mTOR inhibitor PP242, or left untreated (DMSO control) for 2 or 24 hours. Incubation with tideglusib, which results in the AKT-mediated phosphorylation of S9 on GSK-3β (FIG. 9C), did not increase GLUT1 surface expression over the untreated control neither at an early (2 hours) or at a late (24 hours) time point, whereas cells activated with anti-CD3/CD28-coated beads had a marked increase in plasma membrane expression of GLUT1 (FIGS. 9A and 9B). Addition of the mTOR inhibitor did not significantly alter expression of GLUT1 either.

Seahorse technology was applied to study changes in the glycolytic capacity of CD4+ T cells. CD4+ T cells were tested for 24 hours under the same conditions as in FIG. 9B. Extracellular acidification rate (ECAR), obtained during a standard mitochondrial stress test was measured, including treatments with a combination of actinomycin A (AA) and rotenone (Rot), inhibitors of complex III and complex I, respectively (FIG. 9D). Response to Rot/AA did not result in an increase in the compensatory glycolysis (FIG. 9E) (i.e., how well cells are primed to use glycolysis when ATP production from OXPHOS is impaired), but a difference in basal glycolysis was found in samples untreated or treated with tideglusib (FIG. 9F). However, given the very low change in pmol/min (i.e., mean value of DMSO-treated samples=11.88 vs mean value of tideglusib-treated sample=17.43), treatment with tideglusib results in increase in basal glycolysis could not be confirmed. Furthermore, increased medium acidification in cultures of CD4+ T cells treated with tideglusib or SB-216763 for 24 hours in a colorimetric cell-based assay was not detected (FIG. 9G): After 24 hours of treatment, either SB-216763 or tideglusib did not result in an increase of L-lactate in the culture media, whereas incubation with anti-CD3/CD28 coated beads, caused a 1-log increase in L-lactated production (FIG. 9G). Incubation with the glycolysis inhibitor 2-deoxy-D-glucose (2-DG) dramatically reduced L-lactate production in all treated and untreated (i.e., DMSO control) samples. Without intending to be bound by any particular theory, these data suggest that tideglusib-mediated AKT activation, which resulted in the inhibiting phosphorylation of S9 on GSK-3β (FIG. 9C), is not sufficient to shift CD4+ T-cell metabolism from OXPHOS to glycolysis, suggesting the requirement of additional signaling.

Tideglusib Preserves Viability and Cytotoxic Effector Functions of CD8+ T and NK Cells HIV-1-specific CD8+ T cells detect and eliminate latently infected cells after in vitro latency reversal. Specifically, ART-suppressed chronically-infected individuals retained CD8+ T cell clones capable of eliminating autologous infected CD4+ T cells. After latency reversal, a "killing approach" may, in certain instances, include administration of a cocktail of broadly neutralizing antibodies or a therapeutic vaccination that will direct CTL and NK cells to the reservoir sites to identify and eliminate infected CD4+ T cells. These observations represent an optimistic foundation for using LRAs in combination with immunotherapeutic strategies to boost the endogenous HIV-1-specific CD8+ T cell response and/or redirect the response toward conserved epitopes.

The effect on viability and activation of CD8+ T and NK cells after treatment with tideglusib was studied. Tideglusib did not reduce viability of CD8+ T or NK cells, but the HADC inhibitor panobinostat reduced total CD8+ T cells approximately 40% and total NK cells approximately 60% (FIGS. 10A and 10D). Pre-treatment with 1 µM tideglusib for 48 hours, followed by CD8+ T cell and NK cell activation with PMA/ionomycin or incubation with K562 cells, respectively, resulted in an increase in IFN-γ production in both CD8+ T (FIG. 10B) and NK cells (FIG. 10E) and in an increased surface expression of CD107a in CD8+ T cells (FIG. 10C), which was less marked in NK cells (FIG. 10F). Given its high toxicity, IFN-γ production and expression of CD107a in panobinostat-treated samples was not shown here. Of note, the few cells that survive panobinostat treatment seem to be highly cytotoxic (i.e. show both high IFN-γ production and expression of CD107a). Overall, CD8+ T and NK cells cytotoxic effector functions were mildly enhanced in the presence of the GSK-3β inhibitor.

The effect of CD8+ T-mediated killing of HIV-positive CD4+ T cells from HIV-positive progressors (i.e. individuals with progressive decline in CD4+ T cell count and detectable HIV-1 RNA levels) with tideglusib was studied. ART does not restore the defect in CD8+ T cell proliferation or killing of target CD4+ T cells.

Effector peripheral mononuclear cells (PBMCs) were stimulated for 6 days with 1 µM tideglusib and combined them with fresh infected CD4+ T targets for 1 hour, to assess killing. Treating the infected PBMCs with tideglusib did not alter production of granzyme B (GrB) or prevent CD8+ T-mediated infected CD4+ T-cell elimination (ICE), showing that cytotoxic effector functions of CTLs were not impaired by tideglusib (FIGS. 10G and 10H). As positive control, GrB production and ICE in HIV-specific CD8 T cells from three long-term non progressor/elite controller (LTNP/EC) individuals (donors characteristics reported in the Experimental Procedures, above) that typically mediate greater lysis of infected targets than cells compared to progressors were analyzed.

Results Summary

GSK-3β as a new target for therapeutic latency reversion is provided herein and experimental data demonstrate that GSK3 inhibitors are efficient LRAs, ex vivo in cells isolated from blood and GALT of HIV-positive individuals on suppressive ART. Release of viruses (i.e., virus-associated mRNA) was quantified in the presence of tideglusib, a non-toxic small-molecule compound and inhibitor of GSK-3β that reverses HIV-1 latency without inducing T-cell activation or impairing the cytotoxic effector functions of CD8+ T, NK cells or CTLs isolated from positive donors on ART. Viral protein production after latency reversal may be sufficient to drive elimination of these cells by viral cytopathic effects or immune-mediated clearance. Measurement of virion production after ex vivo treatment of CD4+ T cells with LRAs serves as a proxy for viral protein production. Thus, the results presented herein show that tideglusib induce production and release of about 40-fold more virions than untreated control samples in blood CD4+ T cells (FIG. 4B), and that its action is mediated by both mTOR and NF-κB (FIG. 4D). The efficacy of another GSK-3 inhibitor, SB-216763, specific for both GSK-3 isoforms α and β was also tested. Treatment with SB-216763, as measured by ddPCR, resulted in a similar amount of virus-associated mRNA in the culture of treated CD4+ T cells, suggesting that inhibition of the α isoform of GSK-3 may be redundant. Importantly, latency reversion mediated by tideglusib was detected also in GALT cultures, where it resulted in over 20-fold more virus release than untreated control (FIG. 4C). A 2-day treatment with GSK-3β inhibitors did not decrease T-cell viability (FIG. 5A) and did not result in surface expression of activation markers (FIG. 5B, 5C) or the release of inflammatory cytokines (FIG. 5D).

Prolonged treatment with tideglusib was shown to result in a very low incidence of side-effects (i.e., moderate, asymptomatic and fully reversible increase of transaminase in 30% of the cases). Given the ability of tideglusib to induce NF-κB (FIG. 8), lack of T-cell activation and cytokine release was an unexpected outcome. 2-day treatment with tideglusib reduces expression of CD69 transcripts in primary CD4+ T cells isolated from fresh human tonsils.

Inhibition of GSK-3β with tideglusib resulted in activation of the AKT/mTOR signaling cascade, as shown by Nanostring and phosphoproteomics analysis of treated CD4+ T cells. Statistically-relevant inhibition of GSK-3β and activation of p70S6K already 1 hour after treatment was observed. At 6 hours after treatment, activation of AKT and inhibition TSC2 (FIG. 6A) was detected, which acts as an inhibitor of mTORC1. AKT activation involves its recruitment to the plasma membrane through binding with PI3K-generated PtdIns(3,4,5)P$_3$, which imposes a conformational change on AKT and allows subsequent phosphorylation events, such as mTORC2 (Rictor)-mediated phosphorylation on S473 (ref). mTOR activation regulates a myriad of cellular functions, including glucose metabolism. Other signaling pathways that have been associated with glucose metabolism in T cells are the extracellular signal-related kinase (ERK), JAK-STAT, MAPK, and hexokinase II. These pathways co-operate with AKT and mTOR to regulate metabolic reprograming of T cells. However, the magnitude by which these pathways regulate T-cell metabolism may vary depending on the precise environmental conditions. Induction of aerobic glycolysis after treatment with tideglusib was not detected (FIG. 9). Activation of aerobic glycolysis in T cells is a highly regulated process, which involves several steps at transcriptional and post-transcriptional level that might differ from other cell types. Without intending to be bound by any particular theory, decreased activation of the JAK-STAT pathway shown by the nanoString analysis (data not shown) may be responsible for the failure of tideglusib inducing the switch to glycolytic metabolism in CD4+ T cells. Tideglusib does not induce dramatic alteration of T-cell metabolism, but rather drives targeted transcription of HIV genes without affecting CD4+ T cell lifecycle.

Phosphoproteomics analysis confirmed inhibition of GSK-3β and TSC2 in the presence of tideglusib and revealed phosphorylation of Rictor on T1295, a phosphorylation site that was detected in T cells upon stimulation of TCR (FIG. 6B). Nanostring analysis of 700 mRNA transcripts confirmed that tideglusib treatment partially mimics downstream TCR signaling, bypassing T-cell activation and cytokine release. Treatment for 1 and 6 hours with tideglusib showed increased activation of MAPK, PI3K and Ras and activation of the Wnt pathway that is directly regulated by GSK-3 (data not shown). GO enrichment analysis of the tideglusib-treated vs untreated phosphoproteomics results shows that inhibition of GSK-3β with tideglusib induce, immediately after treatment (i.e., after 15 minutes), spliceosome complex activity, overall transcription activation and mRNA processing (data not shown). Activation of TCR and EGFR were also reported, suggesting that GSK-3β might regulate proteins upstream of AKT/mTOR in resting CD4+ T cells.

Without intending to be bound by any particular theory, FIG. 8 summarizes a proposed mechanism that involves GSK-3 mediated inhibition of the insulin receptor substrate 1 (IRS-1) that would in turn reduce AKT activation. Inhibition of GSK-3, would then "activate" AKT by removing the block on IRS-1. Alternatively, GSK-3 may inhibit Rictor, as previously demonstrated in MDA-MB-435 cells, by phosphorylating it on S1235, an event that can be reversed by treatment with SB-216763. The findings presented herein on latency reversion for these active agents suggests a mechanistically interesting relevance of the GSK-3/AKT/mTOR pathway. Unraveling the detailed mechanism of GSK-3 inhibitors in CD4+ T cells might help further understanding the molecular mechanism underlying HIV-1 latency and in the design of new efficient and non-toxic LRAs.

Certain HDAC inhibitors impair the ability of HIV-1-specific CD8+ T to kill HIV-1-infected cells, both ex vivo and in in vitro models. This impairment of the HIV-1 CTL response by HDAC inhibitors may limit their clinical utility in eradication trials. As demonstrated herein, GSK-3 inhibitors enhance cytotoxic effector functions of CD8+ T cells but prevented surface expression of PD-1, and in NK cells, tideglusib increases NK-mediated killing of target cells. Tideglusib was shown herein to slightly enhance IFN-γ production and CD107a surface expression in both activated CD8+ T and NK cells, without impairing impair cell viability (FIG. 10A-10F). This result highlights the potential GSK-3 inhibitors have as LRAs and to immune-based approaches to reduce the reservoir. Furthermore, proof that CD8+ T cells isolated from HIV-progressors treated with tideglusib for 6 days can still kill target infected CD4+ T cells (FIGS. 10G and 10H) suggests that GSK-3 inhibitors (e.g., tideglusib) may support killing of infected cells in vivo.

Using a combination of techniques (e.g., ddPCR flow cytometry, nanoString and phosphoproteomics), GSK-3 inhibitors were identified as new class of non-toxic LRAs effective ex vivo on CD4+ T cells from infected individuals on suppressive ART. Tideglusib, is safe (i.e., non-toxic) and well tolerated in humans and showed high tissue-permeability also in the brain. The degree of latency reversal induced by tideglusib would be expected to produce measurable levels of T-cell activation. However, tideglusib and in general GSK-3β inhibitors reverse latency without increasing surface expression of CD69/CD25 and without inducing pro-inflammatory cytokine production. Furthermore, tideglusib preserves cytotoxic effector functions of CD8+ T, NK cells and CTL-mediated killing of target cells.

Example 6—Glycogen Synthase Kinase 3 Inhibitors—Reversal of HIV Latency in CD4+ T Cell Model Formed with Human Lymphoid Tissue A lymphoid tissue model of HIV latency was used to assess glycogen synthase kinase 3 inhibitors as a potential latency reversing agent. The lymphoid tissue model was chosen because most of the latent reservoir is found in lymphoid tissues rather than in blood. Resting CD4+ T cells were purified from human tonsil and spinoculated with HIV-GFP reporter viruses, creating a population of latently infected cells. When treated with a GSK-3 inhibitor, SB216763, a 90-fold induction of the GFP reporter at doses between 100-1000 nM (FIG. 11A) was seen. The $IC_{50}$ for this compound is approximately 1 μM raising the possibility of an even greater response when more than 50% of the enzyme sites are titrated with inhibitor. In contrast, anti-CD3/anti-CD28 antibodies, normally a highly active standard to which all other LRAs are compared, induced GFP expression in only 5-6% of cells-roughly a 16-fold lower response than that with the GSK-3i. First-generation LRAs, byrostatin-1, JQ-1 and panobinostat, produced only minimal latency reversal.

Rapamycin, a selective mTORC1 inhibitor, blocked the activating effects of the SB216763, implicating mTORC1 in the reversal of latency. Cell viability assessed by Cell Titer Blue staining was not affected by the SB216763 treatment, although toxicity was observed with PMA and panobinostat (FIG. 11B). Remarkably, the GSK-3 inhibitor did not induce cellular activation over that obtained with DMSO control as assessed by surface expression of the CD69 or CD25 activation markers (FIG. 12). These studies suggest that GSK3i's can potently reverse latency in a primary tonsil CD4+ T cell model of HIV latency in the absence of apparent toxicity or overt cellular activation.

Example 7—Glycogen Synthase Kinase 3 Inhibitors—Reversal of HIV Latency in Human Cells Latency reversing effects of two different glycogen synthase kinase 3 inhibitors were investigated in HIV-infected patients cells on suppressive anti-retroviral therapy. To measure reactivation of virus in these cultures where only ~1 CD4+ T cell in every million is latently infected, digital droplet PCR was used to quantify extracellular viral RNA corresponding to newly budded virions emanating from reactivated reservoir cells. Measuring such a late stage in the viral lifecycle helps reduce (but does not eliminate) detection of defective HIV proviruses. Cells were stimulated with either SB216763, a GSK-3i or tideglusib. At equivalent doses, tideglusib and SB216763 exhibited comparable activity. Tideglusib induced potent, dose-related activation of latent virus production reaching ~40-fold induction at the highest concentration (FIG. 13A). In these patient cells, anti-CD3/anti-CD28 antibodies were quite active with effects ranging between 10-$10^4$-fold depending on the donor. 3 of 14 and 1 of 8 subjects did not respond to the highest dose of SB216763 or tideglusib respectively indicating the presence of a low responder subset. Neither tideglusib nor SB216763 induced toxicity based on cell-titer blue testing (FIG. 13B), nor did these agents induce detectable cellular activation based on surface expression of CD69 or CD25 at 24 hours or 48 hours (FIG. 13C).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of reactivating a latent human immunodeficiency virus (HIV) integrated into the genome of a cell infected with HIV, the method comprising contacting the cell with a glycogen synthase kinase 3 inhibitor, wherein the glycogen synthase kinase 3 inhibitor reactivates the latent HIV integrated into the genome of the cell, wherein the glycogen synthase kinase 3 inhibitor is Tideglusib (4-benzyl-2-(naphthalen-1-yl)-1,2,4-thiadiazolidine-3,5-dione)) or pharmaceutically acceptable salt thereof.

2. The method of claim 1, wherein the contacting occurs in lymphoid tissue.

3. A method of reducing the number of cells containing a latent human immunodeficiency virus in an individual, the method comprising administering to the individual an effective amount of a glycogen synthase kinase 3 inhibitor, wherein the glycogen synthase kinase 3 inhibitor reactivates latent HIV integrated into the genome of one or more cells in the individual, wherein the glycogen synthase kinase 3 inhibitor is Tideglusib (4-benzyl-2-(naphthalen-1-yl)-1,2,4-thiadiazolidine-3,5-dione)) or pharmaceutically acceptable salt thereof.

4. The method of claim 3, wherein said administering is effective to reduce the number of cells containing a latent human immunodeficiency virus in the individual by at least 20%.

5. A method of treating a human immunodeficiency virus (HIV) infection in an individual, the method comprising:
  administering to an individual an effective amount of a glycogen synthase kinase 3 inhibitor, wherein the glycogen synthase kinase 3 inhibitor reactivates latent HIV integrated into the genome of a cell in the individual, wherein the glycogen synthase kinase 3 inhibitor is Tideglusib (4-benzyl-2-(naphthalen-1-yl)-1,2,4-thiadiazolidine-3,5-dione)) or pharmaceutically acceptable salt thereof; and
  administering to the individual an effective amount of a second active agent, wherein the second active agent inhibits an immunodeficiency virus function selected from viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity.

\* \* \* \* \*